United States Patent [19]

Takasugi et al.

[11] Patent Number: 5,047,411
[45] Date of Patent: Sep. 10, 1991

[54] BENZAZOLE COMPOUNDS AND PHARMACEUTICAL COMPOSITION COMPRISING THE SAME

[75] Inventors: Hisashi Takasugi, Osaka; Yousuke Katsura, Toyonaka; Yoshikazu Inoue, Amagasaki; Shigetaka Nishino, Osaka; Takao Takaya, Kawanishi, all of Japan

[73] Assignee: Fujisawa Pharmaceutical Co., Ltd., Osaka, Japan

[21] Appl. No.: 397,669

[22] Filed: Aug. 23, 1989

[30] Foreign Application Priority Data

Aug. 25, 1988 [GB] United Kingdom ................ 8820231

[51] Int. Cl.$^5$ .................. C07D 413/06; A61K 31/44; A61K 31/42
[52] U.S. Cl. .................................... 514/300; 514/318; 514/338; 546/121; 546/194; 546/270
[58] Field of Search ............... 514/375, 300, 318, 338; 548/221, 222, 217

[56] References Cited

U.S. PATENT DOCUMENTS 4,721,718 1/1988 Adelstein et al. .................. 514/300

FOREIGN PATENT DOCUMENTS 111685 6/1984 European Pat. Off. .
120589 10/1984 European Pat. Off. .

*Primary Examiner*—John M. Ford
*Attorney, Agent, or Firm*—Oblon, Spivak, McClelland, Maier & Neustadt

[57] ABSTRACT

The benzazole compounds of this invention can be represented by the following formula [I]:

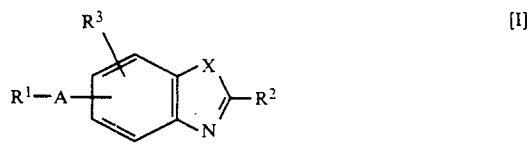

wherein
$R^1$ is aryl or a heterocyclic group, each of which may have suitable substitutent(s),
$R^2$ is hydroxy, mercapto, lower alkylthio, sulfo, lower alkyl, amino or substituted amino,
$R^3$ is hydrogen, halogen or lower alkoxy,
A is lower alkenylene, lower alkylene optionally substituted with hydroxy, or a group of the formula:

$$-A'-Q-A''-,$$

in which A' is lower alkylene, A'' is lower alkylene or a single bond, and Q is O or S, and
X is O, S, NH or $N-R^4$, in which $R^4$ is lower alkyl.

More particularly, it relates to benzazole compounds and pharmaceutically acceptable salts thereof which have antiulcer activity and $H_2$-receptor antagonism, to processes for the preparation thereof, to a pharmaceutical composition comprising the same and to a method for the treatment of ulcers in human being or animals.

4 Claims, No Drawings

BENZAZOLE COMPOUNDS AND PHARMACEUTICAL COMPOSITION COMPRISING THE SAME

This invention relates to new benzazole compounds and pharmaceutically acceptable salts thereof.

More particularly, it relates to new benzazole compounds and pharmaceutically acceptable salts thereof which have antiulcer activity and $H_2$-receptor antagonism, to processes for the preparation thereof, to a pharmaceutical composition comprising the same and to a method for the treatment of ulcer in human being or animals.

One object of this invention is to provide new benzazole compounds and pharmaceutically acceptable salts thereof which possess antiulcer activity and $H_2$-receptor antagonism.

Another object of this invention is to provide processes for the preparation of said benzazole compounds and salts thereof.

A further object of this invention is to provide a pharmaceutical composition comprising, as an active ingredient, said benzazole compounds or pharmaceutically acceptable salts thereof.

Still further object of this invention is to provide a therapeutical method for the treatment of ulcer in human being or animals.

The object benzazole compounds of this invention and can be represented by the following general formula [I]:

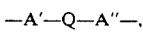

wherein
$R^1$ is aryl or a heterocyclic group, each of which may have suitable substituent(s),
$R^2$ is hydroxy, mercapto, lower alkylthio, sulfo, lower alkyl, amino or substituted amino,
$R^3$ is hydrogen, halogen or lower alkoxy,
A is lower alkenylene, lower alkylene optionally substituted with hydroxy, or a group of the formula:

$$-A'-Q-A''-,$$

in which A' is lower alkylene, A'' is lower alkylene or a single bond, and Q is O or S, and
X is O, S, NH or N—$R^4$, in which $R^4$ is lower alkyl, As to the object compound [I], it is to be noted that when $R^2$ is hydroxy, mercapto, amino or mono substituted amino, the compound [I] can exist in the tautomeric forms as follows:

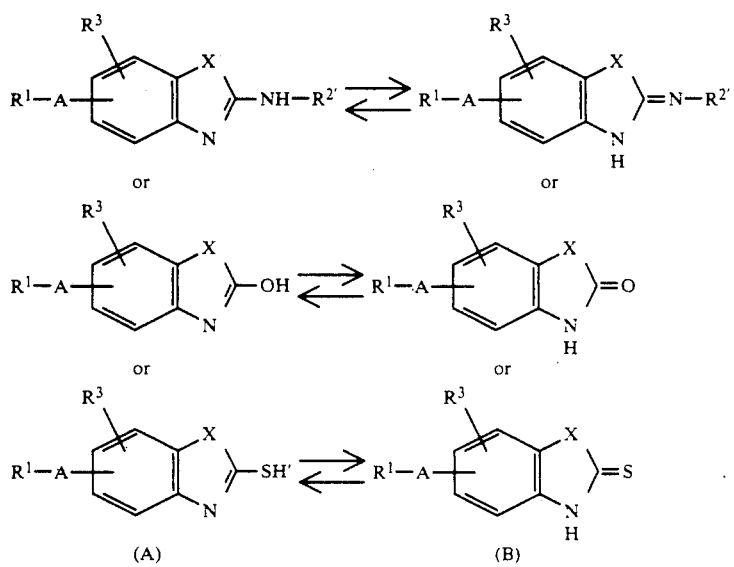

wherein
$R^{2'}$ is hydrogen or a substituent on the mono substituted amino, and
$R^1$, $R^3$, A and X are each as defined above.

Both of the above tautomeric isomers [i.e. benzazole form (A) and benzazolidine form (B)] are included within the scope of the present invention, and in the present specification and claims, however, the object compound [I] is represented as benzazole form (A) for the convenient sake.

The object compound [I] or its salt can be prepared by processes as in the following reaction schemes.

Process 1

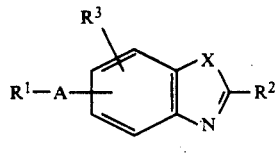

[II]
or its salt

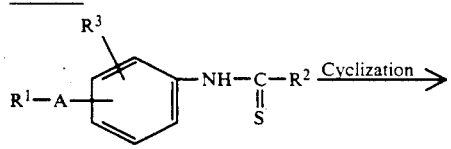

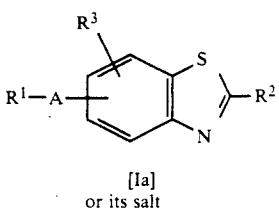

[Ia]
or its salt

Process 2

-continued
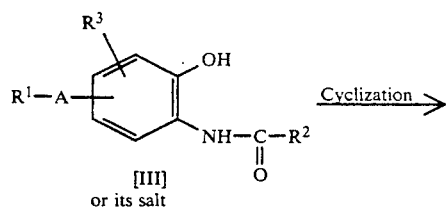
[III] or its salt
Cyclization →
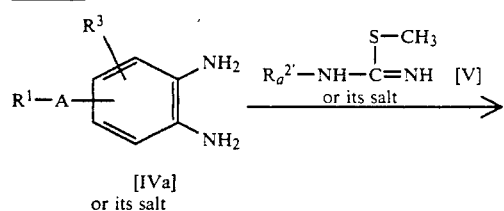
[Ib] or its salt
Process 3
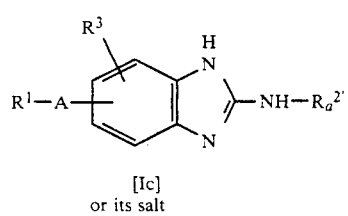
[IVa] or its salt
[V] or its salt
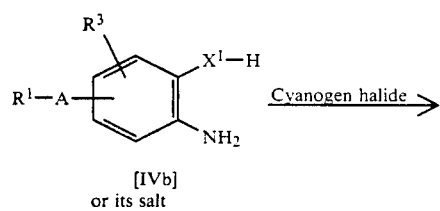
[Ic] or its salt
Process 4
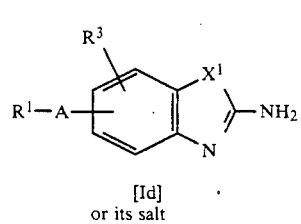
[IVb] or its salt
Cyanogen halide →
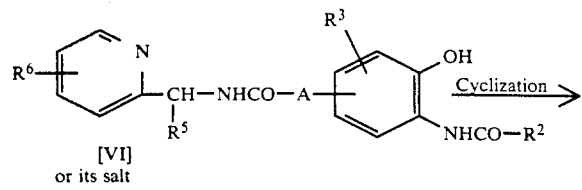
[Id] or its salt
Process 5
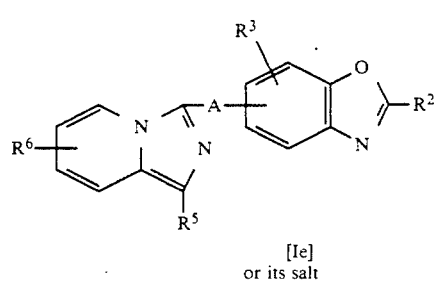
[Ie] or its salt
Process 6
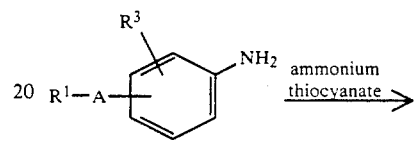
[VII] or its salt
ammonium thiocyanate →
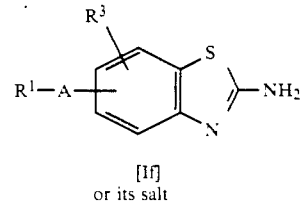
[If] or its salt
Process 7
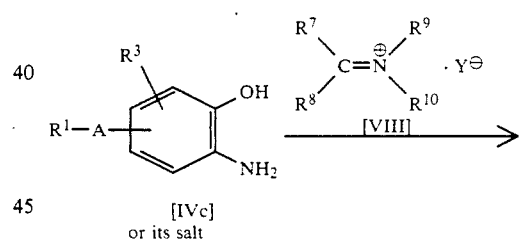
[IVc] or its salt
[VIII] →
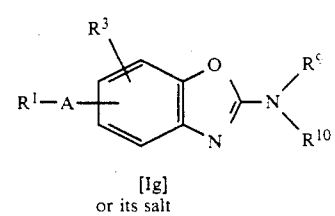
[Ig] or its salt
Process 8
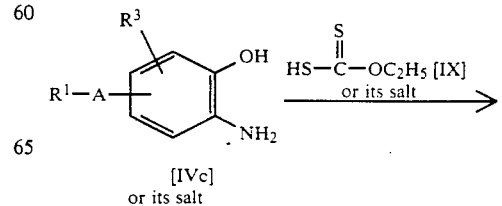
[IVc] or its salt
HS−C(=S)−OC$_2$H$_5$ [IX] or its salt →

-continued

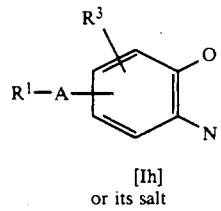

[Ih]
or its salt

Process 9

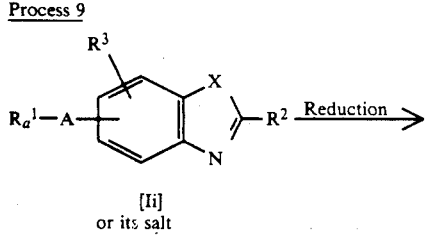

[Ii]
or its salt

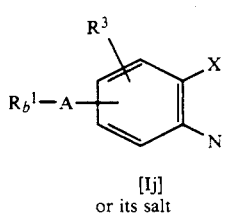

[Ij]
or its salt

Process 10

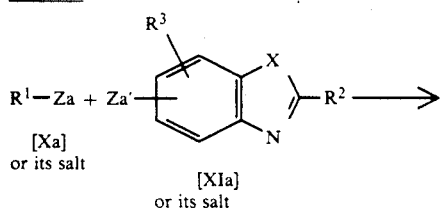

[Xa]
or its salt    [XIa]
or its salt

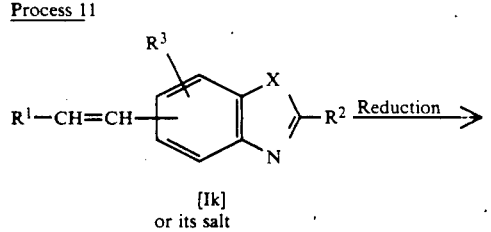

[Ik]
or its salt

Process 11

R¹—CH=CH— (ring) —R² Reduction →

[Ik']
or its salt

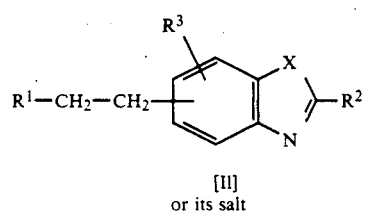

[Il]
or its salt

Process 12

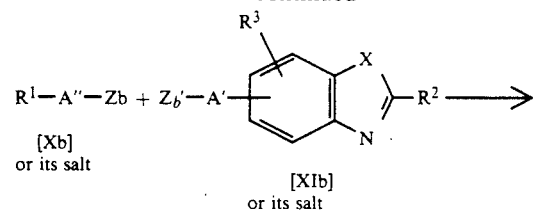

[Xb]
or its salt    [XIb]
or its salt

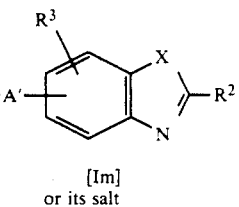

[Im]
or its salt

Process 13

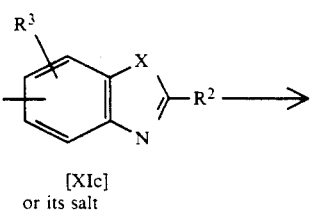

[Xc]
or its salt    [XIc]
or its salt

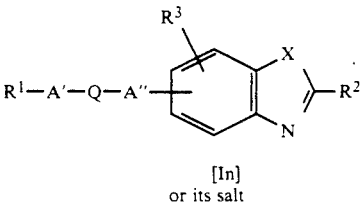

[In]
or its salt wherein $R_a^1$ is imidazopyridyl which may have suitable substituent(s), $R_b^1$ is tetrahydroimidazopyridyl which may have suitable substituents(s), $R_A^{2'}$ is acyl, $R^5$ and $R^6$ are each hydrogen or suitable substituent at a heterocyclic group for $R^1$, $R^7$ and $R^8$ are each halogen, $R^9$ and $R^{10}$ are each lower alkyl, $X^1$ is O, NH or N—$R^4$, in which $R^4$ is as defined above, $Y^\ominus$ is anion, Za is formyl or triphenylphosphonium, Za' is triphenylphosphonium when Za is formyl, or Za' is formyl when Za is triphenylphosphonium, Zb is halogen or a group of the formula: —Q—Zc, in which Zc is hydrogen or amidino, and Q is as defined above, Zb' is a group of the formula:

—Q—ZC, in which Q and Zc are each as defined above, when Zb is halogen, or

Zb' is halogen, when Zb is a group of the formula: —Q—Zc, in which Q and Zc are each as defined above, and $R^1$, $R^2$, $R^3$m A, A', A", Q and X are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "aryl" may be phenyl, naphthyl, tolyl, xylyl, mesityl, cumenyl, and the like, in which preferable one is phenyl.

The heterocyclic group may include saturated or unsaturated, monocyclic or polycyclic heterocyclic group containing at least one hetero-atom selected from oxygen, sulfur and nitrogen atoms.

Suitable "heterocyclic group" may include N-containing heterocyclic group such as unsaturated, 3 to 8-membered, more preferably 5 or 6-membered heteromonocyclic group containing 1 to 4-nitrogen atom(s), for example, pyrrolyl, pyrrolinyl, imidazolyl, pyrazolyl, pyridyl, pyridyl N-oxide, dihydropyridyl, tetrahydropyridyl [e.g. 1,2,3,6-tetrahydropyridyl, etc.], pyrimidinyl, pyrazinyl, pyridazinyl, triazinyl, triazolyl, tetrazinyl, tetrazolyl, etc., saturated, 3 to 8-membered heteromonocyclic group containing 1 to 4 nitrogen atom(s), for example, pyrrolidinyl, imidazolidinyl, piperidyl, piperazinyl, etc., unsaturated, condensed heterocyclic group containing 1 to 5 nitrogen atom(s), for example, indolyl, isoindolyl, indolizynyl, benzimidazolyl, quinolyl, isoquinolyl, indazolyl, benzotriazolyl, imidazopyridyl [e.g. imidazo[1,2-a]pyridyl, imidazo[1,5-a]pyridyl, etc.], tetrahydroimidazopyridyl [e.g. 5,6,7,8-tetrahydroimidazo[1,2-a]pyridyl, etc.], imidazopyrimidinyl [e.g. imidazo[1,2-a]pyrimidinyl, etc.], etc.;

O-containing heterocyclic group such as unsaturated, 3 to 8-membered heteromonocyclic group containing an oxygen atom, for example, furyl, etc., unsaturated, condensed heterocyclic group containing 1 to 2 oxygen atom(s), for example, benzofuryl, etc.;

S-containing heterocyclic group such as unsaturated, 3 to 8-membered heteromonocyclic group containing a sulfur atom, for example, thienyl, etc., unsaturated, condensed heterocyclic group containing 1 to 2 sulfur atom(s), for example, benzothienyl, etc.;

N- and O- containing heterocyclic group such as unsaturated, 3 to 8-membered heteromonocyclic group containing 1 to 2 oxygen atom(s) and 1 to 3 nitrogen atom(s), for example, oxazolyl, isoxazolyl, oxadiazolyl, etc., saturated, 3 to 8-membered heteromonocyclic group containing 1 to 2 oxygen atom(s) and 1 to 3 nitrogen atom(s), for example, morpholinyl, syndonyl, etc., unsaturated, condensed heterocyclic group containing 1 to 2 oxygen atom(s) and 1 to 3 nitrogen atom(s), for example, benzoxazolyl, benzoxadiazolyl, etc.; N- and S- containing heterocyclic group such as unsaturated, 3 to 8-membered heteromonocyclic group containing 1 to 2 sulfur atom(s) and 1 to 3 nitrogen atom(s), for example, thiazolyl, isothiazolyl, thiadiazolyl, etc., saturated, 3 to 8-membered heteromonocyclic group containing 1 to 2 sulfur atom(s) and 1 to 3 nitrogen atom(s), for example, thiazolidinyl, thiomorpholinyl, etc., unsaturated, condensed heterocyclic group containing 1 to 2 sulfur atom(s) and 1 to 3 nitrogen atom(s), for example, benzothiazolyl, benzothiadiazolyl, etc.; and the like.

Suitable substituent(s) at aryl or a heterocyclic group for $R^1$ may include amino, substituted amino, hydroxy, substituted hydroxy, carboxy, acyl, halogen, lower alkyl, substituted lower alkyl and the like.

Suitable substituent(s) in the terms "imidazopyridyl which may have suitable substituent(s)" and "tetrahydroimidazopyridyl which may have suitable substituent(s)" can be referred to the ones at a heterocyclic group for $R^1$ as exemplified above.

Suitable "substituted amino" may be amino substituted with substituent(s) such as acyl, diaminomethylene, lower alkyl, lower alkenyl, amidino, lower alkylamino(lower)alkylidene or the like.

Suitable substituent(s) in the terms "mono substituted amino" and "a substituent on the mono substituted amino" can be referred to the ones in the term "substituted amino" as exemplified above.

Suitable "substituted hydroxy" may be hydroxy substituted with substituent(s) such as acyl, lower alkyl or the like.

Suitable "substituted lower alkyl" may be lower alkyl substituted with substituent(s) such as aryl, hydroxy, halogen, lower alkoxy, amino, lower alkylamino, a heterocyclic group, azido or the like.

Suitable "acyl" may be lower alkanoyl [e.g. formyl, acetyl, propionyl, butyryl, isobutyryl, valeryl, isovaleryl, pivaloyl, 4-methylvaleryl, ethylbutyryl, etc.], lower alkanoyloxy(lower)alkanoyl [e.g. acetoxyacetyl, acetoxypropionyl, propionyloxypropionyl, etc.], cyclo(lower)alkylcarbonyl [e.g. cyclopropylcarbonyl, cyclobutylcarbonyl, cyclopentylcarbonyl, cyclohexylcarbonyl, etc.], carbamoyl, mono- or di(lower)alkylcarbamoyl [e.g. methylcarbamoyl, ethylcarbamoyl, propylcarbamoyl, isopropylcarbamoyl, butylcarbamoyl, pentylcarbamoyl, isobutylcarbamoyl, tert-butylcarbamoyl, dimethylcarbamoyl, diethylcarbamoyl, methylethylcarbamoyl, methylisopropylcarbamoyl, methylisobutylcarbamoyl, etc.], lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], or the like.

Suitable "halogen" may be fluorine, chlorine, bromine or iodine.

Suitable "lower alkyl" and lower alkyl moiety in the terms "substituted lower alkyl", "lower alkylamino" and "lower alkylthio" may be a straight or branched one such as methyl, ethyl, propyl, isopropyl, butyl, isobutyl, tert-butyl, pentyl, hexyl or the like, in which the preferable one is $C_1$–$C_4$ alkyl.

Suitable "lower alkenyl" may be a straight or branched one such as vinyl, allyl, isopropenyl, butenyl, pentenyl or the like, in which the preferable one is $C_2$–$C_4$ alkenyl.

Suitable "lower alkylamino(lower)alkylidene" may be methylaminomethylene, dimethylaminomethylene, diethylaminomethylene or the like.

Suitable "lower alkoxy" may be methoxy, ethoxy, propoxy, isopropoxy, butoxy, isobutoxy, tert-butoxy, pentyloxy, hexyloxy or the like, in which the preferable one is $C_1$–$C_4$ alkoxy.

Suitable "lower alkenylene" may be vinylene, propenylene, butenylene, pentenylene, butadienylene, pentadienylene or the like, in which the preferable one is vinylene.

Suitable "lower alkylene" may be a straight or branched one such as methylene, ethylene, trimethylene, tetramethylene, pentamethylene, hexamethylene, propylene, ethylethylene, propylethylene, isopropylethylene, methylpentamethylene or the like, in which the preferable one is $C_1-C_4$ alkylene, and the most preferable one is methylene or ethylene.

Suitable "anion" may be halide anion such as chloride anion, bromide anion, fluoride anion, iodide anion, or the like.

Suitable pharmaceutically acceptable salts of the object compound [I] are conventional non-toxic salts and include an organic acid addition salt [e.g. formate, acetate, trifluoroacetate, maleate, tartarate, fumarate, methanesulfonate, benzenesulfonate, toluenesulfonate, etc.], an inorganic acid addition salt [e.g. hydrochloride, hydrobromide, sulfate, phosphate, etc.], a salt with an acidic amino acid [e.g. aspartic acid salt, glutamic acid salt, etc.], and the like.

In case that the object compound [I] has an acidic group, such as a carboxy group, within its molecule, there may be mentioned, as examples of the salt, salts with metals such as sodium, potassium, calcium, magnesium and the like and salts with organic bases such as triethylamine, dicyclohexylamine and the like as well as the internal salt.

With respect to the salts of the compound [Ia] to [In] in the Processes 1 to 13, it is to be noted that these compounds are included within the scope of the compound [I], and accordingly the suitable examples of the salts of these compounds are to be referred to those as exemplified for the object compound [I].

The processes for preparing the object compounds [I] of the present invention are explained in detail in the following.

Process 1

The object compound [Ia] or its salt can be prepared by subjecting a compound [II] or its salt to cyclization reaction.

Suitable salts of the compound [II] may be the same as those exemplified for the compound [I].

This cyclization reaction is carried out in the presence of a cyclizing agent.

Suitable examples of the cyclizing agent to be used in this reaction may be halogen [e.g. bromine, chlorine, iodine, etc.], thionyl halide [e.g. thionyl chloride, thionyl bromide, etc.], sulfuryl halide [e.g. sulfuryl chloride, sulfuryl bromide, etc.] or the like.

This reaction is usually carried out in a conventional solvent which does not adversely influence the reaction such as methylene chloride, dichloroethane, chloroform, carbon tetrachloride, acetic acid, propionic acid or a mixture thereof.

In case that the above-mentioned cyclizing agent is liquid, it can be also used as a solvent.

The reaction temperature is not critical, and the reaction is usually carried out at ambient temperature or under warming or heating.

Process 2

The object compound [Ib] or its salt can be prepared by subjecting a compound [III] or its salt to cyclization reaction.

Suitable salts of the compound [III] may be the same as those exemplified for the compound [I].

This cyclization reaction is carried out in the presence of a dehydrating agent.

Suitable dehydrating agents used of this reaction may include conventional organic or inorganic ones such as an inorganic halogen compound [e,g. thionyl chloride, phosphorus pentachloride, phosphorus oxychloride, phosphorus tribromide, stannic chloride, titanium tetrachloride, etc.]; sulfonyl halide [e.g. mesyl chloride, tosyl chloride, benzenesulfonyl chloride, etc.]; carbodiimide compound [e.g. N,N'-dicyclohexylcarbodiimide, N-cyclohexyl-N'-morpholinoethylcarbodiimide, N-ethyl-N'-(3-dimethylaminopropyl)carbodiimide, etc.]; other phosphorus compound [e.g. phosphorus pentoxide, polyphosphate ester, etc.]; a combination of phosphine compound [e.g. triethylphosphine, triphenylphosphine, etc.] and azodicarboxylate ester compound [e.g. diethyl azodicarboxylate, diisopropyl azodicarboxylate, etc.]; and the like or an optional mixture thereof.

This reaction is usually carried out in a conventional solvent such as diethyl ether, N,N-dimethylformamide, pyridine, acetic acid, formic acid, benzene, carbon tetrachloride, chloroform, methylene chloride, tetrahydrofuran, dioxane, sulfolane, and the like. Additionally in case that the above-mentioned dehydrating agents are in liquid, they can also be used as a solvent.

The reaction temperature is not critical, and the reaction is usually carried out under cooling to under heating.

Process 3

The object compound [Ic] or its salt can be prepared by reacting a compound [IVa] or its salt with a compound [V] or its salt.

Suitable salts of the compounds [IVa] and [V] may be the same as those exemplified for the compound [I].

In this reaction, imino group of the compound [V] is usually activated by reacting the compound [V] with an activating agent [e.g methyl chloroformate, etc.].

This reaction is usually carried out in a conventional solvent such as water, alcohol [e.g. methanol, ethanol, propanol, etc.], tetrahydrofuran, dioxane, chloroform, methylene chloride, acetic acid, N,N-dimethylformamide, dimethylsulfoxide, etc. or a mixture thereof.

The reaction temperature is not critical, and the reaction is usually carried out under cooling, at ambient temperature, under warming or under heating.

Process 4

The object compound [Id] or its salt can be prepared by reacting a compound [IVb] or its salt with cyanogen halide.

Suitable salts of the compound [IVb] may be the same as those exemplified for the compound [I].

Suitable cyanogen halides are cyanogen bromide, cyanogen chloride and cyanogen iodide.

The reaction is usually carried out in a solvent such as water, alcohol [e.g. methanol, ethanol, propanol, etc.], tetrahydrofuran, dioxane, chloroform, methylene chloride, diethyl ether, etc. or a mixture thereof.

The reaction temperature is not critical, and the reaction is usually carried out under cooling, at ambient temperature, under warming or under heating.

Process 5

The object compound [Ie] or its salt can be prepared by subjecting a compound [VI] or its salt to cyclization reaction.

Suitable salts of the compound [VI] may be the same as those exemplified for the compound [I].

This reaction can be carried out in substantially the same manner as Process 2, and therefore the reaction mode and reaction conditions [e.g. dehydrating agent, solvent, reaction temperature, etc.] of this reaction are to be referred to those as explained in Process 2.

Process 6

The object compound [If] or its salt can be prepared by reacting a compound [VII] or its salt with ammonium thiocyanate.

Suitable salts of the compound [VII] may be the same as those exemplified for the compound [I].

This reaction is carried out in the presence of a cyclizing agent.

Suitable examples of the cyclizing agent to be used in this reaction may be halogen [e.g. bromine chlorine, iodine, etc.], thionyl halide [e.g. thionyl chloride, thionyl bromide, etc.], sulfuryl halide [e.g. sulfuryl chloride, sulfuryl bromide, etc.] or the like.

This reaction is usually carried out in a conventional solvent which does not adversely influence the reaction such as methylene chloride, dichloroethane, chloroform, carbon tetrachloride, acetic acid, propionic acid or a mixture thereof.

In case that the above-mentioned cyclizing agent is liquid, it can be also used as a solvent.

The reaction temperature is not critical, and the reaction is usually carried out at ambient temperature or under warming or heating.

Process 7

The object compound [Ig] or its salt can be prepared by reacting a compound [IVc] or its salt with a compound [VIII].

Suitable salts of the compound [IVc] may be the same as those exemplified for the compound [I].

This reaction is usually carried out in a conventional solvent such as water, alcohol [e.g. methanol, ethanol, propanol, etc.], tetrahydrofuran, dioxane, chloroform, methylene chloride, N,N-dimethylformamide, dimethyl sulfoxide, etc. or a mixture thereof.

The reaction temperature is not critical, and the reaction is usually carried out at ambient temperature or under warming or heating.

Process 8

The object compound [Ih] or its salt can be prepared by reacting a compound [IVc] or its salt with a compound [IX] or its salt.

Suitable salts of the compound [IVc] may be the same as those exemplified for the compound [I].

Suitable salts of the compound [IX] may be alkali metal salt [e.g. lithium salt, sodium salt, potassium salt, etc.], or the like.

This reaction is usually carried out in a conventional solvent such as water, an alcohol [e.g. methanol, ethanol, isopropyl alcohol, etc.], dioxane, tetrahydrofuran, N,N-dimethylformamide, or any other organic solvent which does not adversely affect this reaction, or a mixture thereof.

The reaction temperature is not critical and the reaction is usually carried out at ambient temperature, under warming or under heating.

Process 9

The object compound [Ij] or its salt can be prepared by reducing a compound [Ii] or its salt.

The reduction can be carried out in a conventional manner, namely, catalytic reduction.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt,etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, etc. or a mixture thereof.

The reaction is usually carried out under cooling to warming or heating.

In case that A is lower alkenylene, it may be also reduced to lower alkylene. Such case is also included within the scope of this process.

Process 10

The object compound [Ik] or its salt can be prepared by reacting a compound [Xa] or its salt with a compound [XIa] or its salt.

Suitable salts of the compounds [Xa] and [XIa] may be the same as those exemplified for the compound [I].

This reaction is so-called Wittig reaction, and the reaction mode and reaction conditions can be referred to those of the conventional Wittig reaction.

Process 11

The object compound [Il] or its salt can be prepared by reducing a compound [Ik] or its salt.

This reaction can be carried out in substantially the same manner as Process 9, and therefore the reaction mode and reaction conditions [e.g. catalyst, solvent, reaction temperature, etc.] of this reaction are to be referred to those as explained in Process 9.

In case that $R^1$ is imidazopyridyl, it may be also reduced to tetrahydroimidazopyridyl. Such case is also included within the scope of this process.

Process 12

The object compound [Im] or its salt can be prepared by reacting a compound [Xb] or its salt with a compound [XIb] or its salt.

Suitable salts of the compounds [Xb] and [XIb] may be the same as those exemplified for the compound [I].

This reaction is usually carried out in a conventional solvent such as water, an alcohol [e.g. methanol, ethanol, isopropyl alcohol, etc.], dioxane, tetrahydrofuran, acetone, N,N-dimethylformamide, or any other organic solvent which does not adversely affect this reaction, or a mixture thereof.

This reaction is preferably carried out in the presence of a base, for example, an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate.

The reaction temperature is not critical and the reaction is usually carried out under cooling, at ambient temperature, under warming or under heating.

Process 13

The object compound [In] or its salt can be prepared by reacting a compound [Xc] or its salt with a compound [XIc] or its salt.

Suitable salts of the compounds [Xc] and [XIc] may be the same as those exemplified for the compound [I].

This reaction can be carried out in substantially the same manner as Process 12, and therefore the reaction mode and reaction conditions [e.g. solvent, reaction temperature, etc.] of this reaction are to be referred to those as explained in Process 12.

Among the starting compounds [II], [III], [IV] and [VI], some of them are new and such compounds can be prepared by processes as illustrated in the following reaction schemes.

Process A

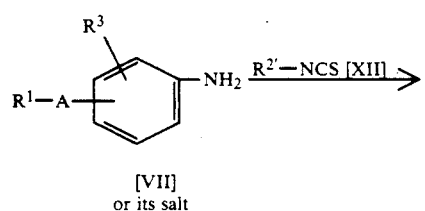

[VII]
or its salt

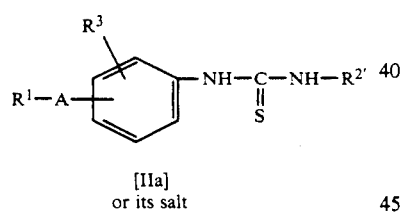

[IIa]
or its salt

Process B

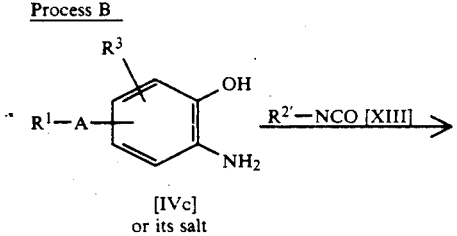

[IVc]
or its salt

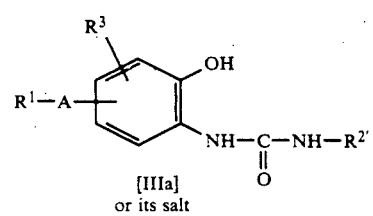

[IIIa]
or its salt

Process C

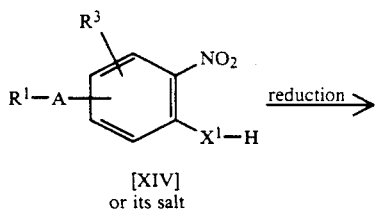

[XIV]
or its salt

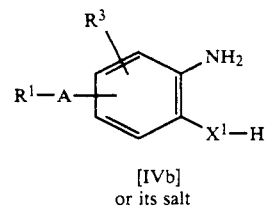

[IVb]
or its salt

Process D

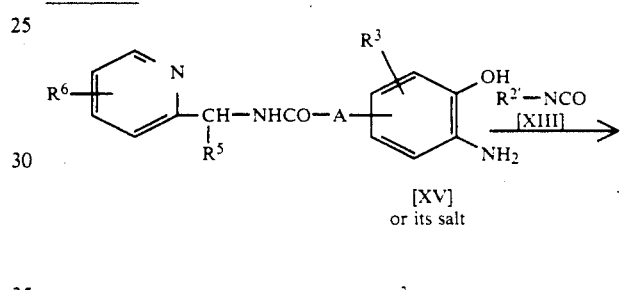

[XV]
or its salt

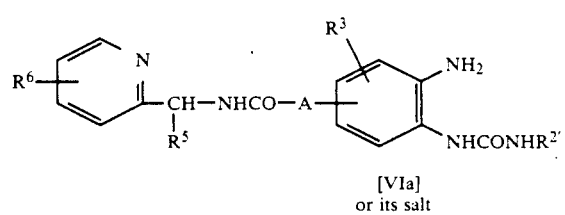

[VIa]
or its salt

Process E

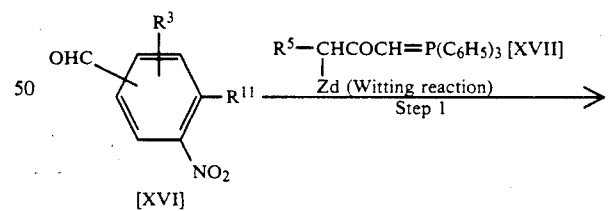

[XVI]

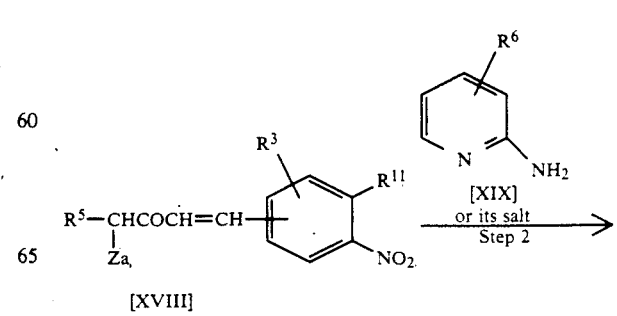

[XVIII]

15

-continued

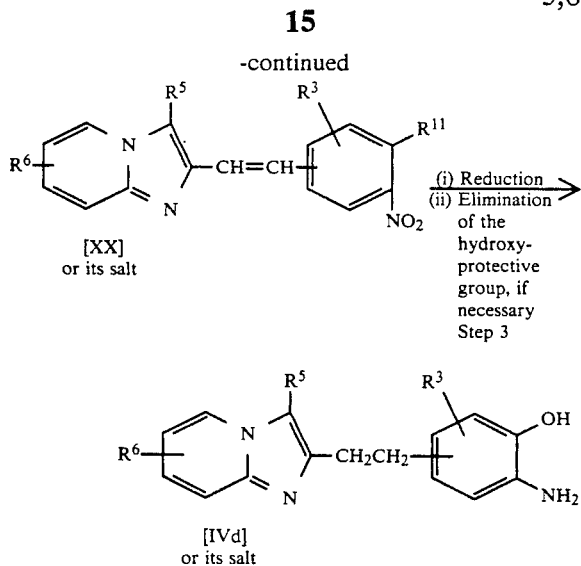

[XX] or its salt (i) Reduction
(ii) Elimination of the hydroxy-protective group, if necessary
Step 3

[IVd] or its salt wherein
R[11] is protected hydroxy,
Zd is halogen,
$R^1$, $R^2$, $R^3$, $R^5$, $R^6$, A and $X^1$ are each as defined above.

Suitable "protected hydroxy" may be substituted or unsubstituted lower alkoxy [e.g. tert-butoxy, methoxyethoxymethoxy, etc.], substituted or unsubstituted ar(-lower)alkoxy [e.g. benzyloxy, nitrobenzyloxy, etc.], acyloxy such as lower alkanoyloxy [e.g. formyloxy, acetyloxy, propionyloxy, etc.], sulfonyloxy [e.g. mesyloxy, tosyloxy, benzenesulfonyloxy, etc.], substituted or unsubstituted ar(lower)alkoxycarbonyloxy [e.g. benzyloxycarbonyloxy, bromobenzyloxycarbonyloxy, etc.] etc., tri(lower)alkylsilyloxy [e.g. trimethylsilyloxy, etc.] or the like.

The processes for preparing the starting compounds are explained in detail in the following.

Process A

The compound [IIa] or its salt can be prepared by reacting a compound [VII] or its salt with a compound [XII].

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process B

The compound [IIIa] or its salt can be prepared by reacting a compound [IVc] or its salt with a compound [XIII].

This reaction can be carried out in substantially the same manner as Process A, and therefore the reaction mode and reaction conditions [e.g. solvent, reaction temperature, etc.] of this reaction are to be referred to those as explained in Process A.

Process C

The compound [IVb] or its salt can be prepared by reducing a compound [XIV] or its salt.

Suitable salts of the compound [XIV] may be the same as those exemplified for the compound [I].

16

The reaction can be carried out in a conventional manner, namely, chemical reduction or catalytic reduction.

Suitable reducing agents to be used in chemical reduction are a combination of metal [e.g. tin, zinc, iron, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction may be the same as those exemplified in Process 9.

The reaction of this process is usually carried out in a solvent such as water, alcohol [e.g. methanol, ethanol, propanol, etc.], acetic acid, diethyl ether, dioxane, tetrahydrofuran, etc. or a mixture thereof.

The reaction is preferably carried out under somewhat milder conditions such as under cooling to warming.

Process D

The compound [VIa] or its salt can be prepared by reacting a compounds [XV] or its salt with a compound [XIII].

Suitable salts of the compounds [VIa] and [XV] may be the same as those exemplified for the compound [I].

This reaction can be carried out in substantially the same manner as Process A, and therefore the reaction mode and reaction conditions [e.g. solvent, reaction temperature, etc.] of this reaction are to be referred to those as explained in Process A.

Process E

Step 1

The compound [XVIII] can be prepared by reacting a compound [XVI] with a compound [XVII].

This reaction is so-called Wittig reaction, and the reaction mode and reaction conditions can be referred to those of the conventional Wittig reaction.

Step 2

The compound [XX] or its salt can be prepared by reacting a compound [XVIII] with a compound [XIX] or its salt.

Suitable salts of the compounds [XIX] and [XX] may be the same as those exemplified for the compound [I].

This reaction is usually carried out in a conventional solvent such as water, methanol, ethanol, isopropyl alcohol, tetrahydrofuran, acetonitrile, 1,2-dimethoxyethane, methylene chloride, chloroform, N,N-dimethylacetamide, N,N-dimethylformamide, dimethylsulfoxide, or any other organic solvent which does not adversely influence the reaction.

This reaction is preferably conducted in the presence of a base such as alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium ticarbonate, potassium bicarbonate, etc.], alkali metal alkoxide [e.g. sodium methoxide, sodium ethoxide, potassium tert-butoxide, etc.] or the like.

The reaction temperature is not critical, and the reaction is usually carried out at ambient temperature or under warming or heating.

Step 3

The compound [IVd] or its salt can be prepared by reducing a compound [XX] or its salt, and if necessary, eliminating the hydroxy-protective group.

Suitable salts of the compound [IVd] may be the same as those exemplified for the compound [I].

This reaction can be carried out in substantially the same manner as Process 9, and therefore the reaction mode and reaction conditions [e.g. catalyst, solvent, reaction temperature, etc.] of this reaction are to be referred to those as explained in Process 9.

In this reaction condition, some of hydroxy-protective group [e.g. benzyl, etc.] is simultaneously eliminated. In case that hydroxy-protective group which can not be eliminated by reduction, the compound [IVd] can be prepared by further eliminating the hydroxy-protective group of the reaction product obtained by reducing the compound [XX]. This elimination reaction can be carried out in a conventional manner, namely, hydrolysis.

Each of the compounds [XVIII] and [XX] obtained by the above-mentioned steps can be used as a starting compound in next step with or without its isolation and/or purification.

The compounds obtained by the above Processes 1 to 13 and A to E can be isolated and purified by a conventional method such as pulverization, recrystallization, column chromatography, repreicipitation or the like.

Preparations of the object compound [I] and starting compounds are not limited to the above-mentioned processes and, for example, said compounds can be prepared by the methods of Preparations and Examples mentioned below and by any process known in the art for preparing structurally analogous compounds thereto.

It is to be noted that each of the object compound [I] and the starting compounds may include one or more stereoisomer due to asymmetric carbon atom(s) and/or carbon-carbon double bond (i.e. Z-isomer and E-isomer), and all such isomers and mixture thereof are included within the scope of this invention.

The new benzazole compound [I] and pharmaceutically acceptable salts thereof possess antiulcer activity and $H_2$-receptor antagonism, and are useful for a therapeutic treatment of gastritis, ulcer [e.g. gastric ulcer, duodenal ulcer, anastomotic ulcer, etc.], Zollinger-Ellison syndrome, reflux esophagitis, upper gastrointestinal bleeding, and the like.

For thereapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating ulcer. In general, amounts between 0.1 mg/body and about 1,000 mg/body may be administered per day.

In order to illustrate the usefulness of the object compound [I], the pharmacological test data of some representative compounds of the compound [I] are shown in the following.

Test Compounds (a) 6-[(2-Pyridyl)methyl]-2-methylaminobenzothiazole
(b) 6-[2-(2-Pyridyl)ethyl]-2-ethylaminobenzothiazole
(c) 6-[2-(2-Pyridyl)ethyl]-2-aminobenzothiazole
(d) 6-[2-(7-Methylimidazo[1,2-a]pyridin-2-yl)ethyl-2-ethylaminobenzoxazole
(e) 6-[(2-Pyridyl)methyl]-2-aminobenzothiazole
(f) 6-[2-(3,7-Dimethylimidazo[1,2-a]pyridin-2-yl)ethyl]-2-methylaminobenzoxazole
(g) 6-[2-(3,7-Dimethylimidazo[1,2-a]pyridin-2-yl)ethyl]-2-aminobenzothiazole dihydrochloride
(h) 6-[2-(7-Methoxy-3-methylimidazo[1,2-a]pyridin-2-yl) ethyl]-2-aminobenzoxazole
(i) 6-[2-(3,7-Dimethylimidazo[1,2-a]pyridin-2-yl)ethyl]-2-aminobenzoxazole
(j) 6-[2-(3,7-Dimethylimidazo[1,2-a]pyridin-2-yl)ethyl]-2-ethylaminobenzoxazole
(k) 6-[2-(7-Methoxy-3-methylimidazo[1,2-a]pyridin-2-yl)ethyl]-2-methylaminobenzoxazole dihydrochloride
(l) 2-Ethylamino-6-[2-(7-methoxy-3-methylimidazo[1,2-a]pyridin-2-yl)ethyl]benzoxazole dihydrochloride Test A (Inhibition of stress ulcer)

Test Method

Five male Sprague-Dawley rats, aged 7 weeks and weighing about 200 g were used per group for the study on stress ulcer after the fast for 24 hours. Each animal was immobilized in a restrain cage and immersed to a level of the xiphoid in a water bath kept 22° C. Each of the test compound suspended in 0.1% methylcellulose solution was administered orally (5 ml/kg) just before the immobilization. Seven hours later, the animals were sacrificed and their stomachs were removed. The stomach was then fixed with 2% formalin. The area of ulcers was measured for each animal, and percentage of inhibition was calculated by comparing the mean area of ulcers ($mm^2$) in the test animals with that in the control animals.

Test Results

| Test Compound | Inhibition (%) (Dose:32 mg/kg) |
| --- | --- |
| (a) | 87.8 |
| (b) | 83.9 |
| (c) | 88.5 |
| (d) | 84.6 |
| (e) | 98.2 |
| (f) | 85.1 |
| (g) | 85.4 |
| (h) | 93.4 |
| (l) | 98.6 |

Test B ($H_2$-receptor antagonism in isolated guinea-pig atrium)

Test Method

The atrial strip isolated from guinea-pig was suspended under an initial tension 0.3 to 0.6 g in an organ bath containing Tyrode solution at 30° C., aerated 95%$O_2$-5%$CO_2$ gas. The beating rate and amplitude of contraction of the atrium were recorded by means of a transducer and a polygraph. Histamine (1×10 g/ml) was added to the bathing fluid and the increase in beating rate after dosing was measured. Addition of test compound was made 30 minutes after washing out histamine. Inhibitory effect of test compound was calculated by comparing histamine-induced increases in beating rate before and 30 minutes after dosing with test compound.

| Test Compound | Test Results Dose (g/ml) | $H_2$ Antagonism (%) |
|---|---|---|
| (h) | $3.2 \times 10^{-6}$ | 100 |
| (i) | $3.2 \times 10^{-6}$ | 93.1 |
| (j) | $3.2 \times 10^{-6}$ | 98.0 |
| (k) | $1.0 \times 10^{-6}$ | 92.5 |

The following Preparations and Examples are given for the purpose of illustrating the present invention in more detail.

Preparation 1

A mixture of 4-bromo-1-(4-nitrophenyl)but-1-en-3-one (5.7 g) and 2-amino-4-methylpyridine (6.8 g) in acetonitrile (50 ml) was stirred under reflux for 1.5 hours. The precipitate was collected by filtration and washed with acetonitrile to give 2-[2-(4-nitrophenyl)-vinyl]-7-methylimidazo[1,2-a]pyridine (3.29 g).

IR (Nujol): 1640, 1595, 1510, 1340 cm$^{-1}$
NMR ($CF_3CO_2D$, δ): 2.69 (3H, s), 7.23–7.52 (1H, m), 7.26 (1H, d, J=17 Hz), 7.53 (1H, d, J=17Hz), 7.54–7.91 (1H, m), 7.77 (2H, d, J=8 Hz), 8.00 (1H, s), 8.33 (2H, d, J=8 Hz), 8.42 (1H, d, J=7 Hz)

Preparation 2

A mixture of 3-chloro-2-butanone (200 g), pyridinium hydrobromide perbromide (690.4 g) and a solution of 25% hydrogen bromide in acetic acid (40 ml) in acetic acid was stirred at ambient temperature for 2 hours. The reaction mixture was added to a mixture of ethyl acetate (3 l) and water (3 l). To the separated organic layer was added water and the mixture was adjusted to pH 7 with sodium bicarbonate. The separated organic layer was washed with water and the solution was dried over magnesium sulfate. The solvent was evaporated and a residue was dissolved in tetrahydrofuran (300 ml). The solution was added to a solution of triphenylphosphine (443.1 g) in tetrahydrofuran (500 ml) and the mixture was stirred at ambient temperature for 2 hours. Decantation of the supernatant solvent gave residue, which was dissolved in methanol (200ml). To the solution was added a solution of water (1.5 l), ethyl acetate (1.5 l) and tetrahydrofuran (1 l) and the mixture was adjusted to pH 9.5 with potassium carbonate. The separated organic layer was washed with brine and dried over magnesium sulfate. The solvent was concentrated and the residue was triturated with diethyl ether. The precipitate was collected by filtration and dried to give 3-chloro-2-oxobutylidene triphenyl phosphorane (287.2 g).

mp: 121°–122° C.
IR (Nujol): 1558 cm$^{-1}$
NMR (DMSO-$d_6$, δ): 1.49–1.83 (3H, m), 3.77 and 4.24 (Total 1H, m), 4.30–4.94 (1H, m), 7.25–7.98 (15H, m)

Preparation 3

A mixture of 3-chloro-2-oxobutylidene triphenylphosphorane (100 g) and 3-benzyloxy-4-nitrobenzaldehyde (70.1 g) in tetrahydrofuran (800 ml) was refluxed for 2 hours. The solvent was evaporated in vacuo and the residue was dissolved in ethanol (800 ml). To the solution was added the 2-amino-4-picoline (73.7 g) and the mixture was refluxed for 2.5 hours. Evaporation of the solvent gave a residue, which was dissolved in a mixture of ethyl acetate (1 l) and water (1.5 l), and the mixture was adjusted to pH 1.0 with 6N hydrochloric acid under ice-cooling. The precipitate was collected by filtration. To the precipitate was added water (500 ml) and the mixture was adjusted to pH 8 with potassium carbonate. The aqueous mixture was extracted with a solution of tetrahydrofuran (500 ml) and ethyl acetate (600 ml) with salting-out technique. The extract was washed with brine and dried over magnesium sulfate. The solvent was evaporated and the residue was triturated with a solution of diisopropyl ether and diethyl ether (2:1, V/V). The precipitate was collected by filtration and dried to give 2-[2-(3-benzyloxy-4-nitrophenyl)vinyl]-3,7-dimethylimidazo[1,2-a]pyridine (28.3 g).

mp: 152°–154° C.
IR (Nujol): 1600, 1585 cm$^{-1}$
NMR (DMSO-$d_6$, δ): 2.37 (3H, s), 2.62 (3H, s), 5.45 (2H, s), 6.77 (1H, dd, J=2 Hz, 7 Hz), 7.22–7.83 (10H, m), 7.97 (1H, d, J=8 Hz), 8.13 (1H, d, J=7 Hz)

The following compounds (Preparations 4 to 6) were obtained according to a similar manner to that of Preparation 3.

Preparation 4

2[2-(4-Nitrophenyl)vinyl]-3,7-dimethylimidazo[1,2-a]pyridine mp: 207°–208° C.
NMR (DMSO-$d_6$, δ): 2.36 (3H, s), 2.57 (3H, s), 6.73 (1lH, dd, J=2 Hz, 7 Hz), 7.27 (1H, s), 7.52–7 69 (2H, m), 7.86 (2H, d, J=9 Hz), 8.00–8.20 (1H, m), 8.18 (2H, d, J=9 Hz)

Preparation 5

2[2-[2-(3-Benzyloxy-4-nitrophenyl)vinyl]-3-methylimidazo[1,2-a]pyridine mp: 151°–153° C.
IR (Nujol): 1600, 1585 cm$^{-1}$ Preparation 6

2-[2-(3-Benzyloxy-4-nitrophenyl)vinyl]-7-methoxy-3-methylimidazo[1,2-a]pyridine mp: 145°–147° C.
IR (Nujol): 1650, 1636, 1598, 1585 cm$^{-1}$
NMR (TFA, δ): 2.73 (3H, s), 4.12 (3H, s), 5.48 (2H, s), 7.04–7.55 (6H, m), 7.42 (5H, s), 8.10–8.37 (2H, m)

Preparation 7

A mixture of (chloroacetonyl)triphenylphosphonium chloride (190.7 g) and 2-amino-4-methylpyridine (158.9 g) in acetonitrile (1.3 l) was stirred under reflux for 5.5 hours. To the reaction mixture were added water (400 ml) and 3-benzyloxy-4-nitrobenzaldehyde (63.0 g) under ice-cooling. The mixture was adjusted to pH 9.5 with potassium carbonate and stirred for 2.5 hours at ambient temperature under keeping the pH 9.5 to 10.0 with 20% aqueous potassium carbonate. The reaction mixture was adjusted to pH 2.0 with conc. hydrochloric acid and the precipitate was collected by filtration. To a mixture of ethyl acetate, tetrahydrofuran and water was added the above obtained precipitate and the resultant mixture was adjusted to pH 7.0 with 20% aqueous potassium carbonate. The separated organic layer was washed with brine and dried over magnesium sulfate. The solvent was removed in vacuo to give 2-[2-(3-benzyloxy-4-nitrophenyl)vinyl]-7-methylimidazo[1,2-a]pyridine (43.14 g).

mp: 168°–171° C.
IR (Nujol): 1640, 1600, 1590 cm$^{-1}$
NMR (DMSO-$d_6$, δ): 2.34 (3H, s), 5.40 (2H, s), 6.69 (1H, dd, J=2 Hz, 7 Hz), 7.17–7.74 (10H, m), 7.89 (1H, d, J=8 Hz), 7.98 (1H, s), 8.37 (1H, d, J=7 Hz)

Preparation 8

2-[2-(4-Benzyloxy-3-nitrophenyl)vinyl]-7-methylimidazo[1,2-a]pyridine was obtained according to a similar manner to that of Preparation 7.

mp: 185°–189° C.
IR (Nujol): 1670, 1610, 1530, 1350 cm$^{-1}$

Preparation 9

To a solution of 4-(4-hydroxy-3-nitrophenyl)-2-butanone (17.5 g) in chloroform (150 ml) was dropwise added a sulfuryl chloride (11.2 g) at 20° to 27° C. under stirring and the mixture was stirred at ambient temperature for 7 hours. The reaction mixture was washed with brine and dried over magnesium sulfate. The solvent was evaporated in vacuo to give an oily residue of 4-(4-hydroxy-3-nitrophenyl)-3-chloro-2-butanone. To this oily residue was added a mixture of 2-amino-4-methylpyridine (22.6 g) in acetonitrile (150 ml) and the resultant mixture was refluxed for 8 hours under stirring. The precipitate was collected by filtration. The precipitate was dissolved in a mixture of ethyl acetate and 5% hydrochloric acid and separated aqueous layer was adjusted to pH 7.5 with aqueous 20% potassium carbonate. The resultant mixture was extracted with chloroform and the extract was washed with brine and dried over magnesium sulfate. The solvent was concentrated in vacuo and the crystalline residue was collected by filtration to give 3-(4-hydroxy-3-nitrobenzyl)-2,7-dimethylimidazo[1,2-a]pyridine (2.2 g).

mp: 268° C. (dec.)
IR (Nujol): 1650, 1620, 1585, 1530, 1500 cm$^{-1}$
NMR (DMSO-$d_6$, δ): 2.63 (3H, s), 2.66 (3H, s), 4.44 (2H, s), 7.24 (1H, d, J=9 Hz), 7.28 (1H, d, J=7 Hz), 7.53 (1H, dd, J=2 Hz, 9 Hz), 7.66 (1H, s), 7.99 (1H, d, J=2 Hz), 8.06 (1H, d, J=7 Hz)

Preparation 10

To a mixture of 3-benzyloxy-4-nitrocinnamic acid (12.9 g) and 2-(1-aminoethyl)-4-methylpyridine acetate (8.5 g) in N,N-dimethylformamide (150 ml) were added 1-hydroxybenzotraizole (7 g), N,N'-dicyclohexylcarbodiimide (10.65 g) and triethylamine (4.36 g), which was stirred at ambient temperature for 24 hours. After filtration, the filtrate was evaporated under reduced pressure. The residue was suspended in ethyl acetate (100 ml), which was filtered, and evaporated. The residue was subjected to column chromatography on silica gel to give 4-methyl-2-[1-(3-benzyloxy-4-nitrocinnamoylamino)ethyl]pyridine.

IR (Nujol): 1665, 1630, 1605, 1585 cm$^{-1}$
NMR (CDCl$_3$, δ): 1.52 (3H, d, J=7 Hz), 2.31 (3H, s), 5.15 (2H, s), 5.20 (1H, q, J=7 Hz), 6.53 (1H, d, J=15 Hz), 6.9–7.5 (3H, m), 7.09 (1H, s), 7.35 (5H, s), 7.46 (1H, d, J=15 Hz), 7.76 (1H, d, J=8 Hz), 8.03 (1H, d, J=6 Hz), 8.36 (1H, d, J=5 Hz)
Mass (m/e): 417 (M+)

Preparation 11

A solution of 2-[2-(3-benzyloxy-4-nitrophenyl)vinyl]-7-methylimidazo[1,2-a]pyridine in a mixture of methanol (300 ml) and tetrahydrofuran (300 ml) was hydrogenated over 10% palladium on carbon (5.0 g) under atmospheric pressure of hydrogen gas at ambient temperature. The catalyst was removed by filtration and the filtrate was evaporated in vacuo. The residue was triturated with diethyl ether to give a precipitate which was collected by filtration and dried to give 2-[2-(4-amino-3-hydroxyphenyl)ethyl]-7-methylimidazo[1,2-a]pyridine (20.67 g).

mp: 91°–97° C.
IR (Nujol): 1665, 1590 cm$^{-1}$
Mass (m/e): 267 (M+)

Preparation 12

2-[2-(3-Amino-4-hydroxyphenyl)ethyl]-7-methylimidazo[1,2-a]pyridine was obtained according to a similar manner to that of Preparation 11.

mp: 187°–191° C.
IR (Nujol): 1650, 1600 cm$^{-1}$
NMR (DMSO-$d_6$, δ): 2.34 (3H, s), 2.83 (4H, s), 6.12–6.76 (5H, m), 7.05–7.47 (2H, m), 7.51 (1H, s), 8.26 (1H, d, J=7 Hz)

Preparation 13

10% Palladium on carbon (10 g) was added to a mixture of 2-[2-(3-benzyloxy-4-nitrophenyl)vinyl]-3,7-dimethylimidazo[1,2-a]pyridine (27.3 g) in methanol (200 ml) and tetrahydrofuran (200 ml) and the mixture was stirred at ambient temperature under atmospheric pressure of hydrogen gas. The catalyst was removed by filtration and the filtrate was evaporated in vacuo. The residue was triturated with ethyl acetate and the precipitate was collected by filtration to give 2-[2-(4-amino-3-hydroxyphenyl)ethyl]-3,7-dimethylimidazo[1,2-a]pyridine (13.8 ).

mp: 153°–156° C.
IR (Nujol): 3450, 3440, 1645, 1620, 1590 cm$^{-1}$
NMR (DMSO-$d_6$, δ): 2.21 (3H, s), 2.30 (3H, s), 2.74 (4H, s), 6.32 (1H, dd, J=2 Hz, 8 Hz), 6.46 (1H, d, J=8 Hz), 6.47 (1H, d, J=2 Hz), 6.61 (1H, dd, J=2 Hz, 7 Hz), 7.14 (1H, s), 7.91 (1H, d, J=7 Hz)

The following compounds (Preparations 14 to 16) were obtained according to a similar manner to that of Preparation 13.

Preparation 14

2-[2-(4-Aminophenyl)ethyl]-3,7-dimethylimidazo[1,2-a]pyridine mp: 79°–80° C.
IR (Nujol): 3350, 3200, 1645, 1615, 1580 cm$^{-1}$
NMR (DMSO-$d_6$, δ): 2.21 (3H, s), 2.33 (3H, s), 2.80 (4H, s), 6.47 (2H, d, J=8 Hz), 6.68 (1H, dd, J=2 Hz, 7 Hz), 6.84 (2H, d, J=8 Hz), 7.22 (1H, s), 7.98 (1H, d, J=7 Hz)

Preparation 15

2-[2-(4-Amino-3-hydroxyphenyl)ethyl]-7-methoxy-3-methylimidazo[1,2-a]pyridine mp: 215°–217° C.
IR (Nujol): 1650, 1615, 1585 cm$^{-1}$ NMR (D$_2$O-DCl, δ): 2.22 (3H, s), 2.81-3.36 (4H, m), 4.06 (3H, s), 6.70-7.09 (2H, m), 7.00-7.46 (3H, m), 8.21 (1H, d, J=7 Hz)

Preparation 16

2-[2-(4-Amino-3-hydroxyphenyl)ethyl]-3-methylimidazo[1,2-a]pyridine mp: 152°-157° C.

IR (Nujol): 3470, 3270, 1615, 1590 cm$^{-1}$

NMR (DMSO-d$_6$, δ): 2.28 (3H, s), 2.81 (4H, m), 6.35-6.64 (2H, m), 6.67-7.32 (3H, m), 7.49 (1H, dd, J=2 Hz, 9 Hz), 8.07-8.25 (1H, m)

Preparation 17

A mixture of 3-(4-hydroxy-3-nitrobenzyl)-2,7-dimethylimidazo[1,2-a]pyridine (2.2 g) in ethanol (100 ml) and tetrahydrofuran (50 ml) was hydrogenated over 10% palladium on carbon (0.7 g) under atmospheric pressure of hydrogen gas for 5 hours at ambient temperature. The catalyst was removed by filtration and filtrate was concentrated in vacuo and the precipitate was collected by filtration to give 3-(3-amino-4-hydroxybenzyl)-2,7-dimethylimidazo[1,2-a]pyridine (1.4 g).

mp: 257°-259° C. (dec.)

IR (Nujol): 1650, 1620, 1590, 1525, 1505 cm$^{-1}$

NMR (DMSO-d$_6$, δ): 2.27 (3H, s), 2.33 (3H, s), 4.00 (2H, s), 6.20 (1H, dd, J=2 Hz, 7 Hz), 6.27-6.77 (3H, m), 7.20 (1H, s), 7.83 (1H, d, J=7 Hz)

Mass (m/e): 267 (M$^+$)

Preparation 18

A mixture of 4-methyl-2-[1-[3-benzyloxy-4-nitrocinnamoylamino)ethyl]pyridine (12.5 g) and 10% palladium on carbon (2 g) in a mixture of methanol (250 ml) and tetrahydrofuran (100 ml) was hydrogenated under one atmospheric pressure of hydrogen gas at ambient temperature for 4 hours. Insoluble material was filtered off, and the filtrate was evaporated in vacuo to give 4-methyl-2-[1-{3-(4-amino-3-hydroxyphenyl)propionamido}ethyl]pyridine (8.95 g).

IR (Nujol): 3250, 1660, 1605, 1530 cm$^{-1}$

NMR (CDCl$_3$, δ): 1.34 (3H, t, J=7 Hz), 2.66 (3H, s), 2.2-2.8 (4H, m), 4.95 (1H, q, J=7 Hz), 5.6 (2H, br s), 6.3-6.7 (2H, m), 7.6 (1H, s), 6.8-7.2 (1H, m), 7.3-7.6 (2H, m), 7.96 (1H, s), 8.28 (1H, d, J=5 Hz)

Preparation 19

A mixture of 4-nitrobenzaldehyde (30.2 g) and 2,3-lutidine (42.8 g) in acetic anhydride (100 ml) was refluxed for 9.5 hours under stirring. After cooling the reaction mixture, the precipitate was collected by filtration. The residue was washed with diethyl ether to give 3-methyl-2-[2-(4-nitrophenyl)vinyl]pyridine (25.5 g).

mp: 147°-150° C.

IR (Nujol): 1595, 1515 cm$^{-1}$

NMR (CF$_3$COOH, δ): 2.82 (3H, s), 7.50 (1H, d, J=17 Hz), 7.83 (2H, d, J=9 Hz), 7.63-8.07 (2H, m), 8.33-8.80 (2H, m), 8.30 (2H, d, J=9 Hz)

Preparation 20

5-Methyl-2-[2-(4-nitrophenyl)vinyl]pyridine was obtained according to a similar manner to that of Preparation 19.

mp: 179°-180° C.

IR (Nujol): 1595, 1565, 1515 cm$^{-1}$

NMR (CF$_3$COOH, δ): 2.73 (3H, s), 7.50 (1H, d, J=17 Hz), 7.90 (2H, d, J=9 Hz), 7.97 (1H, d, J=17 Hz), 7.67-8.67 (3H, m), 8.38 (2H, d, J=9 Hz)

Preparation 21

A mixture of 4-nitrobenzaldehyde (30.2 g) and 2,4-lutidine (64.2 g) in acetic anhydride (100 ml) was refluxed for 11 hours under stirring. The reaction mixture was evaporated in vacuo and the residue was dissolved in a mixture of ethyl acetate and water. The resultant solution was acidified to pH 0.8 with conc. hydrochloric acid and the mixture was stirred at ambient temperature for one hour. The precipitate was collected by filtration. The residue was suspended in a mixture of ethyl acetate, tetrahydrofuran and water and the resultant mixture was adjusted to pH 8.0 with aqueous 20% potassium carbonate. The separated organic layer was washed with brine and dried over magnesium sulfate. The solvent was evaporated in vacuo and the residue was subjected to column chromatography on silica gel. The fraction eluted with a mixture of ethyl acetate and diisopropyl ether (4:6 V/V) was collected and the solvent was evaporated in vacuo to give 4-methyl-2-[2-(4-nitrophenyl)vinyl]pyridine (22.1 g).

mp: 151°-152° C.

IR (Nujol): 1600, 1585, 1510 cm$^{-1}$

Preparation 22

A solution of 2-amino-4-methylpyrimidine (32.74 g) in acetic anhydride (150 ml) was refluxed for one hour under stirring. To the above solution was added 4-nitrobenzaldehyde (49.8 g) and the resultant mixture was refluxed for 7 hours under stirring. The reaction mixture was cooled and the precipitate was collected by filtlation. The residue was washed with diethyl ether to give 2-acetamido-4-[2-(4-nitrophenyl)vinyl]pyrimidine (72.7 g).

mp: 271°-272° C.

IR (Nujol): 1690, 1590, 1560, 1515, 1340 cm$^{-1}$

NMR (CF$_3$COOH, δ): 2.62 (3H, s), 7.43 (1H, d, J=16 Hz), 7.72 (1H, d, J=6 Hz), 7.92 (2H, d, J=9 Hz), 8.40 (1H, d, J=16 Hz), 8.43 (2H, d, J=9 Hz), 8.70 (1H, d, J=6 Hz)

Mass (m/e): 285 (M$^+$)

Preparation 23

A mixture of 3-methyl-2-[2-(4-nitrophenyl)vinyl]pyridine (13.0 g) in ethanol (250 ml), tetrahydrofuran 250 ml) and acetic acid (13 ml) was hydrogenated over 10% palladium on carbon (3 g) under atmospheric pressure of hydrogen gas for 7 hours at ambient temperature. The catalyst was removed by filtration and the filtrate was evaporated in vacuo. The residue was dissolved in a mixture of ethyl acetate and water and the resultant solution was adjusted to pH 7.0 with aqueous 20% potassium carbonate. The separated organic layer was washed with brine and dried over magnesium sulfate. The solvent was evaporated in vacuo and the residue was crystallized from diethyl ether and diisopropyl ether to give 3-methyl-2-[2-(4-aminophenyl)ethyl]pyridine (10.5 g).

mp: 46°-48° C.

IR (Nujol): 3450, 3320, 3200, 1635, 1615, 1590, 1520 cm$^{-1}$

NMR (DMSO-d$_6$, δ): 2.27 (3H, s), 2.90 (4H, s), 4.57 (2H, m), 6.50 (2H, d, J=9 Hz), 6.88 (2H, d, J=9 Hz), 7.02 (1H, d, J=8 Hz), 7.40 (1H, dd, J=2 Hz, 8 Hz), 8.32 (1H, d, J=2 Hz)

The following compounds (Preparations 24 to 26) were obtained according to a similar manner to that of Preparation 23.

Preparation 24

4-Methyl-2-[2-(4-aminophenyl)ethyl]pyridine

IR (film): 3450, 3350, 3200, 1610, 1565, 1520 cm$^{-1}$

NMR (DMSO-d$_6$, δ): 2.23 (3H, s), 2.87 (4H, s), 4.78 (2H, br s), 6.53 (2H, d, J=9 Hz), 6.80–7.10 (2H, m), 6.90 (2H, d, J=9 Hz), 8.33 (1H, d, J=5 Hz)

Preparation 25

5-Methyl-2-[2-(4-aminophenyl)ethyl]pyridine mp: 59°–61° C.

IR (Nujol): 1630, 1605, 1570, 1520 cm$^{-1}$

NMR (DMSO-d$_6$, δ): 2.27 (3H, s), 2.90 (4H, s), 4.57 (2H, m), 6.50 (2H, d, J=9 Hz), 6.88 (2H, d, J=9 Hz), 7.02 (1H, d, J=8 Hz), 7.42 (1H, dd, J=2 Hz, 8 Hz), 8.32 (1H, d, J=2 Hz)

Preparation 26

2-[2-(4-Amino-3-methoxyphenyl)ethyl]pyridine

IR (film): 3470, 3350, 3200, 1625, 1595, 1575, 1520 cm$^{-1}$

NMR (DMSO-d$_6$, δ): 2.93 (4H, m), 3.70 (3H, s), 4.40 (2H, m), 6.47–6.73 (2H, m), 7.00–7.33 (2H, m), 7.46–7.87 (2H, m), 8.50 (1H, dd, J=2 Hz, 5 Hz)

Preparation 27

A solution of 3-methyl-2-[2-(4-aminophenyl)ethyl]pyridine (14.2 g) and acetic anhydride (13.65 g) in ethyl acetate (150 ml) was stirred at ambient temperature for 2 hours. The reaction mixture was washed with saturated sodium bicarbonate solution and brine successively and dried over magnesium sulfate. The solvent was evaporated in vacuo and the residue was recrystallized from a mixture of diethyl ether and ethyl acetate to give 3-methyl-2-[2-(4-acetamidophenyl)ethyl]pyridine (16.3 g).

mp: 90°–93° C.

(Nujol): 3250, 1695, 1610, 1590, 1540, 1515 cm$^{-1}$

NMR (DMSO-d$_6$, δ): 2.07 (3H s) 2.23 (3H, s), 2.93 (4H, s), 7.03 (1H, dd, J=5 Hz, 8 Hz), 7.08 (2H, d, J=8 Hz), 7.45 (1H, dd, J=2 Hz, 5 Hz), 7.47 (2H, d, J=8 Hz), 8.28 (1H, dd, J=2 Hz, 5 Hz), 9.75 (1H, s)

Preparation 28

2-[2-(4-Acetamidophenyl)ethyl]pyridine was obtained according to a similar manner to that of Preparation 27.

mp: 83°–85° C.

IR (Nujol): 3250, 1660, 1600, 1535, 1515 cm$^{-1}$

NMR (DMO-d$_6$, δ): 2.00 (3H, s), 2.93 (4H, s), 6.90–7.23 (4H, m), 7.23–7.73 (3H, m), 8.38 (1H, dd, J=2, 5Hz), 9.72 (1H, s)

Preparation 29

To a solution of fuming nitric acid (d.1.50) (80 ml) was portionwise added 3-methyl-2-[2-(4-acetamidophenyl)ethyl]pyridine (16.2 g) at −15° to 15° C. and the mixture was stirred at the same condition for 30 minutes. The resultant solution was poured into an ice-water and the solution was adjusted to pH 8.0 with 20% aqueous sodium hydroxide. The mixture was extracted with a mixture of ethyl acetate and tetrahydrofuran, and the extract was washed with brine and dried over magnesium sulfate. The solvent was evaporated in vacuo and the residue was recrystallized from a mixture of ethyl acetate and diethyl ether to give 3-methyl-2-[2-(4-acetamido-3-nitrophenyl)ethyl]pyridine (16.9 g).

mp: 127°–128° C.

IR (Nujol): 3370, 1710, 1625, 1580, 1525 cm$^{-1}$

NMR (DMO-d$_6$, δ): 2.10 (3H, s), 2.27 (3H, s), 3.10 (4H, s), 7.17 (1H, dd, J=5 Hz, 8 Hz), 7.47–7.70 (3H, m), 7.80 (1H, s), 8.35 (1H, dd, J=2 Hz, 5 Hz), 10.13 (1H, s)

Preparation 30

2-[2-(4-Acetamido-3-nitrophenyl)ethyl]pyridine was obtained according to a similar manner to that of Preparation 29.

mp: 103°–105° C.

IR (Nujol): 3400, 1700, 1625, 1580, 1540, 1510 cm$^{-1}$

NMR (DMO-d$_6$, δ): 2.08 (3H, s), 3.07 (4H, s), 7.03–7.40 (2H, m), 7.50–7.90 (4H, m), 8.50 (1H, dd, J=2 Hz, 5 Hz), 10.08 (1H, s)

Preparation 31

A mixture of 3-methyl-2-[2-(4-acetamido-3-nitrophenyl)ethyl]pyridine (12.0 g) in ethanol (100 ml) and 17% hydrochloric acid (100 ml) was heated at 80° to 85° C. for 6 hours. The reaction mixture was evaporated in vacuo and the residue was dissolved in water. The resultant solution was adjusted to pH 8.0 with aqueous 20% potassium carbonate and extracted with a mixture of ethyl acetate and tetrahydrofuran. The extract was washed with brine and dried over magnesium sulfate. The solvent was evaporated in vacuo and the residue was recrystallized from a mixture of ethyl acetate and diethyl ether to give 3-methyl-2-[2-(4-amino-3-nitrophenyl)ethyl]pyridine (9.3 g).

mp: 158°–160° C.

IR (Nujol): 3450, 1645, 1570, 1515 cm$^{-1}$

NMR (DMO-d$_6$, δ): 2.25 (3H, s), 2.95 (4H, s), 6.95 (1H, d, J=9 Hz), 6.93–7.60 (5H, m), 7.75 (1H, d, J=2 Hz), 8.30 (1H, dd, J=2 Hz, 5 Hz)

Preparation 32

2-[2-(4-Amino-3-nitrophenyl)ethyl]pyridine was obtained according to a similar manner to that of Preparation 31.

mp: 147°–150° C.

IR (Nujol): 3450, 1635, 1600, 1565, 1520 cm$^{-1}$

NMR (DMO-d$_6$, δ): 2.95 (4H, s), 6.87–7.53 (6H, m), 7.53–7.93 (2H, m), 8.53 (1H, dd, J=2 Hz, 5 Hz)

Preparation 33

A mixture of 2-acetamido-4-[2-(4-nitrophenyl)vinyl]pyrimidine (8.52 g) in ethanol (200 ml) and tetrahydrofuran (100 ml) was hydrogenated over 10% palladium on carbon (2 g) under atmospheric pressure of hydrogen gas for 6 hours at ambient temperature. The catalyst was removed by filtration and the filtrate was evaporated in vacuo to give a crystalline residue, which was recrystallized from a mixture of ethyl acetate and diisopropyl ether to give 2-acetamido-4-[2-(4-aminophenyl)ethyl]pyrimidine (7.0 g).

mp: 135°–138° C.

IR (Nujol): 3350, 1675, 1615, 1600, 1570, 1520 cm$^{-1}$

NMR (DMSO-d$_6$, δ): 2.20 (3H, s), 2.92 (4H, m), 3.33 (2H, br s), 6.97 (1H, d, J=6 Hz), 7.17 (4H, m), 8.42 (1H, d, J=6 Hz)

The following compounds (Preparations 34 to 37) were obtained according to a similar manner to that of Preparation 33.

Preparation 34

3-Methyl-2-[2-(3,4-diaminophenyl)ethyl]pyridine mp: 91°–93° C.

NMR (DMO-d$_6$, δ): 2.20 (3H, s), 2.60-3.05 (4H, m), 4.23 (4H, br s), 6.07-6.53 (3H, m), 7.00 (1H, dd, J=5 Hz, 8 Hz), 7.40 (1H, dd, J=2 Hz, 8 Hz), 8.27 (1H, dd, J=2 Hz, 5 Hz)

Preparation 35

2-[2-(3,4-Diaminophenyl)ethyl]pyridine mp 93°-95° C.
IR (Nujol): 3400, 3200, 1635, 1590, 1570, 1250 cm$^{-1}$
NMR (DMO-d$_6$, δ): 2.88 (4H, br s), 4.30 (4H, br s), 6.17-6.67 (3H, m), 7.03-7.36 (2H, m), 7.50-7.90 (1H, m), 8.50 (1H, dd, J=2 Hz, 5 Hz)

Preparation 36

2-[2-(3-Amino-4-hydroxyphenyl)ethyl]pyridine mp: 113°-115° C.
IR (Nujol): 3460, 3350, 1620, 1600, 1570, 1520 cm$^{-1}$
NMR (DMO-d$_6$, δ): 2.83 (4H, m), 6.22 (1H, dd, J=2 Hz, 8 Hz), 6.47 (1H, d, J=2 Hz), 6.55 (1H, d, J=8 Hz), 7.00-7.33 (2H, m), 7.33-7.80 (1H, m), 8.45 (1H, dd, J=2 Hz, 5 Hz)

Preparation 37

2-[2-(3-Amino-4-hydroxyphenyl)ethyl]pyridine

IR (film): 1610, 1585, 1515 cm$^{-1}$
NMR (DMO-d$_6$, δ): 2.78 (4H, m), 6.23 (1H, dd, J=2 Hz, 8 Hz), 6.52 (1H, d, J=2 Hz), 6.60 (1H, d, J=8 Hz), 7.32 (1H, dd, J=5 Hz, 7 Hz), 7.60 (1H, d t, J=2 Hz, 7 Hz), 8.42 (2H, m)

Preparation 38

A solution of 2-[2-(4-nitrophenyl)vinyl]-7-methylimidazo[1,2-a]pyridine (3.1 g) in a solution of methanol (100 ml) and tetrahydrofuran (100 ml) was hydrogenated over 10% palladium on carbon (1.0 g) under atmospheric pressure of hydrogen gas at ambient temperature for 3 hours. The catalyst was removed by filtration and the filtrate was evaporated in vacuo. The residue was triturated with n-hexane to give a precipitate, which was collected by filtration and dried to give 2-[2-(4-aminophenyl)ethyl]-7-methylimidazo[1,2-a]pyridine (2.59 g).

mp: 144°-148° C.
IR (Nujol): 1645, 1615 cm$^{-1}$
NMR (DMO-d$_6$, δ): 2.31 (3H, s), 2.83 (4H, s), 4.76 (2H, s), 6.47 (2H, d, J=8 Hz), 6.59 (1H, dd, J=2 Hz, 7 Hz), 6.86 (2H, d, J=8 Hz), 7.17 (1H, s), 7.48 (1H, s), 8.24 (1H, d, J=7 Hz)

Preparation 39

A solution of 2-[2-(4-aminophenyl)ethyl]pyridine (5.8 g) and methyl isothiocyanate (2.6 g) in ethanol (60 ml) was refluxed for one hour. The reaction mixture was evaporated in vacuo to give a crystalline residue, which was recrystallized from a mixture of ethyl acetate and diisopropyl ether to give 2-[2-{4-(3-methylthioureido)-phenyl}ethyl]pyridine (7.3 g).

mp: 126°-129° C.
IR (Nujol): 1565, 1555, 1520 cm$^{-1}$
NMR (DMO-d$_6$, δ): 2.92 (3H, d, J=6 Hz), 2.97 (4H, s), 7.00-7.40 (5H, m), 7.40-7.83 (2H, m), 8.43 (1H, dd, J=2 Hz, 5 Hz), 9.33 (1H, s)
Mass (m/e): 271 (M+)

The following compounds (Preparations 40 to 45) were obtained according to a similar manner to that of Preparation 39.

Preparation 40

2-[2-{4-(3-Ethylthioureido)phenyl}ethyl]pyridine mp 124°-126° C.
IR (Nujol): 3200, 1595, 1545, 1525 cm$^{-1}$
NMR (DMO-d$_6$, δ): 1.08 (3H, t, J=6 Hz), 3.00 (4H, s), 3.30-3.70 (2H, m), 7.10-7.42 (6H, m), 7.53-7.83 (2H, m), 8.52 (1H, dd, J=2 Hz, 4 Hz), 9.36 (1H, s)
Mass (m/e): 285 (M+)

Preparation 41

3-[2-{4-(3-Methylthioureido)phenyl}ethyl]pyridine mp: 146°-148° C.
IR (Nujol): 3150, 1590, 1555, 1535, 1505 cm$^{-1}$
NMR (DMO-d$_6$, δ): 2.87 (4H, s), 2.92 (1H, d, J=5 Hz), 6.93-7.70 (7H, m), 8.28 (1H, dd, J=2 Hz, 5 Hz), 8.33 (1H, d, J=2 Hz), 9.32 (1H, s)
Mass (m/e): 271 (M+)

Preparation 42

3-Methyl-2-[2-{4-(3-ethylthioureido)phenyl}ethyl]pyridine mp: 124°-126° C.
IR (Nujol): 3180, 1590, 1550, 1530 cm$^{-1}$
NMR (DMO-d$_6$, δ): 1.10 (3H, t, J=7 Hz), 2.23 (3H, s), 2.97 (4H, s), 3.25-4.17 (2H, m), 6.93-7.73 (7H, m), 8.30 (1H, dd, J=2 Hz, 5 Hz), 9.27 (1H, s)

Preparation 43

3-Methyl-2-[2-{4-(3-methylthioureido)phenyl}ethyl]pyridine mp 129°-130° C.
IR (Nujol): 3150, 1520 cm$^{-1}$
NMR (DMO-d$_6$, δ): 2.25 (3H, s), 2.95 (3H, d, J=5 Hz), 3.00 (3H, s), 7.00-7.77 (7H, m), 8.32 (1H, dd, J=2 Hz, 5 Hz), 9.38 (1H, s)

Preparation 44

2-[2-{2-(3-Ethylthioureido)phenyl}ethyl]pyridine mp: 118°-121° C.
IR (Nujol): 1600, 1575, 1540, 1520 cm$^{-1}$
NMR (DMO-d$_6$, δ): 1.07 (3H, t, J=7 Hz), 2.95 (4H, s), 3.25-3.72 (2H, m), 6.93-7.80 (8H, m), 8.42 (1H, dd, J=2 Hz, 5 Hz), 9.07 (1H, s)

Preparation 45

2-Acetamido-4-[2-{4-(3-methylthioureido)phenyl}ethyl]pyrimidine mp: 178°-181° C.
IR (Nujol): 3250, 1675, 1595, 1565, 1515 cm$^{-1}$
NMR (DMO-d$_6$, δ): 2.20 (3H, s), 2.90 (3H, d, J=6 Hz), 2.97 (4H, s), 7.01 (1H, d, J=6 Hz), 7.13 (2H, d, J=8 Hz), 7.25 (2H, d, J=8 Hz), 7.54 (1H, m), 8.45 (1H, d, J=6 Hz), 9.34 (1H, s), 10.33 (1H, s)
Mass (m/e): 329 (M+)

Preparation 46

A solution of 2-(4-aminobenzyl)pyridine (3.8 g) and methyl isothiocyanate (2.0 g) in ethanol (100 ml) was heated under reflux for 2 hours. Evaporation of the solvent gave a residue which was triturated with diethyl ether to give a precipitate. The precipitate was collected by filtration and dried to give 2-[4-(3-methylthioureido)benzyl]pyridine (4.11 g).
IR (Nujol): 3170, 1600 cm$^{-1}$ NMR (DMO-d$_6$, δ): 2.92 (3H, d, J=5 Hz), 4.03 (2H, s), 7.08–7.47 (6H, m), 7.51–7.90 (2H, m), 8.52 (1H, m), 9.43 (1H, s)

Preparation 47

3-[4-(3-Methylthioureido)benzyl]pyridine was obtained according to a similar manner to that of Preparation 46.

mp: 178°–180° C.
IR (Nujol): 3200 cm$^{-1}$

Preparation 48

A mixture of 2-[2-(4-aminophenyl)ethyl]-3,7-dimethylimidazo[1,2-a]pyridine (2.2 g) and ethyl isothiocyanate (0.8 ml) in ethanol (20 ml) was refluxed for 1.5 hours. The solvent was evaporated and the residue was triturated with diethyl ether. The precipitate was collected by filtration and dried to give 3,7-dimethyl-2-[2-{4-(3-ethylthioureido)phenyl}ethyl]imidazo[1,2-a]pyridine (2.42 g).

mp: 194°–198° C.
IR (Nujol): 3350, 1640 cm$^{-1}$
NMR (TFA, δ): 1.42 (3H, t, J=7 Hz), 2.43 (3H, s), 2.66 (3H, s), 3.64 (4H, s), 3.48–3.88 (2H, m), 7.16–7.66 (5H, m), 7.64 (1H, s), 8.61 (1H, d, J=7 Hz)

Preparation 49

A solution of 2-[2-(3-amino-4-hydroxyphenyl)ethyl]pyridine (3.2 g) and ethyl isocyanate (1.58 g) in ethanol (80 ml) was stirred at 35° to 40° C. for 2 hours. The reaction mixture was evaporated in vacuo and the residue was recrystallized from a mixture of ethyl acetate and diethyl ether to give 2-[2-{3-(3-ethylureido)-4-hydroxyphenyl}ethyl]pyridine (3.5 g).

mp: 130°–132° C. (dec.)
IR (Nujol): 3300, 1640, 1600, 1555 cm$^{-1}$
NMR (DMO-d$_6$, δ): 1.07 (3H, t, J=7 Hz), 2.88 (4H, br s), 2.93–3.50 (2H, m), 6.62–6.92 (3H, m), 7.00–7.37 (2H, m), 7.50–7.97 (2H, m), 9.57 (1H, s)
Mass (m/e): 285 (M$^+$)

Preparation 50

3-[2-{3-(3-Ethylureido)-4-hydroxyphenyl}ethyl]pyridine was obtained according to a similar manner to that of Preparation 49.

mp: 174°–175° C. (dec.)
IR (Nujol): 3300, 1630, 1560 cm$^{-1}$
NMR (DMO-d$_6$, δ): 1.05 (3H, t, J=7 Hz), 2.80 (4H, m), 2.95–3.42 (2H, m), 6.50–7.05 (3H, m), 7.17–8.00 (3H, m), 8.43 (2H, m), 9.70 (1H, m)
Mass (m/e): 285 (M$^+$)

Preparation 51

A solution of 2-[2-(4-amino-3-hydroxyphenyl)ethyl]pyridine (2.9 g) and ethyl isocyanate (1.0 ml) in a solution of methanol (10 ml) and tetrahydrofuran (30 ml) was heated under reflux for 45 minutes. Evaporation of the solvent gave a residue which was triturated with diethyl ether to give a precipitate. The precipitate (3-ethylureido)-3-hydroxyphenyl}ethyl]pyridine.

mp: 132°–135° C.
IR (Nujol): 3300, 1635, 1610 cm$^{-1}$
NMR (DMSO-d$_6$, δ): 1.03 (3H, t, J=7 Hz), 2.72–3.31 (6H, m), 6.50–6.90 (3H, m), 7.13–7.39 (2H, m), 7.53–7.83 (2H, m), 7.87 (1H, s), 8.55 (1H, dd, J=2 Hz, 5 Hz), 9.87 (1H, s)

Preparation 52

A solution of 2-[2-(4-amino-3-hydroxyphenyl)ethyl]-7-methylimidazo[1,2-a]pyridine (20.0 g) and ethyl isocyanate (7.7 ml) in a mixture of tetrahydrofuran (200 ml) and methanol (200 ml) was stirred for 2.5 hours at ambient temperature. Evaporation of the solvent gave a residue, which was triturated with ethyl acetate to give a precipitate. The precipitate was collected by filtration and dried to give 2-[2-{4-(3-ethylureido)-3-hydroxyphenyl}ethyl]-7-methylimidazo[1,2-a]pyridine (17.86 g).

IR (Nujol): 3300, 1645, 1610 cm$^{-1}$

Preparation 53

2-[2-{3-(3-Ethylureido)-4-hydroxyphenyl}ethyl]-7-methylimidazo[1,2-a]pyridine was obtained according to a similar manner to that of Preparation 52.

mp: 212°–219° C.
IR (Nujol): 3320, 1645, 1605 cm$^{-1}$

Preparation 54

A solution of 3-(3-amino-4-hydroxybenzyl)-2,7-dimethylimidazo[1,2-a]pyridine (3.1 g) and ethyl isocyanate (1.24 g) in ethanol (50 ml) and tetrahydrofuran (50 ml) was refluxed for 2.5 hours under stirring. The reaction mixture was concentrated in vacuo and the precipitate was collected by filtration to give 3-[3-(3-ethylureido)-4-hydroxybenzyl]-2,7-dimethylimidazo[1,2-a]pyridine (3.7 g).

mp: 190°–193° C. (dec.)
NMR (DMO-d$_6$, δ): 1.03 (3H, t, J=7 Hz), 2.33 (3H, s), 2.37 (3H, s), 2.83–3.30 (2H, m), 4.12 (2H, s), 6.38–7.00 (4H, m), 7.28 (1H, s), 7.70 (1H, d, J=2 Hz), 7.97 (1H, d, J=7 Hz)

Preparation 55

The mixture of 2-[2-(4-amino-3-hydroxyphenyl)ethyl]-3,7-dimethylimidazo[1,2-a]pyridine (2.5 g) and methyl isocyanate (0.6 ml) in tetrahydrofuran (25 ml) and methanol (2.5 ml) was stirred for 1 hour at ambient temperature. To the reaction mixture was added ethyl acetate (30 ml) and the precipitate was collected by filtration. The precipitate was washed with ethyl acetate and dried to give 3,7-dimethyl-2-[2-{3-hydroxy-4-(3-methylureido)phenyl}ethyl]imidazo[1,2-a]pyridine (2.92 g).

mp: 144°–149° C.
IR (Nujol): 3330, 1645, 1600 cm$^{-1}$
NMR (TFA, δ): 2.44 (3H, s), 2.65 (3H, s), 2.89–3.43 (4H, m), 3.07 (3H, s), 6.92 (1H, d, J=8 Hz), 6.99 (1H, s), 7.24 (1H, d, J=8 Hz), 7.38 (1H, d, J=7 Hz), 7.61 (1H, s), 8.20 (1H, d, J=7 Hz)

The following compounds (Preparations 56 to 59) were obtained according to a similar manner to that of Preparation 55.

Preparation 56

3,7-Dimethyl-2-[2-{4-(3-ethylureido)-3-hydroxyphenyl}ethyl]imidazo[1,2-a]pyridine mp: 188°–190° C.
IR (Nujol): 3310, 1650, 1600 cm$^{-1}$
NMR (DMSO-d$_6$, δ): 1.04 (3H, t, J=7 Hz), 2.22 (3H, s), 2.33 (3H, s), 2.75–3.39 (2H, m), 6.42–6.88 (4H, m), 7.23 (1H, s), 7.65 (1H, d, J=8 Hz), 7.79 (1H, s), 8.01 (1H, d, J=7 Hz), 9.81 (1H, br s)

Preparation 57

3,7-Dimethyl-2-[2-{3-hydroxy-4-(3-isopropylureido)-phenyl}ethyl]imidazo[1,2-a]pyridine mp: 197°–199° C.

IR (Nujol): 3390, 3280, 1650, 1610 cm$^{-1}$

NMR (TFA, δ): 1.33 (6H, d, J=6 Hz), 2.45 (3H, s), 2.65 (3H, s), 2.91-3.43 (4H, m), 3.99-4.40 (1H, m), 6.94 (1H, d, J=8 Hz), 7.02 (1H, s), 7.25 (1H, d, J=8 Hz), 7.39 (1H, d, J=7 Hz), 7.63 (1H, s), 8.23 (1H, d, J=7 Hz)

Preparation 58

2-[2-{4-(3-Ethylureido)-3-hydroxyphenyl}ethyl]-3-methylimidazo[1,2-a]pyridine mp: 177°-180° C.

IR (Nujol): 3310, 1690, 1660, 1600 cm$^{-1}$

NMR (TFA, δ): 1.31 (3H, t, J=7 Hz), 2.51 (3H, s), 3.22 (4H, m), 3.54 (2H, q, J=7 Hz), 6.94-7.72 (4H, m), 7.91-8.22 (2H, m), 8.37-8.58 (1H, m)

Preparation 59

1-[2-{4-(3-Allylureido)-3-hydroxyphenyl}ethyl]-3,7-dimethylimidazo[1,2-a]pyridine mp: 187°-189° C.

IR (Nujol): 3300, 1650, 1600 cm$^{-1}$

NMR (TFA, δ): 2.44 (3H, s), 2.65 (3H, s), 2.91-3.41 (4H, m), 3.97-4.20 (2H, m), 5.21-5.53 (2H, m), 5.70-6.23 (1H, m), 6.85-7.11 (2H, m), 7.27 (1H, d, J=8 Hz), 7.41 (1H, d, J=7 Hz), 7.62 (1H, s), 8.22 (1H, d, J=7 Hz)

EXAMPLE 1

To a solution of 2-[2-{4-(3-methylthioureido)phenyl}ethyl]pyridine (7.1 g) in chloroform (100 ml) was dropwise added a bromine (4.6 g) at ambient temperature under stirring and the mixture was stirred at the same temperature for one hour. Further, the resultant mixture was refluxed under stirring for hours. The reaction mixture was evaporated in vacuo and the residue was heated with 10% hydrochloric acid (100 ml) for one hour at 70° to 80° C. The resultant mixture was washed with ethyl acetate. The separated aqueous layer was adjusted to pH 7.5 with aqueous 20% potassium carbonate and extracted with ethyl acetate. The extract was washed with brine and dried over magnesium sulfate. The solvent was evaporated in vacuo and the residue was subjected to column chromatography on silica gel. The fraction eluted with a mixture of ethyl acetate and diisopropyl ether (6:4 V/V) was collected and solvent was evaporated in vacuo to give a crystalline residue of 6-[2-(2-pyridyl)ethyl]-2-methylaminobenzothiazole (1.0 g).

mp: 118°-120° C.

IR (Nujol): 1636, 1595 cm$^{-1}$

NMR (DMSO-d$_6$, δ): 2.94 (3H, J=6 Hz), 3.00 (4H, m), 7.05 (1H, dd, J=2 Hz, 8 Hz), 7.13-7.75 (2H, m), 7.30 (1H, d, J=8 Hz), 7.48 (1H, d, J=2 Hz), 7.63 (1H, dt, J=2 Hz, 7 Hz), 7.80 (1H, q, J=6 Hz), 8.48 (1H, m)

Mass (m/e): 269 (M$^+$)

The following compounds (Examples 2 to 6) were obtained according to a similar manner to that of Example 1.

EXAMPLE 2

6-[2-(3-Methyl-2-pyridyl)ethyl]-2-methylaminobenzothiazole mp: 100°-103° C.

IR (Nujol): 1625, 1595, 1560 cm$^{-1}$

NMR (DMSO-d$_6$, δ): 2.25 (3H, s), 2.97 (3H, d, J=5 Hz), 3.03 (4H, s), 6.93-7.33 (3H, m), 7.33-7.67 (2H, m), 7.78 (1H, m), 8.33 (1H, dd, J=2 Hz, 5 Hz)

Mass (m/e): 283 (M$^+$)

EXAMPLE 3

6-[2-(2-Pyridyl)ethyl]-2-ethylaminobenzothiazole mp: 102°-104° C.

IR (Nujol): 1610, 1585, 1555 cm$^{-1}$

NMR (DMSO-d$_6$, δ): 1.20 (3H, t, J=7 Hz), 3.03 (4H, m), 3.43 (2H, m), 7.00-8.07 (8H, m), 8.53 (1H, dd, J=2 Hz, 4 Hz)

Mass (m/e): 283 (M$^+$)

EXAMPLE 4

4-[2-(2-Pyridyl)ethyl]-2-ethylaminobenzothiazole mp: 106°-108° C.

IR (Nujol): 1650, 1605, 1570, 1555, 1515 cm$^{-1}$

NMR (DMSO-d$_6$, δ): 1.06 (3H, t, J=7 Hz), 2.98 (4H, s), 2.93-3.30 (2H, m), 6.45 (1H, t, J=5 Hz), 6.76-7.30 (4H, m), 7.50-7.83 (2H, m), 8.5 (1H, dd, J=2 Hz, 5 Hz)

Mass (m/e): 283 (M$^+$)

EXAMPLE 5

6-[2-(3-Pyridyl)ethyl]-2-methylaminobenzothiazole mp: 155°-157° C.

IR (Nujol): 1635, 1590, 1575 cm$^{-1}$

NMR (DMSO-d$_6$, δ): 2.91 (4H, m), 2.95 (3H, d, J=6 Hz), 7.04 (1H, dd, J=2 Hz, 8 Hz), 7.25 (1H, dd, J=5 Hz, 7 Hz), 7.30 (1H, d, J=8 Hz), 7.48 (1H, d, J=2 Hz), 7.60 (1H, dd, J=2 Hz, 7 Hz), 7.80 (1H, q, J=6 Hz), 8.37 (1H, dd, J=2 Hz, 5 Hz), 8.41 (1H, d, J=2 Hz)

EXAMPLE 6

6-[2-(3-Methyl-2-pyridyl)ethyl]-2-ethylaminobenzothiazole mp: 159°-161° C.

IR (Nujol): 1610, 1585, 1540 cm$^{-1}$

NMR (D$_2$O+DCl, δ): 1.42 (3H, t, J=8 Hz), 2.42 (3H, s), 2.97-3.43 (4H, m), 3.53 (2H, q, J=8 Hz), 7.30 (1H, s), 7.35 (1H, s), 7.55 (1H, s), 7.90 (1H, q, J=6 Hz), 8.40 (1H, d, J=6 Hz), 8.48 (1H, dd, J=2 Hz, 6 Hz)

Mass (m/e): 298 (M+1)

EXAMPLE 7

To a solution of 2-[4-(3-methylthioureido)benzyl]pyridine (4.0 g) in chloroform (80 ml) was dropwise added the solution of bromine (0.9 ml) in chloroform (5 ml) at ambient temperature and the mixture was heated under reflux for 2.5 hours. The reaction mixture was added to 10% hydrochloric acid (60 ml) and the mixture was heated under reflux for 20 minutes. To the separated aqueous layer was added a solution of ethyl acetate and tetrahydrofuran and the resultant solution was adjusted to pH 8 with potassium carbonate. The separated organic layer was washed with brine and dried over magnesium sulfate. The crude product obtained by concentration was purified by silica gel column chromatography eluting with a mixture of chloroform and ethyl acetate (4:1 V/V). The eluted fractions containing desired product were evaporated to give 6-[(2-pyridyl)methyl]-2-methylaminobenzothiazole (0.48 g).

mp: 118°-121° C.

IR (Nujol): 1635, 1590 cm$^{-1}$

NMR (DMSO-d$_6$, δ): 2.92 (3H, d, J=5 Hz), 4.07 (2H, s), 7.07-7.31 (2H, m), 7.09 (1H, dd, J=2 Hz, 8 Hz), 7.30 (1H, d, J=8 Hz), 7.53 (1H, d, J=2 Hz), 7.50-7.80 (1H, m), 7.78 (1H, q, J=5 Hz), 8.45 (1H, br. d, J=5 Hz)

Mass (m/e): 255 (M$^+$)

The following compounds (Examples 8 and 9) were obtained according to a similar manner to that of Example 7.

EXAMPLE 8

6-[(3-Pyridyl)methyl]-2-methylaminobenzothiazole mp: 169°-171° C.

IR (Nujol): 3200, 1610, 1589 cm$^{-1}$

NMR (DMSO-d$_6$, δ): 2.93 (3H, d, J=5 Hz), 3.96 (2H, s), 7.08 (1H, dd, J=2 Hz, 9 Hz), 7.26 (1H, dd, J=2 Hz, 5 Hz), 7.33 (1H, d, J=9 Hz), 7.43-7.66 (1H, m), 7.53 (1H, d, J=2 Hz), 7.80 (1H, m), 8.38 (1H, dd, J=2 Hz, 5 Hz), 8.49 (1H, d, J=2 Hz)

Mass (m/e): 255 (M+)

EXAMPLE 9

6-[(2-Pyridyl)methyl]-2-(3-ethylureido)benzothiazole mp: 184°-185° C.

IR (Nujol): 3300, 1670, 1610, 1580 cm$^{-1}$

NMR (DMSO-d$_6$, δ): 1.09 (3H, t, J=7 Hz), 2.96-3.45 (2H, m), 4.10 (2H, s), 6.70 (1H, t, J=5 Hz), 7.03-7.46 (3H, m), 7.49 (1H, d, J=8 Hz), 7.50-7.80 (1H, m), 7.73 (1H, s), 8.45 (1H, d, J=5 Hz), 10.55 (1H, br s)

Mass (m/e): 312 (M+)

EXAMPLE 10

To a solution of 2-acetamido-4-[2-{4-(3-methylthioureido)phenyl}ethyl]pyrimidine (5.8 g) in chloroform (100 ml) was dropwise added a solution of bromine (3.1 g) in chloroform (3 ml) at ambient temperature under stirring and the mixture was stirred at the same temperature for one hour. Further, the resultant mixture was refluxed for 2 hours with stirring. The reaction mixture was evaporated in vacuo and the residue was heated with 10% hydrochloric acid (100 ml) for one hour at 70° to 80° C. The resultant mixture was washed with ethyl acetate. The separated aqueous layer was adjusted to pH 8.0 with aqueous 20% potassium carbonate and extracted with ethyl acetate. The extract was washed with brine and dried over magnesium sulfate. The solvent was evaporated in vacuo and the residue was subjected to column chromatography on silica gel. The column was eluted with a mixture of ethyl acetate and tetrahydrofuran (9:1 V/V), and the fraction containing the desired product was evaporated in vacuo and the crystalline residue was washed with ethyl acetate to give 6-[2-(2-amino-4-pyrimidinyl)ethyl]-2-methylaminobenzothiazole (0.66 g).

mp: 259°-261° C. (dec.)

IR (Nujol): 1655, 1625, 1565 cm$^{-1}$

NMR (D$_2$O+DCl, δ): 3.11 (3H, s), 3.20 (4H, s), 7.05 (1H, d, J=6 Hz), 7.30 (2H, s), 7.57 (1H, s), 8.37 (1H, s)

Mass (m/e): 285 (M+)

EXAMPLE 11

A solution of bromine (0.33 ml) in chloroform (3 ml) was added to the mixture of 3,7-dimethyl-2-[2-{4-(3-ethylthioureido)phenyl}ethyl]imidazo[1,2-a]pyridine (2 g) in chloroform (40 ml) and the mixture was refluxed for 2 hours. The reaction mixture was added to a mixture of ethyl acetate and water and the mixture was adjusted to pH 8 with potassium carbonate. The separated organic layer was washed with brine and dried over magnesium sulfate. Evaporation of the solvent gave a residue, which was subjected to a column chromatography on silica gel eluting with a mixture of chloroform and methanol (19:1, V/V). The fractions containing desired product were combined and evaporated to give 6-[2-(3,7-dimethylimidazo[1,2-a]pyridin-2-yl)ethyl]-2-ethylaminobenzothiazole (0.41 g).

mp: 165°-166° C.

IR (Nujol): 3200, 1645, 1605, 1570 cm$^{-1}$

NMR (DMSO-d$_6$, δ): 1.18 (3H, t, J=7 Hz), 2.20 (3H, s), 2.31 (3H, s), 2.92 (4H, s), 3.12-3.54 (2H, m), 4.62 (1H, dd, J=2 Hz, 7 Hz), 6.96 (1H, dd, J=2 Hz, 8 Hz), 7.17 (1H, s), 7.22 (1H, d, J=8 Hz), 7.40 (1H, s), 7.80 (1H, t, J=5 Hz), 7.92 (1H, d, J=7 Hz)

EXAMPLE 12

A mixture of 2-[2-(4-aminophenyl)ethyl]pyridine (5.94 g) and ammonium thiocyanate (4.56 g) in acetic acid (50 ml) was stirred at ambient temperature for one hour. A solution of bromine (4.8 g) in acetic acid (5 ml) was dropwise added to the above mixture at 18° to 23° C. under stirring and the resultant mixture was stirred at ambient temperature for 3 hours. The reaction mixture was evaporated in vacuo and the residue was dissolved in a mixture of ethyl acetate and water. The solution was acidified to pH 1.0 with hydrochloric acid. The separated aqueous layer was adjusted to pH 7.5 with aqueous 20% potassium carbonate and extracted with a mixture of ethyl acetate and tetrahydrofuran. The extract was washed with brine and dried over magnesium sulfate. The solvent was evaporated in vacuo and the residue was recrystallized from ethyl acetate to give 6-[2-(2-pyridyl)ethyl]-2-aminobenzothiazole (4.8 g).

mp: 163°-165° C.

NMR (DMSO-d$_6$, δ): 3.00 (4H, s), 7.04 (1H, dd, J=2 Hz, 7 Hz), 7.10-7.40 (4H, m), 7.49 (1H, d, J=2 Hz), 7.49-7.78 (2H, m), 8.48 (1H, m)

Mass (m/e): 255 (M+)

The following compounds (Examples 13 to 20) were obtained according to a similar manner to that of Example 12.

EXAMPLE 13

6-[2-(3-Methyl-2-pyridyl)ethyl]-2-aminobenzothiazole mp: 194°-196° C.

IR (Nujol): 1665, 1605, 1560, 1545 cm$^{-1}$

NMR (D$_2$O+DCl, δ): 2.43 (3H, s), 2.93-3.57 (4H, m), 7.30 (2H, s), 7.48 (1H, s), 7.62 (1H, q, J=6 Hz), 8.37 (1H, dd, J=2 Hz, 6 Hz), 8.45 (1H, dd, J=2 Hz, 6 Hz)

Mass (m/e): 269 (M+)

EXAMPLE 14

6-[2-(5-Methyl-2-pyridyl)ethyl]-2-aminobenzothiazole mp: 208°-209° C.

IR (Nujol): 1660, 1605, 1565, 1540 cm$^{-1}$

NMR (D$_2$O+DCl, δ): 2.52 (3H, s), 3.00-3.53 (4H, m), 7.28 (2H, s), 7.47 (1H, s), 7.70 (1H, d, J=8 Hz), 8.25 (1H, dd, J=2 Hz, 8 Hz), 8.38 (1H, d, J=2 Hz)

Mass (m/e): 269 (M+)

EXAMPLE 15

6-[2-(4-Methyl-2-pyridyl)ethyl]-2-aminobenzothiazole mp: 188°-191° C.

IR (Nujol): 1640, 1610, 1565, 1535 cm$^{-1}$

NMR (D$_2$O+DCl, δ): 2.67 (3H, s), 3.27 (4H, m), 7.37 (2H, s), 7.53 (1H, d, J=2 Hz), 7.73 (1H, s), 7.77 (2H, dd, J=2 Hz, 6 Hz), 8.48 (1H, d, J=6 Hz)

Mass (m/e): 269 (M+)

EXAMPLE 16

6-[2-(2-Pyridyl)ethyl]-4-methoxy-2-aminobenzothiazole mp: 222°-223.5° C.

IR (Nujol): 1630, 1595, 1550 cm$^{-1}$
NMR (D$_2$O+DCl, δ): 3.00–3.66 (4H, m), 3.95 (3H, s), 6.86 (1H, s), 7.05 (1H, s), 7.80–8.20 (2H, m), 8.43–8.90 (2H, m)
Mass (m/e): 285 (M$^+$)

EXAMPLE 17

6-[2-(5-Methyl-2-pyridyl)ethyl]-2-amino-4-bromobenzothiazole mp: 216°–218° C.
IR (Nujol): 1650, 1600, 1555, 1540 cm$^{-1}$
NMR (D$_2$O+DCl, δ): 2.55 (3H, s), 3.00–3.54 (4H, m), 7.46 (2H, s), 7.55 (1H, s), 7.83 (1H, d, J=5 Hz), 8.38 (1H, dd, J=2 Hz, 5 Hz), 8.54 (1H, d, J=2 Hz)
Mass (m/e): 349 (M+1)

EXAMPLE 18

6-[2-(3-Methyl-2-pyridyl)ethyl]-2-amino-4-bromobenzothiazole mp: 236°–237° C.
NMR (D$_2$O+DCl, δ): 2.50 (3H, s), 2.97–3.50 (4H, m), 7.41 (1H, d, J=2 Hz), 7.51 (1H, d, J=2 Hz), 7.83 (1H, q, J=6 Hz), 8.38 (1H, d, J=6 Hz), 8.47 (1H, d, J=6 Hz)
Mass (m/e): 349 (M+1)

EXAMPLE 19

6-[2-(2-Pyridyl)ethyl]-2-amino-4-bromobenzothiazole mp: 221°–223° C.
IR (Nujol): 1630, 1585, 1555, 1530 cm$^{-1}$
NMR (CF$_3$COOD, δ): 3.13–3.73 (4H, m), 7.63 (2H, s), 7.86–8.13 (2H, m), 8.46–8.80 (2H, m)
Mass (m/e): 334 (M$^+$)

EXAMPLE 20

6-[2-(3-Bromo-7-methylimidazo[1,2-a]pyridin-2-yl)ethyl]-2-aminobenzothiazole mp: 233°–236° C.
IR (Nujol): 1655 (br.), 1605 cm$^{-1}$
NMR (DMSO-d$_6$, δ): 235 (3H, s), 2.96 (4H, s), 6.83 (1H, dd, J=2 Hz, 7 Hz), 6.99 (1H, dd, J=2 Hz, 8 Hz), 7.18 (1H, d, J=8 Hz), 7.20–7.37 (3H, m), 7.44 (1H, s), 8.06 (1H, d, J=7 Hz)

EXAMPLE 21

A solution of 2-(4-aminobenzyl)pyridine (4.5 g) and ammonium thiocyanate (3.7 g) in acetic acid (50 ml) was stirred at ambient temperature for 1 hour. A solution of bromine (1.3 ml) in acetic acid (5 ml) was dropwise added thereto at 10° to 15° C. under stirring and the resulting mixture was stirred at 10° to 20° C. for 1 hour. A mixture of ethyl acetate and water was added to the reaction mixture and the mixture was adjusted to pH 7.5 with potassium carbonate. An insoluble material was filtered off and the filtrate was separated. The resulting organic layer was washed with brine and dried over magnesium sulfate. The solvent was evaporated and triturated with ethyl acetate. The precipitate was collected by filtration and dried to give 6-[(2-pyridyl)methyl]-2-aminobenzothiazole (0.83 g).

mp: 181°–183° C.
IR (Nujol): 1650, 1600 cm$^{-1}$
NMR (DMSO-d$_6$, δ): 4.06 (2H, s), 6.98–7.44 (6H, m), 7.51 (1H, s), 7.66 (1H, d t, J=2 Hz, 8 Hz), 8.46 (1H, d, J=5 Hz)
Mass (m/e): 241 (M$^+$)

The following compounds (Examples 22 to 24) were obtained according to a similar manner to that of Example 21.

EXAMPLE 22

6-[Hydroxy-(2-pyridyl)methyl]-2-aminobenzothiazole mp: 187°–189° C.
IR (Nujol): 1647, 1600 cm$^{-1}$
NMR (DMSO-d$_6$, δ): 5.72 (1H, d, J=4 Hz), 5.99 (1H, d, J=4 Hz), 7.06–7.45 (5H, m), 7.55 (1H, d, J=5 Hz), 7.63 (1H, s), 7.75 (1H, d t, J=2 Hz, 8 Hz), 7.42 (1H, d, J=5 Hz)
Mass (m/e): 257 (M$^+$)

EXAMPLE 23

6-[(2-Pyridyl)methoxy]-2-aminobenzothiazole mp: 169°–172° C.
IR (Nujol): 1650, 1600 cm$^{-1}$ NMR (DMSO-d$_6$, δ): 5.14 (2H, s), 6.89 (1H, dd, J=2 Hz, 9 Hz), 7.10–7.41 (5H, m), 7.50 (1H, d, J=8 Hz), 7.82 (1H, d t, J=2 Hz, 8 Hz), 8.54 (1H, d, J=5 Hz)
Mass (m/e): 257 (M$^+$)

EXAMPLE 24

6-[(2-Pyridyl)methylthio]-2-aminobenzothiazole mp: 169°–172° C.
IR (Nujol): 3250, 1660, 1600 cm$^{-1}$
NMR (DMSO-d$_6$, δ): 4.23 (2H, s)

EXAMPLE 25

A solution of 2-[2-(4-aminophenyl)ethyl]-7-methylimidazo[1,2-a]pyridine (2.5 g) and ammonium thiocyanate (1.5 g) in acetic acid (25 ml) was stirred at ambient temperature for 1 hour. A solution of bromine (0.6 ml) in acetic acid (3 ml) was dropwise added thereto at 15° to 18° C. under stirring and the resulting mixture was stirred at 10° to 20° C. for 1 hour. A mixture of ethyl acetate and water was added to the reaction mixture and the mixture was adjusted to pH 7.5 with potassium carbonate. The separated organic layer was washed with brine and dried over magnesium sulfate. The crude product obtained by concentration was purified by silica gel column chromatography eluting with a mixture of chloroform and methanol (19:1 V/V). The eluted fractions containing desired product were evaporated to give 6-[2-(7-methylimidazo[1,2-a]pyridin-2-yl)ethyl]-2-aminobenzothiazole (0.43 g).

mp: 245°–246° C. (dec.)
IR (Nujol): 1650, 1605 cm$^{-1}$
NMR (DMSO-d$_6$, δ): 2.31 (3H, s), 2.97 (4H, s), 6.61 (1H, d, J=7 Hz), 7.05 (1H, d, J=8 Hz), 7.14–7.39 (4H, m), 7.52 (2H, s), 8.27 (1H, d, J=7 Hz)
Mass (m/e): 308 (M$^+$)

EXAMPLE 26

A mixture of 2-[2-(4-aminophenyl)ethyl]-3,7-dimethylimidazo[1,2-a]pyridine (2.1 g) and ammonium thiocyanate (1.2 g) in acetic acid (21 ml) was stirred at ambient temperature for 1 hour. A solution of bromine (0.4 ml) in acetic acid (2 ml) was dropwise added thereto at 15° C. to 18° C. under stirring and a mixture was stirred at 15° C. to 18° C. for 2 hours. The reaction mixture was added to a mixture of ethyl acetate and water and the mixture was adjusted to pH 8 with potassium carbonate. The isolated rubberlike substance was collected by decantation of the supernatant solvent. The resulting substance was triturated with a solution of methanol and tetrahydrofuran and the precipitate was collected by filtration. To the precipitate was added water (20 ml) and a mixture was adjusted to pH 1.0 with 10% hydrochloric acid under ice-cooling. The isolated substance was collected by filtration and dried to give 6-[2-(3,7-dimethylimidazo[1,2-a]pyridin-2-yl)ethyl]-2-aminobenzothiazole dihydrochloride (0.84 g).

mp: 119°-121° C.

IR (Nujol): 1670, 1645, 1600, 1580 cm$^{-1}$

NMR (D$_2$O, δ): 2.38 (3H, s), 2.66 (3H, s), 3.09 (4H, s), 7.10–7.43 (3H, m), 7.43–7.75 (2H, m), 8.25 (1H, d, J=7 Hz)

Mass (m/e): 322 (M-2HCl)

EXAMPLE 27

A mixture of 2-[2-{3-(3-ethylureido)-4-hydroxyphenyl}ethyl]pyridine (3.3 g) and polyphosphate ester (30 g) was stirred at 110° to 115° C. for one hour. To a reaction mixture was added a mixture of ethyl acetate and water and the resultant mixture was acidified to pH 1.0 with 10% hydrochloric acid. The separated aqueous layer was adjusted to pH 8.0 with aqueous 20% potassium carbonate and extracted with ethyl acetate. The extract was washed with brine and dried over magnesium sulfate. The solvent was evaporated in vacuo and the residue was subjected to column chromatography on silica gel. The fraction eluted with a mixture of chloroform and methanol (19:1 V/V) was collected and the solvent was evaporated in vacuo. The oily residue was crystallized from 15% hydrogen chloride-ethanol and tetrahydrofuran to give 5-[2-(2-pyridyl)ethyl]-2-ethylaminobenzoxazole dihydrochloride (0.97 g).

mp: 242°-244° C. (dec.)

IR (Nujol): 2600–1980, 1715, 1615 cm$^{-1}$

NMR (D$_2$O, δ): 1.40 (3H, t, J=7 Hz), 3.10–3.56 (4H, m), 3.62 (2H, q, J=7 Hz), 7.12 (1H, dd, J=2 Hz, 8 Hz), 7.24 (1H, d, J=2 Hz), 7.43 (1H, d, J=8 Hz), 7.70–8.03 (2H, m), 8.50 (1H, dt, J=2 Hz, 8 Hz), 8.63 (1H, dd, J=2 Hz, 6 Hz)

Mass (m/e): 267 (M$^+$)

EXAMPLE 28

5-[2-(3-Pyridyl)ethyl]-2-ethylaminobenzoxazole dihydrochloride was obtained according to a similar manner to that of Example 27.

mp: 230°-233° C. (dec.)

IR (Nujol): 2600, 1980, 1715, 1625, 1550 cm$^{-1}$

NMR (D$_2$O, δ): 1.43 (3H, t, J=7 Hz), 3.23 (4H, m), 3.63 (2H, q, J=7 Hz), 7.14 (1H, dd, J=2 Hz, 8 Hz), 7.28 (1H, d, J=2 Hz), 7.46 (1H, d, J=8 Hz), 8.02 (1H, dd, J=5 Hz, 8 Hz), 8.45 (1H, dd, J=2 Hz, 8 Hz), 8.60 (1H, d, J=2 Hz), 8.72 (1H, dd, J=2 Hz, 5 Hz)

Mass (m/e): 267 (M$^+$)

EXAMPLE 29

A mixture of 2-[2-{4-(3-ethylureido)-3-hydroxyphenyl}ethyl]pyridine (3.3 g) and polyphosphate ester (30 g) was stirred at 90° to 100° C. for 1.5 hours. The reaction mixture was dissolved in a mixture of ethyl acetate, tetrahydrofuran and water and the resultant solution was adjusted to pH 8 with potassium carbonate. The separated organic layer was washed with brine and dried over magnesium sulfate. The crude product obtained by concentration was purified by silica gel column chromatography eluting with a solution of chloroform and methanol (39:1 V/V). The eluted fractions containing desired product were evaporated to give 6-[2-(2-pyridyl)ethyl]-2-ethylaminobenzoxazole (0.5 g).

mp: 57°-59° C.

IR (Nujol): 1655, 1590 cm$^{-1}$

NMR (DMSO-d$_6$, δ): 1.20 (3H, t, J=7 Hz), 3.00 (4H, s), 3.33–3.55 (2H, m), 6.76–7.31 (5H, m), 7.47–7.82 (2H, m), 8.33–8.50 (1H, m)

Mass (m/e): 267 (M$^+$)

EXAMPLE 30

A mixture of 2-[2-{4-(3-ethylureido)-3-hydroxyphenyl}ethyl]-7-methylimidazo[1,2-a]pyridine (17.5 g) and polyphosphate ester (170 g) was stirred at 110° to 120° C. for one hour. The reaction mixture was dissolved in a mixture of ethyl acetate, tetrahydrofuran and water and the resultant solution was adjusted to pH 8.0 with potassium carbonate. The separated organic layer was washed with brine and dried over magnesium sulfate. The crude product obtained by concentration was purified by alumina column chromatography eluting with chloroform. The eluted fraction containing the desired product was evaporated to give 6-[2-(7-methylimidazo[1,2-a]pyridin-2-yl)ethyl]-2-ethylaminobenzoxazole (1.41 g).

mp: 156°-158° C.

IR (Nujol): 3150, 1650, 1590 cm$^{-1}$

NMR (DMSO-d$_6$, δ): 1.18 (3H, t, J=7 Hz), 2.31 (3H, s), 2.97 (4H, s), 3.10–3.51 (2H, m), 6.61 (1H, dd, J=2 Hz, 7 Hz), 6.93 (1H, dd, J=2 Hz, 7 Hz), 7.10 (1H, d, J=7 Hz), 7.18 (2H, s), 7.50 (1H, s), 7.70 (1H, t, J=5 Hz), 8.26 (1H, d, J=7 Hz)

Mass (m/e): 320 (M$^+$)

The following compounds (Examples 31 and 32) were obtained according to a similar manner to that of Example 30.

EXAMPLE 31

5-[2-(7-Methylimidazo[1,2-a]pyridin-2-yl)ethyl]-2-ethylaminobenzoxazole mp: 114°-116° C.

IR (Nujol): 1645, 1590 cm$^{-1}$

NMR (DMSO-d$_6$, δ): 1.18 (3H, t, J=7 Hz), 2.33 (3H, s), 2.99 (4H, s), 3.11–3.52 (2H, m), 6.62 (1H, d, J=7 Hz), 6.81 (1H, d, J=8 Hz), 6.97–7.33 (3H, m), 7.53 (1H, s), 7.76 (1H, t, J=5 Hz), 8.24 (1H, d, J=7 Hz)

EXAMPLE 32

6-[2-(3-Bromo-7-methylimidazo[1,2-a]pyridin-2-yl)ethyl]-2-ethylaminobenzoxazole mp: 149°-153° C.

NMR (DMSO-d$_6$, δ): 1.18 (3H, t, J=7 Hz), 2.37 (3H, s), 3.00 (4H, s), 3.13–3.49 (2H, m), 6.87 (1H, dd, J=2 Hz, 7 Hz), 7.01 (1H, dd, J=2 Hz, 8 Hz), 7.11 (1H, d, J=8 Hz), 7.15 (1H, s), 7.34 (1H, s), 7.72 (1H, t, J=5 Hz), 8.10 (1H, d, J=7 Hz)

Mass (m/e): 399 (M$^+$)

EXAMPLE 33

The mixture of 3,7-dimethyl-2-[2-{3-hydroxy-4-(3-methylureido)phenyl}ethyl]imidazo[1,2-a]pyridine (2.7 g) and polyphosphate ester (20 g) was stirred for 2.5 hours at 120° C. To the reaction mixture was added a mixture of water and ethyl acetate and the separated aqueous layer was adjusted to pH 8 with potassium carbonate. The aqueous mixture was extracted with a solution of ethyl acetate and tetrahydrofuran. The extract was washed with brine and dried over magnesium sulfate. Evaporation of the solvent gave a residue, which was subjected to a column chromatography on alumina eluting with chloroform. The fractions containing desired product were combined and evaporated to give 6-[2-(3,7-dimethylimidazo[1,2-a]pyridin-2-yl)ethyl]-2-methylaminobenzoxazole (0.51 g).

mp: 203°–205° C.

IR (Nujol): 1663, 1588 cm$^{-1}$

NMR (DMSO-d$_6$, δ): 2.18 (3H, s), 2.31 (3H, s), 2.86 (3H, d, J=5 Hz), 2.93 (4H, s), 6.62 (1H, dd, J=2 Hz, 7 Hz), 6.84 (1H, dd, J=2 Hz, 7 Hz), 7.04 (1H, d, J=7 Hz), 7.09 (1H, s), 7.16 (1H, s), 7.56 (1H, q, J=5 Hz), 7.91 (1H, d, J=7 Hz)

Mass (m/e): 320 (M$^+$)

The following compounds (Examples 34 to 37) were obtained according to a similar manner to that of Example 33.

EXAMPLE 34

6-[2-(3,7-Dimethylimidazo[1,2-a]pyridin-2-yl)ethyl]-2-ethylaminobenzoxazole mp: 189°–190° C.

IR (Nujol): 3200, 1650, 1585 cm$^{1-1}$

NMR (DMSO-d$_6$, δ): 1.17 (3H, t, J=7 Hz), 2.19 (3H, s), 2.32 (3H, s), 2.92 (4H, s), 3.09–3.49 (2H, m), 6.62 (1H, d, J=7 Hz), 6.84 (1H, d), 7.91 (1H, d, J=7 Hz)

Mass (m/e): 334 (M$^+$)

EXAMPLE 35

6-[2-(3,7-Dimethylimidazo[1,2-a]pyridin-2-yl)ethyl]-2-isopropylaminobenzoxazole

IR (Nujol): 1640, 1580 cm$^{-1}$

NMR (DMSO-d$_6$, δ): 1.21 (6H, d, J=7 Hz), 2.20 (3H, s), 2.32 (3H, s), 2.93 (4H, m), 3.60–4.05 (1H, m), 6.63 (1H, dd, J=2 Hz, 7 Hz), 6.85 (1H, dd, J=2 Hz, 8 Hz), 6.96–7.24 (3H, m), 7.60 (1H, d, J=7 Hz), 7.93 (1H, d, J=7 Hz)

Mass (m/e): 348 (M$^+$)

EXAMPLE 36

6-[2-(3-Methylimidazo[1,2-a]pyridin-2-yl)ethyl]-2-ethylaminobenzoxazole mp: 132°–134° C.

IR (Nujol): 1650, 1585 cm$^{-1}$

NMR (DMSO-d$_6$, δ): 1.17 (3H, t, J=7 Hz), 2.24 (3H, s), 2.96 (4H, s), 3.09–3.50 (2H, m), 6.65–6.95 (2H, m), 6.95–7.20 (3H, m), 7.26–7.51 (1H, m), 7.68 (1H, t, J=5 Hz), 7.88—8.19 (1H, m)

EXAMPLE 37

6-(3,7-Dimethylimidazo[1,2-a]pyridin-2-yl)ethyl]-2-allylaminobenzoxazole mp: 186°–187° C.

IR (Nujol): 1650, 1588 cm$^{-1}$

NMR (DMSO-d$_6$, δ): 2.20 (3H, s), 2.32 (3H, s), 2.92 (4H, s), 3.89 (2H, m), 4.96–5.35 (2H, m), 5.66–6.14 (1H, m), 6.64 (1H, dd, J=2 Hz, 7 Hz), 6.86 (1H, dd, J=2 Hz, 8 Hz), 6.97–7.24 (3H, m), 7.74–8.02 (2H, m)

EXAMPLE 38

A mixture of 3-[3-(3-ethylureido)-4-hydroxybenzyl]-2,7-dimethylimidazo[1,2-a]pyridine (3.7 g) and polyphosphate ester (37 g) was stirred at 110° to 120° C. for one hour. The reaction mixture was dissolved in a mixture of ethyl acetate and water and the resultant solution was acidified to pH 1.0 with 10% hydrochloric acid. The separated aqueous layer was adjusted to pH 8.0 with aqueous 20% potassium carbonate and extracted with ethyl acetate. The extract was washed with brine and dried over magnesium sulfate. The solvent was evaporated in vacuo and the residue was subjected to column chromatography on alumina. The fraction eluted with a mixture of chloroform and methanol (98:2 V/V) was collected and the solvent was evaporated in vacuo and the residue was recrystallized from a mixture of chloroform and diethyl ether to give 5-(2,7-dimethylimidazo[1,2-a]pyridin-3-ylmethyl)-2-ethylaminobenzoxazole (0.9 g).

mp: 209°–211° C.

IR (Nujol): 1655, 1590, 1545, 1505 cm$^{-1}$

NMR (DMSO-d$_6$, δ): 1.15 (3H, t, J=7 Hz), 2.28 (3H, s), 2.38 (3H, s), 3.13–3.50 (2H, m), 4.25 (2H, s), 6.59 (1H, dd, J=2 Hz, 7 Hz), 6.74 (1H, dd, J=2 Hz, 8 Hz), 6.99 (1H, d, J=2 Hz), 7.18 (1H, d, J=2 Hz), 7.18 (1H, d, J=8 Hz), 7.81 (1H, t, J=5 Hz), 7.95 (1H, d, J=7 Hz)

Mass (m/e): 320 (M$^+$)

EXAMPLE 39

A mixture of 4-methyl-2-[1-{3-(4-amino-3-hydroxyphenyl)propionamido}ethyl]pyridine (8.0 g) and ethyl isocyanate (2.2 ml) in tetrahydrofuran (100 ml) was stirred for 2.5 hours at ambient temperature. The solvent was evaporated in vacuo and the residue was dissolved with a mixture of methanol and chloroform (5:95 V/V) and washed with brine and dried over magnesium sulfate. The solvent was evaporated in vacuo to give a residue including 4-methyl-2-[1-[3-{4-(3-ethylureido)-3-hydroxyphenyl}propionamido]ethyl]pyridine. The residue was stirred with polyphosphate ester (66 g) at 140° C. for 1 hour. The mixture was poured into ice-water, adjusted to pH 8 with 20% potassium carbonate and extracted with tetrahydrofuran by salting out technique. The extract was washed with brine and dried over magnesium sulfate and the solvent was removed under reduced pressure. The residue was crystallized from a mixture of chloroform and ethyl acetate to give 6-[2-(1,7-dimethylimidazo[1,5-a]pyridin-3-yl)ethyl]-2-ethylaminobenzoxazole (1.7 g).

mp: 175°–177° C.

IR (Nujol): 3200, 1655, 1570 cm$^{-1}$

NMR (CDCl$_3$, δ): 1.30 (3H, t, J=7 Hz), 2.21 (3H, s), 2.46 (3H, s), 3.18 (3H, s), 3.50 (2H, q, J=7 Hz), 3.7–4.2 (1H, br s), 6.21 (1H, dd, J=2 Hz, 8 Hz), 6.96 (1H, d, J=8 Hz), 7.01 (1H, s), 7.04 (1H, d, J=2 Hz), 7.24 (1H, d, J=8 Hz), 7.35 (1H, d, J=8 Hz)

Mass (m/e): 334 (M$^+$)

EXAMPLE 40

To a solution of 6-[2-(5-methyl-2-pyridyl)ethyl]-2-aminobenzothiazole (1.35 g) in acetic acid (15 ml) was dropwise added a solution of bromine (0.8 g) in acetic acid (2 ml) at 20° to 22° C. under stirring and the resultant mixture was stirred at ambient temperature for 5 hours. The reaction mixture was poured into a mixture of water and ethyl acetate and the mixture was acidified to pH 1.0 with 10% hydrochloric acid. The separated aqueous layer was adjusted to pH 8.0 with aqueous 20% potassium carbonate and extracted with a mixture of ethyl acetate and tetrahydrofuran. The extract was washed with brine and dried over magnesium sulfate. The solvent was evaporated in vacuo and residue was recrystallized from a mixture of ethyl acetate and tetrahydrofuran to give 6-[2-(5-methyl-2-pyridyl)ethyl]-2-amino-4-bromobenzothiazole (0.9 g).

mp: 216°–218° C.

IR (Nujol): 1650, 1600, 1555, 1540 cm$^{-1}$

NMR (D$_2$O+DCl, δ): 2.55 (3H, s), 3.00-3.54 (4H, m), 7.46 (2H, s), 7.55 (1H, s), 7.83 (1H, d, J=5 Hz), 8.38 (1H, dd, J=2 Hz, 5 Hz), 8.54 (1H, d, J=2 Hz)

Mass (m/e): 349 (M+1)

The following compounds (Examples 41 and 42) were obtained according to a similar manner to that of Example 40.

EXAMPLE 41

6-[2-(3-Methyl-2-pyridyl)ethyl]-2-amino-4-bromobenzothiazole mp: 236°-237° C.

IR (Nujol): 1630, 1560, 1535 cm$^{-1}$

NMR (D$_2$O+DCl, δ): 2.50 (3H, s), 2.97-3.50 (4H, m), 7.41 (1H, d, J=2 Hz), 7.51 (1H, d, J=2 Hz), 7.83 (1H, q, J=6 Hz), 8.38 (1H, d, J=6 Hz), 8.47 (1H, d, J=6 Hz)

Mass (m/e): 349 (M+1)

EXAMPLE 42

6-[2-(2-Pyridyl)ethyl]-2-amino-4-bromobenzothiazole mp: 221°-223° C.

IR (Nujol): 1630, 1585, 1555, 1530 cm$^{-1}$

NMR (CF$_3$COOD, δ): 3.13-3.73 (4H, m), 7.63 (2H, s), 7.86-8.13 (2H, m), 8.46-8.80 (2H, m)

Mass (m/e): 334 (M+)

EXAMPLE 43

A mixture of 6-[2-(7-methylimidazo[1,2-a]pyridin-2-yl)ethyl]-2-aminobenzothiazole (0.4 g), pyridinium hydrobromide perbromide (0.5 g) and 25% hydrogen bromide-acetic acid (0.1 ml) in acetic acid (4 ml) was stirred at ambient temperature for 1 hour. The reaction mixture was added to a mixture of ethyl acetate and water and the mixture was adjusted to pH 8 with 20% aqueous potassium carbonate. The separated organic layer was washed with brine and dried over magnesium sulfate. The solvent was evaporated to give a residue, which was triturarted with a solution of ethyl acetate and diethyl ether to give a precipitate. The precipitate was collected by filtration and dried to give 6-[2-(3-bromo-7-methylimidazo[1,2-a]pyridin-2-yl)ethyl]-2-aminobenzothiazole (0.38 g).

mp: 233°-236° C.

IR (Nujol): 1655 (br.), 1605 cm$^{-1}$

NMR (DMSO-d$_6$, δ): 2.35 (3H, s), 2.96 (4H, s), 6.83 (1H, dd, J=2 Hz, 7 Hz), 6.99 (1H, dd, J=2 Hz, 8 Hz), 7.18 (1H, d, J=8 Hz), 7.20-7.37 (3H, m), 7.44 (1H, s), 8.06 (1H, d, J=7 Hz)

EXAMPLE 44

6-[2-(3-Bromo-7-methylimidazo[1,2-a]pyridin-2-yl)ethyl]-2-ethylaminobenzoxazole was obtained according to a similar manner to that of Example 43.

mp: 149°-153° C.

IR (Nujol): 3200, 1650, 1585 cm$^{-1}$

NMR (DMSO-d$_6$, δ): 1.18 (3H, t, J=7 Hz) 2.37 (3H, s), 3.00 (4H, s), 3.13-3.49 (2H, m), 6.87 (1H, dd, J=2 Hz, 7 Hz), 7.01 (1H, dd, J=2 Hz, 8 Hz), 7.11 (1H, d, J=8 Hz), 7.15 (1H, s), 7.34 (1H, s), 7.72 (1H, t, J=5 Hz), 8.10 (1H, d, J=7 Hz)

Mass (m/e): 399 (M+)

EXAMPLE 45

A solution of 6-[(2-pyridyl)methyl]-2-aminobenzothiazole (1.3 g) and ethyl isocyanate (0.6 ml) in tetrahydrofuran (25 ml) was stirred at 60° C. for 4 hours. Evaporation of the solvent gave a residue which was crystallized from tetrahydrofuran. The crystal was collected by filtration to give 6-[(2-pyridyl)methyl]-2-(3-ethylureido)benzothiazole (0.68 g).

mp: 184°-185° C.

IR (Nujol): 3300, 1670, 1610, 1580 cm$^{-1}$

NMR (DMSO-d$_6$, δ): 1.09 (3H, t, J=7 Hz), 2.96-3.45 (2H, m), 4.10 (2H, s), 6.70 (1H, t, J=5 Hz), 7.03-7.46 (3H, m), 7.49 (1H, d, J=8 Hz), 7.50-7.80 (1H, m), 7.73 (1H, s), 8.45 (1H, d, J=5 Hz), 10.55 (1H, br s)

Mass (m/e): 312 (M+)

EXAMPLE 46

A solution of 25% aqueous sodium hydroxide was added to a mixture of S-methylisothiourea sulfate (2.8 g) and methyl chloroformate (1.89 g) in water (10 ml) until pH 7.0 to 8.0 at 10° to 15° C. under stirring, and the resultant mixture was adjusted to pH 5.0 with acetic acid. The above solution containing methyl S-methylisothioureidoformate was added to a solution of 3-methyl-2-[2-(3,4-diaminophenyl)ethyl]pyridine (2.27 g) in ethanol (30 ml) at ambient temperature and the resultant mixture was stirred at the same condition for 4 hours. The precipitate was collected by filtration. The precipitate was suspended to a water and the mixture was acidified to pH 1.0 with 10% hydrochloric acid. The acidified solution was washed with ethyl acetate. The aqueous solution was adjusted to pH 8.0 with aqueous 20% potassium carbonate and extracted with a mixture of chloroform, methanol and tetrahydrofuran. The extract was washed with brine and dried over magnesium sulfate. The solvent was concentrated in vacuo and the crystalline residue was collected by filtration. The residue was washed with ethyl acetate to give 5-[2-(3-methyl-2-pyridyl)ethyl]-2-methoxycarbonylamino-1-benzimidazole (1.61 g).

mp: 194°-196° C.

IR (Nujol): 3300, 1630, 1600, 1595 cm$^{-1}$

NMR (D$_2$O+DCl, δ): 2.44 (3H, s), 3.00-3.50 (4H, m), 4.03 (3H, s), 7.16 (1H, dd, J=2 Hz, 8 Hz), 7.30 (1H, s), 7.44 (1H, d, J=8 Hz), 7.83 (1H, dd, J=6 Hz, 8 Hz), 8.37 (1H, d, J=8 Hz), 8.43 (1H, d, J=6 Hz)

Mass (m/e): 310 (M+)

EXAMPLE 47

5-[2-(2-Pyridyl)ethyl]-2-methoxycarbonylamino-1H-benzimidazole was obtained according to a similar manner to that of Example 46.

mp: 215°-216° C. (dec.)

IR (Nujol): 3320, 1630, 1595, 1520 cm$^{-1}$

NMR (D$_2$O+DCl, δ): 3.10-3.60 (4H, m), 4.05 (3H, s), 7.23 (1H, d, J=8 Hz), 7.38 (1H, s), 7.45 (1H, d, J=8 Hz), 7.93 (1H, d, J=8 Hz), 8.00 (1H, d, J=6 Hz), 8.51 (1H, dd, J=2 Hz, 8 Hz), 8.68 (1H, dd, J=2 Hz, 6 Hz)

Mass (m/e): 296 (M+)

EXAMPLE 48

A solution of 3-methyl-2-[2-(3,4-diaminophenyl)ethyl]pyridine (2.3 g) and cyanogen bromide (1.2 g) in ethanol (50 ml) was stirred at ambient temperature for 2 hours. The reaction mixture was evaporated in vacuo and the residue was dissolved in a mixture of ethyl acetate and water. The resultant solution was adjusted to pH 8.0 with aqueous 20% potassium carbonate. Separated ethyl acetate layer was washed with brine and dried over magnesium sulfate. The solvent was evaporated in vacuo and the residue was subjected to column chromatography on alumina. The fraction eluted with a mixture of chloroform and methanol (98:2 V/V) was collected and solvent was evaporated in vacuo. The residue was crystallized from 15% hydrogen chloride-ethanol and tetrahydrofuran to give 5-[2-(3-methyl-2-pyridyl)ethyl]-2-amino-1H-benzimidazole dihydrochloride (1.1 g).

mp: 263°–265° C. (dec.)
IR (Nujol): 1665 cm$^{-1}$
NMR (D$_2$O, δ): 2.50 (3H, s), 2.85–3.46 (4H, m), 6.80–7.37 (3H, m), 7.92 (1H, dd, J=5 Hz, 7 Hz), 8.47 (1H, d, J=7 Hz), 8.54 (1H, d, J=5 Hz)
Mass (m/e): 253 (M$^+$)

EXAMPLE 49

A mixture of 2-[2-(4-amino-3-hydroxyphenyl)ethyl]-3,7-dimethylimidazo[1,2-a]pyridine (11.0 g) and cyanogenbromide (5.0 g) in ethanol (165 ml) was stirred for 100 minutes at ambient temperature. To the reaction mixture was added a solution of ethyl acetate and water, and the mixture was adjusted to pH 1.0 with 10% hydrochloric acid. The separated aqueous layer was adjusted to pH 8 with 20% aqueous potassium carbonate and the resulting precipitate was collected by filtration. The precipitate was subjected to a column chromatography on alumina eluting with a solution of chloroform and methanol (19:1 V/V). The fractions containing desired product were combined and evaporated to give 6-[2-(3,7-dimethylimidazo[1,2-a]pyridin-2-yl)ethyl]-2-aminobenzoxazole (7.45 g).

mp: 244°–246° C.
IR (Nujol): 1680, 1650, 1620, 1575 cm$^{-1}$
NMR (D$_2$O-DCl, δ): 2.29 (3H, s), 2.58 (3H, s), 3.14 (4H, s), 7.18 (1H, dd, J=2 Hz, 8 Hz), 7.23–7.45 (3H, m), 7.58 (1H, s), 8.24 (1H, d, J=8 Hz)

EXAMPLE 50

6-[2-(7-Methoxy-3-methylimidazo[1,2-a]pyridin-2-yl)ethyl]-2-aminobenzoxazole was obtained according to a similar manner to that of Example 49.

mp: 220°–221° C.
IR (Nujol): 1665, 1580 cm$^{-1}$
NMR (DMSO-d$_6$, δ): 2.19 (3H, s), 2.93 (4H, s), 3.82 (3H, s), 6.58 (1H, dd, J=2 Hz, 7 Hz), 6.82–7.10 (3H, m), 7.13–7.40 (3H, m), 7.99 (1H, d, J=7 Hz)

EXAMPLE 51

A mixture of 2-[2-(4-amino-3-hydroxyphenyl)ethyl]-3,7-dimethylimidazo[1,2-a]pyridine (2.5 g) and (dichloromethylene)dimethylammonium chloride (1.4 g) in chloroform (100 ml) was refluxed for 2.5 hours. To the reaction mixture was added the water and the separated aqueous layer was adjusted to pH 8 with potassium carbonate. The resulting aqueous mixture was extracted with a mixture of ethyl acetate and tetrahydrofuran. The extract was washed with brine and dried over magnesium sulfate. The solvent was evaporated and the residue was extracted with chloroform (30 ml) under reflux. Evaporation of the solvent gave a residue, which was subjected to a column chromatography on alumina eluting with chloroform. The fractions containing desired product were combined and evaporated to give 6-[2-(3,7-dimethylimidazo[1,2-a]pyridin-2-yl)ethyl]-2-dimethylaminobenzoxazole (0.29 g).

mp: 67°–69° C.
IR (Nujol): 1660, 1587 cm$^{-1}$
NMR (DMSO-d$_6$, δ): 2.19 (3H, s), 2.32 (3H, s), 2.93 (4H, s), 3.08 (6H, s), 6.65 (1H, dd, J=2 Hz, 7 Hz), 6.89 (1H, dd, J=2 Hz, 8 Hz), 7.08 (1H, d, J=8 Hz), 7.08–7.23 (2H, m), 7.95 (1H, d, J=7 Hz)
Mass (m/e): 334 (M$^+$)

EXAMPLE 52

Conc. hydrochloric acid (1.1 ml) was added to a mixture of 6-[2-(3,7-dimethylimidazo[1,2-a]pyridin-2-yl)ethyl]-2-aminobenzoxazole (1.5 g) in ethanol (9 ml) and the mixture was stirred for 5 minutes at ambient temperature. The isolated crystal was collected by filtration and the resulting crystal was recrystallized from a mixture of ethanol and ethyl acetate to give 6-[2-(3,7-dimethylimidazo[1,2-a]pyridin-2-yl)ethyl]-2-aminobenzoxazole dihydrochloride (0.91 g).

mp: 268°–270° C.
IR (Nujol): 1710, 1667 cm$^{-1}$
NMR (D$_2$O, δ): 2.29 (3H, s), 2.64 (3H, s), 3.21 (4H, s), 7.21 (1H, d, J=7 Hz), 7.29–7.45 (3H, m), 7.63 (1H, s), 8.27 (1H, d, J=7 Hz)

EXAMPLE 53

6-[2-(7-Methoxy-3-methylimidazo[1,2-a]pyridin-2-yl)ethyl]-2-aminobenzoxazole dihydrochloride was obtained according to a similar manner to that of Example 52.

mp: 252°–255° C.
IR (Nujol): 1705, 1670 cm$^{-1}$
NMR (D$_2$O, δ): 2.18 (3H, s), 3.11 (4H, s), 4.03 (3H, s), 7.02 (1H, dd, J=2 Hz, 8 Hz), 7.08–7.44 (4H, m), 8.14 (1H, d, J=8 Hz)

Preparation 60

A solution of bromine (71 ml) in dichloromethane (35 ml) was dropwise added to a solution of 2-butanone (62 ml) in dichloromethane (500 ml) for 1.5 hours at 20° to 28° C. and the mixture was stirred for 30 minutes at ambient temperature. The solvent was evaporated in vacuo and the residue was dissolved in ethyl acetate (600 ml). To the solution was added triphenylphosphine (181.9 g) at ambient temperature and the mixture was stirred for 2 hours at the same temperature. The isolated precipitate was collected by filtration and washed with a mixture of water and ethyl acetate and dried to give (3-bromo-2-oxobutyl)triphenylphosphonium bromide (132.3 g).

mp: 189°–191° C.
IR (Nujol): 1720 cm$^{-1}$

Preparation 61

A mixture of (3-bromo-2-oxobutyl)triphenylphosphonium bromide (30 g) in ethyl acetate (150 ml), tetrahydrofuran (50 ml) and water (150 ml) was adjusted to pH 10 with potassium carbonate. The separated organic layer was washed with brine and dried over magnesium sulfate. Evaporation of the solvent gave a residue, which was triturated with diisopropyl ether and collected by filtration to give (3-bromo-2-oxobutylidene)triphenylphosphorane (24.27 g).

mp: 150°–153° C.
IR (Nujol): 1550 cm$^{-1}$
NMR (DMSO-d$_6$, δ): 1.71 (3H, d, J=7 Hz), 4.01 (1H, d, J=24 Hz), 4.47–4.91 (1H, m), 7.41–8.06 (15H, m)

Preparation 62

A mixture of (3-chloro-2-oxobutylidene)triphenylphosphorane (12.7 g) and 3-benzyloxy-4-nitrobenzaldehyde (8.9 g) in dioxane (130 ml) was heated under reflux for 2 hours. The solvent was evaporated in vacuo and the residue was dissolved in isopropyl alcohol (130 ml). To the solution was added 2-amino-4-ethoxypyridine (12.0 g) and the mixture was heated under reflux for 2.5 hours. Evaporation of the solvent gave a residue, which was dissolved in a mixture of ethyl acetate and water. The mixture was adjusted to pH 1 with 6N-hydrochloric acid and the isolated precipitate was collected by filtration. To the precipitate was added a mixture of tetrahydrofuran, ethyl acetate and water, and the mixture was adjusted to pH 8 with 20% aqueous potassium carbonate solution with salting-out technique. The separated organic layer was washed with brine and dried over magnesium sulfate. The solvent was evaporated and the residue was triturated with a mixture of diethyl ether and diisopropyl ether. The precipitate was collected by filtration and dried to give 2-[2-(3-benzyloxy-4-nitrophenyl)vinyl]-7-ethoxy-3-methylimidazo[1,2-a]pyridine (3.94 g).

mp: 153°–154° C.

IR (Nujol): 1650, 1635, 1600, 1585 cm$^{-1}$ (DMSO-d$_6$, δ): 1.39 (3H, t, J=7 Hz), 2.60 (3H, s), 4.13 (2H, q, J=7 Hz), 5.44 (2H, s), 6.63 (1H, dd, J=2 Hz, 7 Hz), 6.86 (1H, d, J=2 Hz), 7.30–7.97 (10H, m), 8.11 (1H, d, J=7 Hz)

Preparation 63

The following compounds were obtained according to a similar manner to that of Preparation 62.

(1) 2-[2-(3-Benzyloxy-4-nitrophenyl)vinyl]-7-methoxycarbonyl-3-methylimidazo[1,2-a]pyridine (2.48 g) was obtained from (3-bromo-2-oxobutylidene)triphenylphosphorane (5.0 g), 3-benzyloxy-4-nitrobenzaldehyde (3.1 g) and 2-amino-4-methoxycarbonylpyridine (4.6 g).

mp: 127°–129° C.

IR (Nujol): 1710, 1600, 1580, 1500, 1340 cm$^{-1}$

NMR (DMSO-d$_6$, δ): 2.61 (3H, s), 3.85 (3H, s), 5.35 (2H, s), 7.23 (1H, dd, J=2 Hz, 7 Hz), 7.30–7.76 (9H, m), 7.85 (1H, d, J=8 Hz), 7.98 (1H, s), 6.23 (1H, d, J=7 Hz)

(2) 2-[2-(3-Benzyloxy-4-nitrophenyl)vinyl]-7-carbamoyl-3-methylimidazo[1,2-a]pyridine was obtained from (3-bromo-2-oxobutylidene)triphenylphosphorane, 3-benzyloxy-4-nitrobenzaldehyde and 2-amino-4-carbamoylpyridine.

mp: >250° C.

IR (Nujol): 1665, 1600, 1580 cm$^{-1}$

MASS (m/e): 428 (M$^+$)

(3) 2-[2-(3-Benzyloxy-4-nitrophenyl)vinyl]-7-methoxyimidazo[1,2-a]pyridine was obtained from (3-chloro-2-oxopropylidene)triphenylphosphorane, 3-benzyloxy-4-nitrobenzaldehyde and 4-methoxy-2-aminopyridine.

mp: 121°–126° C.

IR (Nujol): 1640, 1600 cm$^{-1}$ (4) 2-[2-(3-Benzyloxy-4-nitrophenyl)vinyl]-7-tert-butoxycarbonylamino-3-methylimidazo[1,2-a]pyridine (5.84 g) was obtained from (3-bromo-2-oxobutylidene)triphenylphosphorane (10.5 g), 3-benzyloxy-4-nitrobenzaldehyde (6.6 g) and 2-amino-4-tert-butoxycarbonylaminopyridine (13.4 g).

mp: 104°–106° C.

IR (Nujol): 3330, 1710, 1630, 1595, 1580, 1560 cm$^{-1}$

NMR (DMSO-d$_6$, δ): 1.52 (9H, s), 2.61 (3H, s), 5.45 (2H, s), 7.05 (1H, dd, J=2 Hz, 7 Hz), 7.22–7.80 (10H, m), 7.95 (1H, d, J=8 Hz), 8.16 (1H, d, J=7 Hz), 9.67 (1H, s)

(5) 2-[2-(3-Benzyloxy-4-nitrophenyl)vinyl]-8-acetylamino-3-methylimidazo[1,2-a]pyridine (2.1 g) was obtained from (3-bromo-2-oxobutylidene)triphenylphosphorane (5.0 g), 3-benzyloxy-4-nitrobenzaldehyde (3.1 g) and 2-amino-3-acetylaminopyridine (4.6 g).

mp: 132°–134° C.

IR (Nujol): 3400, 1685, 1600, 1580 cm$^{-1}$

NMR (DMSO-d$_6$, δ): 2.28 (3H, s), 2.64 (3H, s), 5.46 (2H, s), 6.93 (1H, dd, J=each 7 Hz), 7.32–7.82 (9H, m), 7.90–8.11 (3H, m), 9.74 (1H, s)

Preparation 64

A solution of 2-[2-(3-benzyloxy-4-nitrophenyl)vinyl]-7-ethoxy-3-methylimidazo[1,2-a]pyridine (3.8 g) in N,N-dimethylformamide (80 ml) was subjected to catalytic reduction over 10% palladium on carbon (1.9 g) under atmospheric pressure of hydrogen gas at 40° to 60° C. for hours. The catalyst was removed by filtration and the filtrate was evaporated in vacuo. The residue was triturated with a mixture of diethyl ether and diisopropyl ether and the precipitate was collected by filtration to give 2-[2-(4-amino-3-hydroxyphenyl)ethyl]-7-ethoxy-3-methylimidazo[1,2-a]pyridine (1.73 g).

mp: 152°–154° C.

IR (Nujol): 3430, 3350, 1650, 1620, 1590 cm$^{-1}$ (D$_2$O-DCl, δ): 1.53 (3H, t, J=7 Hz), 2.18 (3H, s), 2.87–3.29 (4H, m), 4.28 (2H, q, J=7 Hz), 6.77 (1H, dd, J=2 Hz, 8 Hz), 6.83 (1H, s), 7.02 (1H, dd, J=2 Hz, 7 Hz), 7.12 (1H, d, J=2 Hz), 7.29 (1H, d, J=8 Hz), 8.18 (1H, d, J=7 Hz)

Preparation 65

The following compounds were obtained according to a similar manner to that of Preparation 64.

(1) 2-[2-(4-Amino-3-hydroxyphenyl)ethyl]-7-methoxycarbonyl-3-methylimidazo[1,2-a]pyridine mp: 181°–183° C.

IR (Nujol): 1720, 1600 cm$^{-1}$

NMR (CF$_3$COOH, δ): 2.57 (3H, s), 3.12–3.54 (4H, m), 4.22 (3H, s), 6.82–7.13 (1H, m), 7.04 (1H, s), 7.45 (1H, d, J=8 Hz), 8.12 (1H, d, J=7 Hz), 8.49 (1H, d, J=7 Hz), 8.67 (1H, s)

MASS (m/e): 325 (M$^+$)

(2) 2-[2-(4-Amino-3-hydroxyphenyl)ethyl]-7-carbamoyl-3-methylimidazo[1,2-a]pyridine mp: 76°–79° C.

IR (Nujol): 1650, 1600 cm$^{-1}$

NMR (D$_2$O-DCl, δ): 2.34 (3H, s), 3.04–3.34 (4H, m), 6.67–6.94 (2H, m), 7.24–7.47 (1H, m), 7.78 (1H, dd, J=2 Hz, 7 Hz), 8.29 (1H, d, J=2 Hz), 8.55 (1H, d, J=7 Hz)

MASS (m/e): 310 (M$^+$)

(3) 2-[2-(4-Amino-3-hydroxyphenyl)ethyl]-7-methoxyimidazo[1,2-a]pyridine mp: 94°–104° C.

IR (Nujol): 1650, 1610 cm$^{-1}$ (4) 2-[2-(4-Amino-3-hydroxyphenyl)ethyl]-3-methyl-7-tert-butoxycarbonylaminoimidazo[1,2-a]pyridine mp: 149°–153° C.

IR (Nujol): 3390, 3310, 1710, 1650, 1570 cm$^{-1}$

NMR (DMSO-d$_6$, δ): 1.52 (9H, s), 2.23 (3H, s), 2.76 (4H, s), 6.26–6.78 (3H, m), 7.03 (1H, d, J=7 Hz), 7.64 (1H, s), 8.05 (1H, d, J=7 Hz), 9.61 (1H, s)

(5) 8-Acetylamino-2-[2-(4-amino-3-hydroxyphenyl)ethyl]-3-methylimidazo[1,2-a]pyridine mp: 130°–132° C.

IR (Nujol): 3340, 1690, 1620, 1590 cm$^{-1}$

NMR (DMSO-d$_6$, δ): 2.21 (3H, s), 2.23 (3H, s), 2.58–3.00 (4H, m), 6.32 (1H, d, J=8 Hz), 6.41 (1H, s), 6.46 (1H, d, J=7 Hz), 6.73 (1H, dd, J=each 7 Hz), 7.77 (1H, d, J=7 Hz), 7.81 (1H, d, J=8 Hz), 9.65 (1H, s)

Preparation 66

A mixture of 2-[2-(4-amino-3-hydroxyphenyl)ethyl]-7-methoxy-3-methylimidazo[1,2-a]pyridine (2.5 g) and methyl isocyanate (0.6 ml) in tetrahydrofuran (25 ml) and methanol (2.5 ml) was stirred for 1 hour at ambient temperature. To the reaction mixture was added ethyl acetate (30 ml) and the resulting precipitate was collected by filtration. The precipitate was washed with ethyl acetate and dried to give 2-[2-{3-hydroxy-4-(3-methylureido)phenyl}ethyl]-7-methoxy-3-methylimidazo[1,2-a]pyridine (2.11 g).

mp: 212°–213° C.

IR (Nujol): 3370, 3270, 1650, 1605, 1565 cm$^{-1}$

NMR (CF$_3$COOH, δ): 2.42 (3H, s), 2.88–3.44 (7H, m), 4.09 (3H, s), 6.73–7.52 (5H, m), 7.93–8.28 (1H, m)

Preparation 67

The following compounds were obtained according to a similar manner to that of Preparation 66.

(1) 2-[2-{4-(3-Ethylureido)-3-hydroxyphenyl}ethyl]-7-methoxy-3-methylimidazo[1,2-a]pyridine mp: 211°–213° C.

IR (Nujol): 3360, 3260, 1650, 1630, 1600, 1565 cm$^{-1}$

NMR (CF$_3$COOH, δ): 1.11–1.53 (3H, m), 2.44 (3H, s), 3.18 (4H, s), 3.30–3.85 (2H, m), 4.10 (3H, s), 6.67–7.52 (5H, m), 7.90–8.32 (1H, m)

(2) 2-[2-{4-(3-Allylureido)-3-hydroxyphenyl}ethyl]-7-methoxy-3-methylimidazo[1,2-a]pyridine mp: 184°–186° C.

IR (Nujol): 3360, 3250, 1650, 1600, 1560 cm$^{-1}$

NMR (DMSO-d$_6$, δ): 2.25 (3H, s), 2.86 (4H, s), 3.60–4.00 (2H, m), 3.86 (3H, s), 4.95–5.43 (2H, m), 5.61–6.15 (1H, m), 6.50–6.78 (2H, m), 6.81–7.14 (2H, m), 7.74 (1H, d, J=8 Hz), 8.06 (1H, d, J=7 Hz)

(3) 2-[2-{3-Hydroxy-4-(3-isopropylureido)phenyl}ethyl]-7-methoxy-3-methylimidazo[1,2-a]pyridine mp: 207°–208° C.

IR (Nujol): 3250, 1645, 1600 cm$^{-1}$

Preparation 68

A mixture of 2-[2-(4-amino-3-hydroxyphenyl)ethyl]-7-methoxycarbonyl-3-methylimidazo[1,2-a]pyridine (2.0 g) in tetrahydrofuran (50 ml) was dropwise added to a mixture of lithium aluminum hydride (0.7 g) in tetrahydrofuran (60 ml) at −20°∼−10° C. over 30 minutes and the mixture was stirred at the same temperature for 30 minutes. To the reaction mixture was dropwise added a mixture of water (10 ml) and tetrahydrofuran (20 ml), and the mixture of ethyl acetate, tetrahydrofuran and water was added thereto. The mixture was adjusted to pH 8 with 6N-hydrochloric acid and the insoluble material was removed by filtration. The separated organic layer from filtrate was washed with brine and dried over magnesium sulfate. The solvent was evaporated and the residue was triturated with a mixture of diethyl ether and ethyl acetate to give 2-[2-(4-amino-3-hydroxyphenyl)ethyl]-7-hydroxymethyl-3-methylimidazo[1,2-a]pyridine (1.19 g).

mp: 138°–145° C.

IR (Nujol): 3400, 3330, 1640, 1620, 1600, 1580 cm$^{-1}$

NMR (D$_2$O-DCl, δ): 2.25 (3H, s), 3.13 (4H, m), 4.93 (2H, s), 6.77 (1H, dd, J=2 Hz, 7 Hz), 6.85 (1H, s), 7.31 (1H, d, J=7 Hz), 7.40 (1H, d, J=7 Hz), 7.80 (1H, s), 8.37 (1H, d, J=7 Hz)

MASS (m/e): 297 (M+)

EXAMPLE 54

A mixture of 2-[2-(4-amino-3-hydroxyphenyl)ethyl]-7-methylimidazo[1,2-a]pyridine (1.5 g) and cyanogen bromide (0.7 g) in ethanol (25 ml) was stirred for 2 hours at ambient temperature. To the reaction mixture was added a mixture of ethyl acetate and water, and the mixture was adjusted to pH 1.0 with 10% hydrochloric acid. The separated aqueous layer was adjusted to pH 8.0 with potassium carbonate and the mixture was extracted with a solution of ethyl acetate and tetrahydrofuran. The extract was washed with brine and dried over magnesium sulfate. Evaporation of the solvent gave a residue, which was purified by alumina column chromatography eluting with a solution of chloroform and methanol (19:1, V/V). The fractions containing object compound were concentrated to give 2-amino-6-[2-(7-methylimidazo[1,2-a]pyridin-2-yl)ethyl]benzoxazole (0.44 g).

mp: 262°–264° C.

IR (Nujol): 3130, 3070, 1680, 1580 cm$^{-1}$

NMR (DMSO-d$_6$, δ): 2.32 (3H, s), 2.98 (4H, s), 6.61 (1H, dd, J=2 Hz, 7 Hz), 6.93 (1H, dd, J=2Hz, 8Hz), 7.07 (1H, d, J=8 Hz), 7.10–7.29 (4H, m), 7.51 (1H, s), 8.26 (1H, d, J=7 Hz)

EXAMPLE 55

A mixture of 2-[2-(4amino-3-hydroxyphenyl)ethyl]-7-ethoxy-3-methylimidazo[1,2-a]pyridine (1.6 g) and cyanogen bromide (0.7 g) in ethanol (24 ml) was stirred for 1.5 hours at ambient temperature. The solvent was evaporated in vacuo. To the residue was added a mixture of tetrahydrofuran, ethyl acetate and water, and the mixture was adjusted to pH 8 with 20% aqueous potassium carbonate solution. The separated organic layer was washed with brine and dried over magnesium sulfate. The solvent was evaporated and the residue was triturated with a solution of diethyl ether and ethyl acetate and precipitate was collected by filtration to give 6-[2-(7-ethoxy-3-methylimidazo[1,2-a]pyridin-2-yl)ethyl]-2-aminobenzoxazole (1.12 g).

mp: 207°–208° C.

IR (Nujol): 1665, 1580 cm$^{-1}$

NMR (DMSO-d$_6$, δ): 1.36 (3H, t, J=7 Hz), 2.22 (3H, s), 2.96 (4H, s), 4.11 (2H, q, J=7 Hz), 6.58 (1H, dd, J=2 Hz, 7 Hz), 6.83–7.36 (3H, m), 6.86 (1H, d, J=2 Hz), 7.30 (2H, s), 7.99 (1H, d, J=7 Hz)

EXAMPLE 56

The following compounds were obtained according to a similar manner to that of Example 54 or 55.

(1) 2-Amino-6-[2-(7-methoxycarbonyl-3-methylimidazo[1,2-a]pyridin-2-yl)ethyl]benzoxazole mp: 251°–252° C.

IR (Nujol): 3250, 1710, 1680, 1570 cm$^{-1}$

NMR (DMSO-d$_6$, δ): 2.33 (3H, s), 3.04 (4H, s), 3.92 (3H, s), 6.97–7.10 (2H, m), 7.17–7.45 (4H, m), 8.09 (1H, d, J=2 Hz), 8.25 (1H, d, J=7 Hz)

MASS (m/e): 350 (M+)

(2) 2-Amino-6-[2-(7-hydroxymethyl-3-methylimidazo[1,2-a]pyridin-2-yl)ethyl]-benzoxazole mp: 252°–254° C.

IR (Nujol): 1675, 1570 cm$^{-1}$

NMR (DMSO-d$_6$, δ): 2.25 (3H, s), 2.99 (4H, s), 4.60 (2H, s), 6.85–7.13 (2H, m), 6.87 (1H, dd, J=2 Hz, 7 Hz), 7.13–7.49 (4H, m), 8.11 (1H, d, J=7 Hz)

MASS (m/e): 322 (M+)

(3) 2-Amino-6-[2-(7-carbamoyl-3-methylimidazo[1,2-a]pyridin-2-yl)ethyl]benzoxazole mp: 310°–312° C. (dec.)

IR (Nujol): 3360, 1660, 1560 cm$^{-1}$

NMR (D$_2$O-DCl, δ): 2.31 (3H, s), 3.10–3.34 (4H, m), 7.10–7.53 (3H, m), 7.65–7.90 (1H, m), 8.27 (1H, s), 8.53 (1H, d, J=7 Hz)

MASS (m/e): 335 (M+)

(4) 2-Amino-6-[2-(7-methoxyimidazo[1,2-a]pyridin-2-yl)ethyl]benzoxazole mp: 251°–253° C. IR (Nujol): 1680, 1650, 1580 cm$^{-1}$ NMR (D₂O-DCl, δ): 3.18 (4H, m), 4.04 (3H, s), 7.02 (1H, dd, J=2 Hz, 7 Hz), 7.18 (1H, d, J=2 Hz), 7.37 (2H, s), 7.48 (1H, s), 7.67 (1H, s), 8.42 (1H, d, J=7 Hz)

(5) 2-Amino-6-[2-(3-methyl-7-tert-butoxycarbonylaminoimidazo[1,2-a]pyridin-2-yl)ethyl]benzoxazole mp: 141°–145° C.

IR (Nujol): 1720, 1660, 1570 cm⁻¹

NMR (DMSO-d₆, δ): 1.49 (9H, s), 2.16 (3H, s), 2.89 (4H, s), 6.93 (1H, dd, J=7 Hz), 7.01 (1H, d, J=8 Hz), 7.14 (1H, d, J=8 Hz), 7.16 (1H, s), 7.54 (1H, s), 7.96 (1H, d, J=7 Hz), 9.50 (1H, s)

(6) 6-[2-(8-Acetamido-3-methylimidazo[1,2-a]pyridin-2-yl)ethyl]-2-aminobenzoxazole mp: 220°–221° C.

IR (Nujol): 1675, 1580, 1555 cm⁻¹

NMR (DMSO-d₆, δ): 2.22 (6H, s), 2.96 (4H, s), 6.75 (1H, dd, J=each 7 Hz), 6.84 (1H, dd, J=2 Hz, 8 Hz), 7.03 (1H, d, J=8 Hz), 7.08 (1H, s), 7.16 (2H, s), 7.78 (1H, d, J=7 Hz), 7.83 (1H, d, J=7 Hz), 9.68 (1H, s)

MASS (m/e): 349 (M+)

EXAMPLE 57

A solution of acetyl chloride (1.94 g) in dichloromethane (6 ml) was added dropwise to a solution of 2-amino-6-[2-(7-methylimidazo[1,2-a]pyridin-2-yl)ethyl]benzoxazole (6.00 g) and pyridine (4.92 ml) in dichloromethane (60 ml) with stirring at 0° C. The mixture was stirred for two hours at the same temperature and further 22 hours at ambient temperature. Saturated aqueous sodium hydrogen carbonate solution (100 ml) was added thereto and that was stirred for 2.5 hours at 0° C. The resulting precipitate was collected by filtration and washed with water. Recrystallization from a mixture of ethanol and diethyl ether gave 2-acetylamino-6-[2-(7-methylimidazo[1,2-a]pyridin-2-yl)ethyl]benzoxazole (4.00 g).

mp: 197°–198° C.

IR (Nujol): 3125, 1700, 1625 cm⁻¹

NMR (DMSO-d₆, δ): 2.22 (3H, s), 2.33 (3H, s), 3.07 (4H, s), 6.65 (1H, dd, J=2 Hz and 7 Hz), 7.08–7.55 (5H, m), 8.29 (1H, d, J=7 Hz), 11.50 (1H, br s)

EXAMPLE 58

The following compounds were obtained according to a similar manner to that of Example 57.

(1) 6-[2-(7-Methylimidazo[1,2-a]pyridin-2-yl)ethyl]-2-propionylaminobenzoxazole mp: 196°–198° C. (recrystallized from a mixture of ethanol and diisopropyl ether)

IR (Nujol): 3125, 1730, 1615 cm⁻¹

NMR (DMSO-d₆, δ): 1.10 (3H, q, J=7 Hz), 2.35 (3H, s), 2.58 (2H, q, J=7 Hz), 3.08 (4H, s), 6.68 (1H, dd, J=1.5 Hz and 7 Hz), 7.22 (1H, dd, J=2 Hz and 8 Hz), 7.25 (1H, d, J=2 Hz), 7.48 (1H, d, J=8 Hz), 7.50 (1H, d, J=1.5 Hz), 7.57 (1H, s), 8.33 (1H, d, J=7 Hz), 11.42 (1H, br s)

(2) 2-Butyrylamino-6-[2-(7-methylimidazo[1,2-a]pyridin-2-yl)ethyl]benzoxazole mp: 200°–201° C. (recrystallized from a mixture of ethanol and n-hexane)

IR (Nujol): 3130, 1725, 1635 cm⁻¹

NMR (DMSO-d₆, δ): 0.93 (3H, t, J=7 Hz), 1.37–1.97 (2H, m), 2.35 (3H, s), 2.53 (2H, t, J=7 Hz), 3.10 (4H, s), 6.67 (1H, dd, J=1.5 Hz and 7 Hz), 7.20 (1H, dd, J=2 Hz and 8 Hz), 7.27 (1H, d, J=2 Hz), 7.50 (1H, d, J=8 Hz), 7.52 (1H, d, J=1.5 Hz), 7.58 (1H, s), 8.33 (1H, d, J=7 Hz), 11.33 (1H, br s)

(3) 2-Isobutyrylamino-6-[2-(7-methylimidazo[1,2-a]pyridin-2-yl)ethyl]benzoxazole mp 208°–209° C. (recrystallized from a mixture of methanol and diisopropyl ether)

IR (Nujol): 3140, 3075, 1720, 1635, 1610 cm⁻¹

NMR (DMSO-d₆, δ): 1.13 (6H, d, J=7 Hz), 2.33 (3H, s), 2.72–3.22 (1H, m), 3.08 (4H, s), 6.67 (1H, dd, J=1.5 Hz and 7 Hz), 7.18 (1H, dd, J=2 Hz and 8 Hz), 7.25 (1H, d, J=2 Hz), 7.48 (1H, d, J=8 Hz), 7.50 (1H, d, J=1.5 Hz), 7.57 (1H, s), 8.32 (1H, d, J=7 Hz), 11.10 (1H, br s)

(4) 6-[2-(7-Methylimidazo[1,2-a]pyridin-2-yl)ethyl]-2-pivaloylaminobenzoxazole mp: 201°–202° C. (recrystallized from a mixture of methanol and diisopropyl ether)

IR (Nujol): 3140, 1705, 1635 cm⁻¹

NMR (DMSO-d₆, δ): 1.28 (9H, s), 2.35 (3H, s), 3.10 (4H, s), 6.67 (1H, dd, J=1.5 Hz and 7 Hz), 7.22 (1H, dd, J=2 Hz and 8 Hz), 7.27 (1H, d, J=2 Hz), 7.50 (1H, d, J=8 Hz), 7.52 (1H, d, J=1.5 Hz), 7.57 (1H, s), 8.35 (1H, d, J=7 Hz), 10.92 (1H, br s)

(5) 2-Cyclopropylcarbonylamino-6-[2-(7-methylimidazo[1,2-a]pyridin-2-yl)ethyl]benzoxazole mp: 203° to 204° C. (recrystallized from a mixture of ethanol and n-hexane)

IR (Nujol): 3140, 3075, 1715, 1630, 1615 cm⁻¹

NMR (DMSO-d₆, δ): 0.93 (4H, d, J=6 Hz), 2.07 (1H, quint, J=6 Hz), 2.33 (3H, s), 3.06 (4H, s), 6.64 (1H, dd, J=1.5 Hz and 7 Hz), 7.17 (1H, dd, J=2 Hz and 8 Hz), 7.23 (1H, d, J=2 Hz), 7.44 (1H, d, J=8 Hz), 7.47 (1H, d, J=1.5 Hz), 7.55 (1H, s), 8.30 (1H, d, J=7 Hz)

(6) 2-((S)-2-Acetoxypropionyl)amino-6-[2-(7-methylimidazo[1,2-a]pyridin-2-yl)ethyl]benzoxazole mp: 217°–218° C. (recrystallized from a mixture of methanol and diisopropyl ether)

IR (Nujol): 3140, 3080, 1730, 1720, 1640, 1615 cm⁻¹

NMR (DMSO-d₆, δ): 1.45 (3H, d, J=7 Hz), 2.10 (3H, s), 2.33 (3H, s), 2.81–3.17 (5H, m), 5.00–5.30 (1H, m), 6.64 (1H, dd, J=1.5 Hz and 7 Hz), 7.19 (1H, dd, J=2 Hz and 8 Hz), 7.23 (1H, d, J=2 Hz), 7.46 (1H, d, J=8 Hz), 7.49 (1H, d, J=1.5 Hz), 7.53 (1H, s) and 8.29 (1H, d, J=7 Hz)

(7) 2-Acetylamino-6-[2-(3,7-dimethylimidazo[1,2-a]pyridin-2-yl)ethyl]benzoxazole mp: 205°–207° C.

IR (Nujol): 1725, 1685, 1640, 1620 cm⁻¹

NMR (DMSO-d₆, δ): 2.21 (6H, s), 2.45 (3H, s), 3.01 (4H, m), 6.73 (1H, dd, J=2 Hz, 7 Hz), 7.09 (1H, dd, J=2 Hz, 8 Hz), 7.25 (1H, d, J=2 Hz), 7.40 (1H, d, J=8 Hz), 7.40 (1H, d, J=2 Hz), 8.02 (1H, d, J=7 Hz)

(8) 2-Acetylamino-6-[2-(7-methoxy-3-methylimidazo[1,2-a]pyridin-2-yl)ethyl]benzoxazole mp 229°–232° C.

IR (Nujol): 1725, 1645, 1585 cm⁻¹

NMR (DMSO-d₆, δ): 2.20 (3H, s), 2.22 (3H, s), 3.04 (4H, s), 3.90 (3H, s), 6.83 (1H, dd, J=2 Hz, 7 Hz), 7.00 (1H, d, J=2 Hz), 7.11 (1H, d, J=8 Hz), 7.40 (1H, d, J=8 Hz), 7.45 (1H, s), 8.20 (1H, d, J=7 Hz)

(9) 2-Acetylamino-6-[2-(7-methoxyimidazo[1,2-a]pyridin-2-yl)ethyl]benzoxazole mp 181°–182° C.

IR (Nujol): 1700, 1640, 1620, 1570 cm⁻¹

NMR (DMSO-d₆, δ): 2.23 (3H, s), 3.06 (4H, s), 3.82 (3H, s), 6.54 (1H, dd, J=2 Hz, 7 Hz), 6.87 (1H, d, J=2 Hz), 7.18 (1H, dd, J=2 Hz, 8 Hz), 7.47 (2H, s), 7.48 (1H, d, J=8 Hz), 8.28 (1H, d, J=7 Hz), 11.42 (1H, br s)

MASS (m/e): 350 (M+)

(10) 6-[2-(7-Methoxyimidazo[1,2-a]pyridin-2-yl)ethyl]-2-pivaloylaminobenzoxazole mp: 209°–210° C.

IR (Nujol): 3140, 1685, 1645, 1610, 1570 cm$^{-1}$

NMR (DMSO-d$_6$, δ): 1.25 (9H, s), 3.06 (4H, s), 3.82 (3H, s), 6.53 (1H, dd, J=2 Hz, 7 Hz), 6.87 (1H, d, J=2 Hz), 7.21 (1H, dd, J=2 Hz, 8 Hz), 7.45 (2H, s), 7.49 (1H, d, J=8 Hz), 8.27 (1H, d, J=7 Hz), 10.88 (1H, br s)

Mass (m/e): 392 (M+)

(11) 2-Cyclohexylcarbonylamino-6-[2-(7-methylimidazo[1,2-a]pyridin-2-yl)ethyl]benzoxazole mp: 125°–126° C.

IR (Nujol): 1725, 1620, 1560 cm$^{-1}$

NMR (DMSO-d$_6$, δ): 0.98–2.14 (10H, m), 2.36 (3H, 3), 3.08 (4H, s), 3.30–3.57 (1H, m), 6.70 (1H, dd, J=2 Hz, 7 Hz), 7.21 (1H, d, J=8 Hz), 7.27 (1H, s), 7.38–7.68 (3H, m), 8.33 (1H, d,

MASS (m/e): 402 (M+)

(12) 2-(2-Ethylbutyryl)amino-6-[2-(7-methylimidazo[1,2-a]pyridin-2-yl)ethyl]benzoxazole mp 214°–215° C.

IR (Nujol): 3150, 1720, 1620, 1560 cm$^{-1}$

NMR (DMSO-d$_6$, δ): 0.87 (6H, t, J=7 Hz), 1.26–1.91 (4H, m), 2.35 (3H, s), 3.10 (4H, s), 3.30–3.52 (1H, m,), 6.69 (1H, dd, J=2 Hz, 7 Hz), 7.20 (1H, d, J=7 Hz), 7.29 (1H, s), 7.43–7.70 (3H, m), 8.35 (1H, d, J=7 Hz), 11.40 (1H, br s)

MASS (m/e): 390 (M+)

(13) 2-Acetylamino-6-[2-(3,8-dimethylimidazo[1,2-a]pyridin-2-yl)ethyl]benzoxazole mp 150°–152° C.

IR (Nujol): 1720, 1640, 1580 cm$^{-1}$

NMR (DMSO-d$_6$, δ): 2.23 (3H, s), 2.26 (3H, s), 2.52 (3H, s), 3.06 (4H, s), 6.80 (1H, dd, J=each 7 Hz), 6.93–7.30 (2H, m), 7.47 (1H, d, J=7 Hz), 7.51 (1H, s), 8.01 (1H, d, J=7 Hz), 11.36 (1H, br s)

MASS (m/e): 348 (M+)

(14) 2-Acetylamino-6-[2-(7-methoxy-3-methylimidazo[1,2-a]pyridin-2-yl)ethyl]benzothiazole mp 240°–242° C.

IR (Nujol): 1685, 1650, 1610, 1545 cm$^{-1}$

NMR (DMSO-d$_6$, δ): 2.22 (6H, s), 3.03 (4H, s), 3.85 (3H, s), 6.64 (1H, dd, J=2 Hz, 7 Hz), 6.94 (1H, d, J=2 Hz), 7.29 (1H, dd, J=2 Hz, 8 Hz), 7.67 (1H, d, J=8 Hz), 7.81 (1H, s), 8.05 (1H, d, J=7 Hz)

MASS (m/e): 380 (M+)

EXAMPLE 59

A mixture of 2-[2-{3-hydroxy-4-(3-methylureido)phenyl}ethyl]-7-methoxy-3-methylimidazo[1,2-a]pyridine (1.9 g) and polyphosphate ester (15 g) was stirred for 1.5 hours at 130° C. To the reaction mixture was added a mixture of ethyl acetate and water, and the mixture was adjusted to pH 1 with 6N hydrochloric acid. The separated aqueous layer was adjusted to pH 8 with aqueous potassium carbonate solution. The aqueous mixture was extracted with a mixture of ethyl acetate and tetrahydrofuran with salting-out technique. The extract was washed with brine and dried over magnesium sulfate. Evaporation of the solvent gave a residue, which was triturated with a mixture of diethyl ether and ethyl acetate, and the resulting precipitate was crystallized from a mixture of methanol, ethyl acetate and isopropyl ether to give 6-[2-(7-methoxy-3-methylimidazo[1,2-a]pyridin-2-yl)ethyl]-2-methylaminobenzoxazole (0.26 g).

mp: 203°–205° C.

IR (Nujol): 3160, 1660, 1585 cm$^{-1}$

NMR (DMSO-d$_6$, δ): 2.20 (3H, s), 2.92 (3H, d, J=5 Hz), 2.95 (4H, s), 3.84 (3H, s), 6.62 (1H, dd, J=2 Hz, 7 Hz), 6.84–7.15 (2H, m), 7.16 (1H, d, J=8 Hz), 7.19 (1H, s), 7.63 (1H, t, J=5 Hz), 8.03 (1H, d, J=7 Hz)

MASS (m/e): 336 (M+)

EXAMPLE 60

The following compounds were obtained according to a similar manner to that of Example 59.

(1) 2-Ethylamino-6-[2-(7-methoxy-3-methylimidazo[1,2-a]pyridin-2-yl)ethyl]benzoxazole mp: 169°–171° C.

IR (Nujol): 3160, 1640, 1580 cm$^{-1}$

NMR (DMSO-d$_6$, δ): 1.17 (3H, t, J=7 Hz), 2.17 (3H, s), 2.91 (4H, s), 3.13–3.47 (2H, m), 3.79 (3H, s), 6.55 (1H, dd, J=2 Hz, 7 Hz), 6.87 (1H, d, J=2 Hz), 6.87 (1H, d, J=8 Hz), 7.07 (1H, d, J=8 Hz), 7.12 (1H, s), 7.72 (1H, t, J=5 Hz), 7.97 (1H, d, J=7 Hz)

(2) 2-Allylamino-6-[2-(7-methoxy-3-methylimidazo[1,2-a]pyridin-2-yl)ethyl]benzoxazole mp: 177°–180° C.

IR (Nujol): 1650, 1580 cm$^{-1}$

NMR (DMSO-d$_6$, δ): 2.22 (3H, s), 2.97 (4H, s), 3.70–4.15 (2H, m), 3.85 (3H, s), 5.00–5.46 (2H, m), 5.62–6.38 (1H, m), 6.65 (1H, dd, J=2 Hz, 7 Hz), 6.85–7.26 (3H, m), 7.22 (1H, s), 8.06 (1H, d, J=7 Hz)

(3) 2-Isopropylamino-6-[2-(7-methoxy-3-methylimidazo[1,2-a]pyridin-2-yl)ethyl]benzoxazole mp: 121°–124° C.

IR (Nujol): 1640, 1575 cm$^{-1}$

EXAMPLE 61

A mixture of 2-amino-6-[2-(7-methoxycarbonyl-3-methylimidazo[1,2-a]pyridin-2-yl)ethyl]benzoxazole (0.8 g) in methanol (8 ml) and 1N sodium hydroxide (6.8 ml) was stirred for 20 hours at ambient temperature. To the reaction mixture was added a water and the mixture was adjusted to pH 5 with 4N-hydrochloric acid. The isolated precipitate was collected by filtration and dried to give 2-amino-6-[2-(7-carboxy-3-methylimidazo[1,2-a]pyridin-2-yl)ethyl]benzoxazole (0.24 g).

mp: >350° C.

IR (Nujol): 3280, 1690 cm$^{-1}$

NMR (CF$_3$COOH, δ): 2.60 (3H, s), 3.40 (4H, s), 7.21–7.64 (3H, m), 8.16 (1H, d, J=7 Hz), 8.52 (1H, d, J=7 Hz), 8.69 (1H, s)

MASS (m/e): 336 (M+)

EXAMPLE 62

A mixture of 2-amino-6-[2-(7-hydroxymethyl-3-methylimidazo[1,2-a]pyridin-2-yl)ethyl]benzoxazole (0.5 g) and thionyl chloride (5 ml) was stirred for 40 minutes under ice-cooling. The reaction mixture was poured into ice-water and the mixture was adjusted to pH 8 with 20% aqueous potassium carbonate solution. The aqueous mixture was extracted with a mixture of tetrahydrofuran and ethyl acetate. The extract was washed with brine and dried over magnesium sulfate. The solvent was evaporated and triturated with diethyl ether to give 2-amino-6-[2-(7-chloromethyl-3-methylimidazo[1,2-a]pyridin-2-yl)ethyl]benzoxazole (0.42 g).

mp: >300° C.

IR (Nujol): 1675, 1615, 1570 cm$^{-1}$

NMR (D$_2$O-DCl, δ): 2.31 (3H, s), 3.23 (4H, s), 4.94 (2H, s), 7.21 (1H, d, J=7 Hz), 7.23–7.48 (2H, m), 7.58 (1H, dd, J=2 Hz, 7 Hz), 7.95 (1H, s), 8.45 (1H, d, J=7 Hz)

EXAMPLE 63

A mixture of 2-amino-6-[2-(7-chloromethyl-3-methylimidazo[1,2-a]pyridin-2-yl)ethyl]benzoxazole (0.4 g), and sodium methoxide (0.13 g) in methanol (10 ml) was stirred for 3 hours at 40°-50° C. and the solvent was evaporated in vacuo. The residue was dissolved in a mixture of ethyl acetate and tetrahydrofuran and the mixture was washed with water and dried over magnesium sulfate. Evaporation of the solvent gave a residue, which was purified by silica gel column chromatography eluting with a solution of chloroform and methanol (9:V/V). The fraction containing object compound were concentrated to give 2-amino-6-[2-(7-methoxymethyl-3-methylimidazo[1,2-a]pyridin-2-yl)ethyl]benzoxazole (0.22 g).

mp: 206°-207° C.

IR (Nujol): 1670, 1570 cm$^{-1}$

NMR (D$_2$O-DCl, $\delta$): 2.26 (3H, s), 3.17 (4H, m), 3.52 (3H, s), 4.73 (2H, s), 7.16 (1H, d, J=8 Hz), 7.19 (1H, d, J=8 Hz), 3.34 (1H, s), 7.36 (1H, dd, J=2 Hz, 8 Hz), 7.72 (1H, s), 8.32 (1H, d, J=8 Hz)

MASS (m/e): 336 (M+)

EXAMPLE 64

A mixture of 2-amino-6-[2-(7-chloromethyl-3-methylimidazo[1,2-a]pyridin-2-yl)ethyl]benzoxazole (1.3 g), sodium azide (0.5 g) and potassium azide (1.3 g) in N,N-dimethylformamide (26 ml) was stirred for 17 hours at ambient temperature and the mixture was poured into water. The mixture was extracted with a mixture of ethyl acetate and tetrahydrofuran. The extract was washed with brine and dried over magnesium sulfate. The solvent was evaporated and the residue was triturated with diethyl ether to give 2-amino-6-[2-(7-azidomethyl-3-methylimidazo[1,2-a]pyridin-2-yl)ethyl]benzoxazole (1.21 g).

mp: 205°-208° C. (dec.)

IR (Nujol): 2100, 1670, 1570 cm$^{-1}$

NMR (DMSO-d$_6$, $\delta$): 2.26 (3H, s), 2.97 (4H, s), 4.49 (2H, s), 6.70-7.02 (2H, x, 7.04 (1H, d, J=8 Hz), 7.12 (1H, s), 7.19 (2H, s), 7.45 (1H, s), 8.11 (1H, d, J=7 Hz)

MASS (m/e): 347 (M+)

EXAMPLE 65

10% Palladium on carbon (0.3 g) was added to a solution of 2-amino-6-[2-(7-azidomethyl-3-methylimidazo[1,2-a]pyridin-2-yl)ethyl]benzoxazole (1.0 g) in methanol (100 ml) and the mixture was subjected to catalytic reduction at ambient temperature under atmospheric pressure of hydrogen gas. The catalyst was removed by filtration and the filtrate was evaporated in vacuo. The residue was purified by alumina column chromatography eluting with a solution of chloroform and methanol (4:1, V/V). The fractions containing object compound was evaporated to give 2-amino-6-[2-(7-aminomethyl-3-methylimidazo[1,2-a]pyridin-2-yl)ethyl]benzoxazole (0.41 g).

mp 218°-221° C.

IR (Nujol): 1680, 1570 cm$^{-1}$

NMR (DMSO-d$_6$, $\delta$): 2.21 (3H, s), 2.93 (4H, s), 3.72 (2H, s), 6.78 (1H, d, J=7 Hz), 6.83 (1H, d, J=8 Hz), 7.00 (1H, d, J=8 Hz), 7.07 (1H, s), 7.16 (2H, s), 7.30 (1H, s), 7.96 (1H, d, J=7 Hz)

MASS (m/e): 321 (M+)

EXAMPLE 66

A mixture of 2-amino-6-[2-(7-methoxyimidazo[1,2-a]pyridin-2-yl)ethyl]benzoxazole (1.0 g) and N-chlorosuccinimide (0.43 g) in dioxane (15 ml) was stirred for 2 hours at ambient temperature. To the reaction mixture was added a mixture of ethyl acetate and water, and the mixture was adjusted to pH 1 with 6N hydrochloric acid. The separated aqueous layer was adjusted to pH 8 with 20% potassium carbonate aqueous solution and the mixture was extracted with a mixture of ethyl acetate and tetrahydrofuran. The extract was washed with brine and dried over magnesium sulfate. Evaporation of the solvent gave a residue, which was purified by silica gel column chromatography eluting with a solution of chloroform and methanol (19:1, V/V). The fractions containing object compound were concentrated to give 2-amino-6-[2-(3-chloro-7-methoxyimidazo[1,2-a]pyridin-2-yl)ethyl]benzoxazole (0.41 g).

mp: 225°-227° C.

IR (Nujol): 1690, 1650, 1575 cm$^{-1}$

NMR (D$_2$O-DCl, $\delta$): 3.23 (4H, s), 4.08 (3H, s), 7.18 (1H, dd, J=2 Hz, 7 Hz), 7.25-7.40 (3H, m), 7.46 (1H, s), 8.36 (1H, d, J=7 Hz)

MASS (m/e): 342 (M+)

EXAMPLE 67

A mixture of 2-amino-6-[2-(7-methoxy-3-methylimidazo[1,2-a]pyridin-2-yl)ethyl]benzoxazole dihydrochloride (2.0 g) in 1N hydrochloric acid (25.3 ml) was was refluxed for 21 hours. The reaction mixture was added to water (50 ml) under ice-cooling and the resulting precipitate was collected by filtration. A mixture of obtained residue and water was adjusted to pH 8 with 20% potassium carbonate aqueous solution under stirring. A precipitate was collected by filtration and dried to give 2-hydroxy-6-[2-(7-methoxy-3-methylimidazo[1,2-a]pyridin-2-yl)ethyl]benzoxazole (0.98 g).

mp: 255°-257° C.

IR (Nujol): 1750 (br), 1650 cm$^{-1}$

NMR (CF$_3$COOH, $\delta$): 2.37 (3H, s), 3.25 (4H, s), 4.11 (3H, s), 7.05-7.52 (5H, m), 8.16 (1H, d, J=7 Hz), 9.75 (1H, s)

MASS (m/e): 323 (M+)

EXAMPLE 68

The mixture of 2-amino-6-[2-(7-methoxy-3-methylimidazo[1,2-a]pyridin-2-yl)ethyl]benzothiazole (2.3 g) and boron tribromide (6.4 ml) in dichloromethane (115 ml) was stirred for 20 hours at ambient temperature and the solvent was evaporated in vacuo. A mixture of obtained residue and water was adjusted to pH 7.5 with 20% potassium carbonate aqueous solution and resulting precipitate was collected by filtration and dried. The residue was purified by alumina column chromatography eluting with a solution of chloroform and methanol (4:1, V/V). The fractions containing object compound were concentrated in vacuo. To a mixture of obtained residue and ethanol (3 ml) was added conc. hydrochloric acid (0.2 ml) and the mixture was stirred for 30 minutes at ambient temperature. The resulting precipitate was collected by filtration and dried to give 2-amino-6-[2-(7-hydroxy-3-methylimidazo[1,2-a]pyridin-2-yl)ethyl]benzothiazole dihydrochloride (0.22 g).

mp: 265°-266° C.

IR (Nujol): 1670, 1655, 1605, 1580 cm$^{-1}$

NMR (D$_2$O, $\delta$): 2.14 (3H, s), 3.05 (4H, s), 6.91-7.23 (2H, m), 7.27-7.56 (3H, m), 8.17 (1H, d, J=8 Hz)

MASS (m/e): 324 (M+)

EXAMPLE 69

The mixture of 2-amino-6-[2-(3-methyl-7-tertbutoxycarbonylaminoimidazo[1,2-a]pyridin-2-yl)ethyl]benzoxazole (0.8 g) and conc. hydrochloric acid (0.9 ml) in ethanol (20 ml) was heated under refluxed for 1 hour. The mixture was ice-cooling and the isolated precipitate was collected by filtration. To a precipitate was added a mixture of ethyl acetate, tetrahydrofuran and water, and the mixture was adjusted to pH 8.5 with 20% aqueous potassium carbonate solution with salting-out technique. The separated organic layer was washed with brine and dried over magnesium sulfate. Evaporation of the solvent gave a residue, which was triturated with a solution of ethyl acetate and diethyl ether, and the precipitate was collected by filtration to give 2-amino-6-[2-(7-amino-3-methylimidazo[1,2-a]pyridin-2-yl)ethyl]benzoxazole (0.24 g).

mp: 221°-223° C.

IR (Nujol): 3370, 3220, 1680, 1650, 1575 cm$^{-1}$

NMR (DMSO-d$_6$, δ): 2.12 (3H, s), 2.84 (4H, s), 5.47 (2H, br s), 6.18-6.40 (1H, m), 6.29 (1H, s), 6.84 (1H, dd, J=2 Hz, 8 Hz), 6.85-7.20 (2H, m), 7.16 (2H, s), 7.71 (1H, d, J=8 Hz)

MASS (m/e): 307 (M+)

EXAMPLE 70

A mixture of 6-[2-(8-acetylamino-3-methylimidazo[1,2-a]pyridin-2-yl)ethyl]-2-aminobenzoxazole (0.6 g) and conc. hydrochloric acid (0.76 ml) in ethanol (12 ml) was refluxed for 7 hours. To the reaction mixture was added ethyl acetate (18 ml) and the resulting precipitate was collected by filtration. A solution of resulting precipitate in water was adjusted to pH 9.0 with 20% aqueous potassium carbonate solution and the precipitate was collected by filtration and dried to give 2-amino-6-[2-(8-amino-3-methylimidazo[1,2-a]pyridin-2-yl)ethyl]benzoxazole (0.45 g).

mp: 201°-202° C.

IR (Nujol) 3430, 3330, 3270, 1680, 1615, 1570, 1550 cm$^{-1}$

NMR (DMSO-d$_6$, δ): 2.18 (3H, s), 2.93 (4H, s), 5.42 (2H, br s), 6.16 (1H, d, J=7 Hz), 6.55 (1H, dd, J=each 7 Hz), 6.85 (1H, d, J=8 Hz), 6.90-7.20 (2H, m), 7.15 (2H, s), 7.31 (1H, d, J=7 Hz)

MASS (m/e): 307 (M+)

EXAMPLE 71

Conc. hydrochloric acid (0.6 ml) was added to a solution of 6-[2-(7-ethoxy-3-methylimidazo[1,2-a]pyridin-2-yl)ethyl]-2-aminobenzoxazole (1.0 g) in ethanol (6.0 ml) and the mixture was stirred for 1 hour at ambient temperature. The mixture was added to ethyl acetate (40 ml) and stirred. The resulting precipitate was collected by filtration and the residue was crystallized from a mixture of ethanol (6 ml) and ethyl acetate (3 ml) to give 6-[2-(7-ethoxy-3-methylimidazo[1,2-a]pyridin-2-yl)ethyl]-2-aminobenzoxazole dihydrochloride (0.92 g).

mp: 266°-268° C.

IR (Nujol): 3350 (br), 1707, 1668, 1630, 1540 cm$^{-1}$

NMR (D$_2$O, δ): 1.52 (3H, t, J=7 Hz), 2.18 (3H, s), 3.10 (4H, s), 4.28 (2H, q, J=7 Hz), 6.90-7.16 (1H, m), 7.08 (1H, s), 7.17-7.44 (3H, m), 8.17 (1H, d, J=7 Hz)

EXAMPLE 72

The following compounds were obtained according to a similar manner to that of Example 71.

(1) 2-Amino-[2-(7-methylimidazo[1,2-a]pyridin-2-yl)ethyl]benzoxazole dihydrochloride.

mp: 115°-117° C.

IR (Nujol): 1710, 1660 (br) cm$^{-1}$

NMR (D$_2$O, δ): 2.62 (3H, s), 3.26 (4H, s), 7.27 (1H, d, J=7 Hz), 7.33 (2H, s), 7.45 (1H, s), 7.59 (1H, s), 7.71 (1H, s), 7.41 (1H, d, J=7 Hz)

(2) 2-Amino-6-[2-(7-hydroxymethyl-3-methylimidazo[1,2-a]pyridin-2-yl)ethyl]benzoxazole dihydrochloride mp: 256°-257° C.

IR (Nujol): 3300, 1720, 1660, 1630 cm$^{-1}$

NMR (D$_2$O, δ): 2.22 (3H, s), 3.21 (4H, s), 4.1 (2H, s), 7.12 (1H, dd, J=2 Hz, 7 Hz), 7.17-7.43 (2H, m), 7.41 (1H, dd, J=2 Hz, 8 Hz), 7.77 (1H, d, J=2 Hz), 8.34 (1H, d, J=7 Hz)

(3) 2-Amino-6-[2-(7-carbamoyl-3-methylimidazo[1,2-a]pyridin-2-yl)ethyl]benzoxazole dihydrochloride mp: >300° C.

IR (Nujol): 1715, 1670, 1605 cm$^{-1}$

NMR (D$_2$O, δ): 2.32 (3H, s), 3.17-3.36 (4H, m), 7.05-7.44 (3H, m), 7.78 (1H, dd, J=2 Hz, 7 Hz), 8.28 (1H, d, J=2 Hz), 8.53 (1H, d, J=7 Hz)

MASS (m/e): 335 (M+)

(4) 6-[2-(7-Methoxy-3-methylimidazo[1,2-a]pyridin-2-yl)ethyl]-2-methylaminobenzoxazole dihydrochloride mp: 244°-246° C.

IR (Nujol): 1710, 1665, 1540 cm$^{-1}$

NMR (D$_2$O, δ): 2.20 (3H, s), 3.14 (4H, s), 3.23 (3H, s), 4.04 (3H, s), 7.01 (1H, dd, J=2 Hz, 7 Hz), 7.10 (1H, s), 7.12 (1H, dd, J=2 Hz, 8 Hz), 7.28 (1H, d, J=8 Hz), 7.32 (1H, s), 8.14 (1H, d, J=7 Hz)

MASS (m/e): 336 (M+)

(5) 2-Ethylamino-6-[2-(7-methoxy-3-methylimidazo[1,2-a]pyridin-2-yl)ethyl]benzoxazole dihydrochloride mp: 169°-171° C.

IR (Nujol): 3500, 3400, 3300, 3260, 1700, 1675, 1640, 1540 cm$^{-1}$

NMR (D$_2$O, δ): 1.44 (3H, t, J=7 Hz) 3.14 (4H, s), 3.65 (2H, q, J=7 Hz), 4.06 (3H, s), 7.06 (1H, dd, J=2 Hz, 7 Hz), 7.13-7.43 (4H, m), 8.23 (1H, d, J=7 Hz)

MASS (m/e): 350 (M+)

(6) 2-Allylamino-6-[2-(7-methoxy-3-methylimidazo[1,2-a]pyridin-2-yl)ethyl]benzoxazole dihydrochloride mp: 192°-194° C.

IR (Nujol) 3430, 1700, 1670, 1640 cm$^{-1}$

NMR (D$_2$O, δ): 2.21 (3H, s), 3.13 (4H, s), 4.03 (3H, s), 4.19 (2H, d, J=5 Hz), 5.20-5.59 (2H, m), 5.80-6.31 (1H, m), 7.00 (1H, dd, J=2 Hz, 7 Hz), 7.00-7.27 (2H, m), 7.28 (1H, d, J=8 Hz), 7.30 (1H, s), 8.13 (1H, d, J=7 Hz)

(7) 2-Isopropylamino-6-[2-(7-methoxy-3-methylimidazo[1,2-a]pyridin-2-yl)ethyl]benzoxazole dihydrochloride mp: 144°-145° C.

IR (Nujol): 3350, 1695, 1670, 1640 cm$^{-1}$

NMR (D$_2$O, δ): 1.46 (6H, d, J=7 Hz), 2.21 (3H, s), 3.15 (4H, s), 3.82-4.24 (1H, m), 4.03 (3H, s), 7.01 (1H, dd, J=2 Hz, 7 Hz), 7.05-7.32 (3H, m), 7.29 (1H, s), 8.14 (1H, d, J=7 Hz)

(8) 2-Amino-5-[2-(7-methoxy-3-methylimidazo[1,2-a]pyridin-2-yl)ethyl]-1H-benzimidazole dihydrochloride mp: 244°-246° C.

IR (Nujol): 3340 (br), 1685, 1635 (br) cm$^{-1}$

NMR (D$_2$O, δ): 2.23 (3H, s), 3.12 (4H, s), 4.11 (3H, s), 6.97-7.27 (4H, m), 7.28 (1H, d, J=8 Hz), 8.20 (1H, d, J=7 Hz)

EXAMPLE 73

The following compounds were obtained according to a similar manner to that of Example 54 or 55.

(1) 2-Amino-6-[2-(3-methylimidazo[1,2-a]pyridin-2-yl)ethyl]benzoxazole mp: 229°–231° C.

IR (Nujol): 1680, 1620, 1570 cm$^{-1}$

NMR (DMSO-$d_6$, δ): 2.27 (3H, s), 3.00 (4H, s), 6.80 (1H, d, J=2 Hz, 7 Hz), 6.94–7.12 (2H, m), 7.00–7.40 (4H, m), 7.52 (1H, d, J=8 Hz), 8.14 (1H, d, J=6 Hz)

(2) 2-Amino-6-[2-(3,6-dimethylimidazo[1,2-a]pyridin-2-yl)ethyl]benzoxazole mp: 83°–85° C.

IR (Nujol): 1680, 1580 cm$^{-1}$

NMR (DCl-$D_2O$, δ): 2.26 (3H, s), 2.46 (3H, s), 3.13 (4H, s), 7.14 (1H, d, J=8 Hz), 7.29 (1H, d, J=8 Hz), 7.35 (1H, s), 7.68 (2H, s), 8.14 (1H, s)

(3) 2-Amino-6-[2-(3,8-dimethylimidazo[1,2-a]pyridin-2-yl)ethyl]benzoxazole mp: 115° C.

IR (Nujol): 1672, 1610, 1567 cm$^{-1}$

NMR (DMSO-$d_6$, δ): 2.25 (3H, s), 2.49 (3H, s), 2.97 (4H, s), 6.73 (1H, dd, J=each 7 Hz), 6.83–7.06 (2H, m), 7.07 (1H, d, J=8 Hz), 7.08–7.35 (3H, m), 7.93 (1H, d, J=7 Hz)

(4) 2-Amino-6-[2-(7-ethyl-3-methylimidazo[1,2-a]pyridin-2-yl)ethyl]benzoxazole mp: 227°–228° C.

IR (Nujol): 1695, 1645, 1625, 1580 cm$^{-1}$

NMR (DCl-$D_2O$, δ): 1.32 (3H, t, J=7 Hz), 2.26 (3H, s), 2.86 (2H, q, J=7 Hz), 3.12 (4H, s), 7.13 (1H, dd, J=2 Hz, 8 Hz), 7.15–7.39 (2H, m), 7.34 (1H, s), 7.56 (1H, s), 8.22 (1H, d, J=7 Hz)

(5) 2-Amino-6-[2-(8-methoxy-3-methylimidazo[1,2-a]pyridin-2-yl)ethyl]benzoxazole mp: 195°–197° C.

IR (Nujol): 1663, 1575, 1550 cm$^{-1}$

NMR (DMSO-$d_6$, δ): 2.23 (3H, s), 2.96 (4H, s), 3.94 (3H, s), 6.49–6.96 (2H, m), 6.91 (1H, dd, J=2 Hz, 8 Hz), 7.08 (1H, d, J=8 Hz), 7.07–7.31 (3H, m), 7.71 (1H, d, J=7 Hz)

(6) 2-Amino-6-[2-(7-hydroxy-3-methylimidazo[1,2-a]pyridin-2-yl)ethyl]benzoxazole mp: 230°–232° C. (dec.)

IR (Nujol): 1660, 1570 cm$^{-1}$

NMR (DMSO-$d_6$, δ): 2.16 (3H, s), 2.89 (4H, m), 6.48 (1H, dd, J=2 Hz, 7 Hz), 6.57 (1H, s), 6.90 (1H, d, J=8 Hz), 6.90–7.33 (4H, m), 7.92 (1H, d, J=7 Hz)

(7) 2-Amino-6-[2-(8-hydroxy-3-methylimidazo[1,2-a]pyridin-2-yl)ethyl]benzoxazole mp: 232°–233° C.

IR (Nujol): 3170, 1665, 1540 cm$^{-1}$

NMR (DCl-$D_2O$, δ): 2.22 (3H, s), 2.83 (4H, s), 7.05–7.44 (5H, m), 7.88 (1H, dd, J=2 Hz, 5 Hz)

(8) 2-Amino-6-[2-(3-formyl-7-methylimidazo[1,2-a]pyridin-2-yl)ethyl]benzoxazole mp: 260°–261° C.

IR (Nujol): 3160 (broad), 1645 cm$^{-1}$

NMR (DMSO-$d_6$, δ): 2.43 (3H, s), 2.96–3.40 (4H, m), 6.91 (1H, dd, J=1.5 Hz, 8 Hz), 7.05 (1H, d, J=8 Hz), 7.06 (1H, dd, J=2 Hz, 8 Hz), 7.20 (3H, s), 7.56 (1H, d, J=2 Hz), 9.22 (1H, d, J=7 Hz) and 9.76 (1H, s)

(9) 2-Amino-5-[2-[7-methoxy-3-methylimidazo[1,2-a]pyridin-2-yl)ethyl]-1H-benzimidazole mp: 230°–233° C.

IR (Nujol): 3290, 3120, 1640, 1565 cm$^{-1}$

NMR (DMSO-$d_6$, δ): 2.20 (3H, s), 2.93 (4H, s), 3.83 (3H, s), 6.60 (1H, dd, J=2 Hz, 7 Hz), 6.70–7.24 (4H, m), 8.01 (1H, d, J=7 Hz)

(10) 2-Amino-5-[2-(3,7-dimethylimidazo[1,2-a]pyridin-2-yl)ethyl]-1-methyl-1H-benzimidazole mp: 240°–242° C.

IR (Nujol): 1670, 1643, 1550 cm$^{-1}$

NMR (DMSO-$d_6$, δ): 2.21 (3H, s), 2.33 (3H, s), 2.93 (4H, s), 3.46 (3H, s), 6.35 (2H, br s), 6.53–6.80 (2H, m), 6.82–7.04 (2H, m), 7.20 (1H, s), 7.95 (1H, d, J=7 Hz)

(11) 2-Amino-6-[2-(3-methyl-5,6,7,8-tetrahydroimidazo[1,2-a]pyridin-2-yl)benzoxazole mp: 233°–234° C.

IR (Nujol): 1675, 1620, 1570 cm$^{-1}$

NMR (DCl-$D_2O$, δ): 1.76–2.23 (4H, m), 1.89 (3H, s), 2.80–3.16 (2H, m), 3.00 (4H, s), 3.73–4.10 (2H, m), 7.13 (1H, dd, J=2 Hz, 8 Hz), 7.32 (1H, d, J=2 Hz), 7.36 (1H, d, J=8 Hz)

(12) 2-Amino-6-[2-(3,7-dimethylimidazo[1,2-a]pyrimidin-2-yl)ethyl]benzoxazole mp: 276°–278° C.

IR (Nujol): 1684, 1625, 1570 cm$^{-1}$

NMR (DCl-$D_2O$, δ): 2.26 (3H, s), 2.80 (3H, s), 3.19 (4H, s), 7.16 (1H, d, J=8 Hz), 7.31 (1H, d, J=8 Hz), 7.37 (1H, s), 7.53 (1H, d, J=7 Hz), 7.71 (1H, d, J=7 Hz)

(13) 6-[2-(6-Acetamidopyridin-2-yl)ethyl]-2-aminobenzoxazole mp: 203° to 204° C.

IR (Nujol): 3250, 3190, 3100, 3055, 1675 cm$^{-1}$

NMR (DMSO-$d_6$, δ): 2.13 (3H, s), 2.88–3.22 (4H, m), 6.90–7.27 (5H, m), 6.96 (1H, dd, J=1 Hz, 7 Hz), 7.65 (1H, t, J=7 Hz), 7.95 (1H, dd, J=1 Hz and 7 Hz) and 10.40 (1H, s)

EXAMPLE 74

2-Amino-5-[2-(2-pyridyl)ethyl]-1H-benzimidazole was obtained according to a similar manner to that of Example 48.

IR (Nujol): 3450, 1700, 1635, 1560 cm$^{-1}$

NMR ($D_2O$+$DCl_3$, δ): 3.13–3.61 (4H, m), 6.93–7.43 (3H, m), 7.83–8.20 (2H, m), 8.40–8.87 (2H, m)

EXAMPLE 75

The following compounds were obtained according to a similar manner to that of Example 12.

(1) 6-[2-(4-Pyridyl)ethyl]-2-aminobenzothiazole mp: 187°–189° C.

IR (Nujol): 3270, 1700, 1635, 1590, 1525 cm$^{-1}$

NMR (DMSO-$d_6$, δ): 2.94 (4H, s), 6.90–7.57 (7H, m), 8.35–8.53 (2H, m)

(2) 6-[2-(3-Pyridyl)ethyl]-2-aminobenzothiazole mp: 210°–212° C.

IR (Nujol): 1710, 1650, 1600, 1565, 1540 cm$^{-1}$

NMR (DMSO-$d_6$, δ): 2.94 (4H, s), 6.98–7.73 (7H, m), 8.33–8.53 (2H, m)

(3) 6-[2-(6-Acetamidopyridin-2-yl)ethyl]-2-aminobenzothiazole

NMR (DMSO-$d_6$, δ): 2.13 (3H, s), 3.00 (4H, br s), 6.77–8.04 (6H, m), 10.40 (1H, s)

(4) 2-Amino-6-[2-(7-methoxy-3-methylimidazo[1,2-a]-pyridin-2-yl)ethyl]benzothiazole mp: 223°–225° C.

IR (Nujol): 1648, 1635, 1535 cm$^{-1}$

NMR (DMSO-$d_6$, δ): 2.22 (3H, s), 2.93 (4H, s), 3.82 (3H, s), 6.56 (1H, dd, J=2 Hz, 7 Hz), 6.82–7.25 (2H, m), 6.87 (1H, d, J=2 Hz), 7.25–7.56 (3H, m), 7.99 (1H, d, J=7 Hz)

(5) 2-Amino-6-[2-(5-dimethylaminomethylfuran-2-yl)ethyl]benzothiazole mp: 153°–154° C.

IR (Nujol): 1665, 1610 cm$^{-1}$

NMR (DMSO-d$_6$, δ): 2.15 (6H, s), 2.89 (4H, s), 3.35 (2H, s), 5.97 (1H, d, J=3 Hz), 6.12 (1H, d, J=3 Hz), 7.04 (1H, dd, J=2 Hz, 8 Hz), 7.25 (1H, d, J=8 Hz), 7.34 (2H, s), and 7.47 (1H, d, J=2 Hz)

(6) 2-Amino-6-[2-(7-methyl-5,6,7,8-tetrahydroimidazo[1,2-a]pyridin-2-yl)ethyl]benzothiazole mp: 232°–235° C.

IR (Nujol): 1660, 1605 cm$^{-1}$

NMR (D$_2$O-DCl, δ): 1.20 (3H, d, J=6 Hz), 1.38–2.33 (3H, m), 2.36–2.74 (1H, m), 2.82–3.33 (1H, m), 2.95 (4H, s), 3.83–4.37 (2H, m), 7.03 (1H, s), 7.26 (2H, s), 7.49 (1H, s)

EXAMPLE 76

5-[2-(2-Furyl)ethyl]-2-methoxycarbonylamino-1H-benzimidazole was obtained according to a similar manner to that of Example 46.

IR (Nujol): 3340, 1715, 1630 cm$^{-1}$

NMR (DMSO-d$_6$, δ): 2.95 (4H, s), 3.78 (3H, s), 6.09 (1H, d, J=3 Hz), 6.35 (1H, dd, J=2 Hz, 3 Hz), 6.97 (1H, dd, J=2 Hz and 8 Hz), 7.28 (1H, d, J=2 Hz), 7.35 (1H, d, J=8 Hz), and 7.52 (1H, d, J=3 Hz)

EXAMPLE 77

A mixture of 2-[2-(4-acetamido-3-hydroxyphenyl)-ethyl]-3,7-dimethylimidazo[1,2-a]pyridine (2.5 g) and phosphorus oxychloride (1.4 ml) in sulfolane (25 ml) was stirred for 1 hour at 100° C. The reaction mixture was added to a mixture of water and ethyl acetate and the separated aqueous layer was adjusted to pH 8 with potassium carbonate. The mixture was extracted with a mixture of ethyl acetate and tetrahydrofuran. The extract was washed with brine and dried over magnesium sulfate. Evaporation of a solvent gave a residue, which was purified by a column chromatography on silica gel eluting with a mixture of chloroform and methanol (39:1, V/V). The eluted fractions containing the desired product were collected and evaporated in vacuo. The residue was crystallized from a mixture of ethyl acetate and diethyl ether to give 6-[2-(3,7-dimethylimidazo[1,2-a]pyridin-2-yl)ethyl]-2-methylbenzoxazole (0.67 g).

mp: 83°–85° C.

IR (Nujol): 1645, 1615, 1575 cm$^{-1}$

NMR (DMSO-d$_6$, δ): 2.21 (3H, s), 2.33 (3H, s), 2.57 (3H, s), 3.03 (4H, s), 6.66 (1H, d, J=7 Hz), 7.12 (1H, d, J=8 Hz), 7.21 (1H, s), 7.43 (1H, s), 7.47 (1H, d, J=8 Hz), 7.97 (1H, d, J=7 Hz)

EXAMPLE 78

The following compounds were obtained according to a similar manner to that of Example 77.

(1) 6-[2-(3,7-Dimethylimidazo[1,2-a]pyridin-2-yl]ethyl]-2-ethylbenzoxazole mp: 115°–117° C.

IR (Nujol): 1645, 1613, 1575 cm$^{-1}$

NMR (DMSO-d$_6$, δ): 1.32 (3H, t, J=7 Hz), 2.22 (3H, s), 2.33 (3H, s), 2.70–3.22 (6H, m), 6.65 (1H, dd, J=2 Hz, 7 Hz), 7.11 (1H, dd, J=2 Hz, 8 Hz), 7.19 (1H, s), 7.43 (1H, s), 7.48 (1H, d, J=8 Hz), 7.95 (1H, d, J=7 Hz)

(2) 5-[2-(3,7-Dimethylimidazo[1,2a]pyridin-2-yl)ethyl]-2-methyl-1H-benzimidazole mp: 151°–153° C.

IR (Nujol): 1645, 1590 cm$^{-1}$

NMR [DCl-D$_2$O, δ]: 2.23 (3H, s), 2.55 (3H, s), 2.92 (3H, s), 3.15 (4H, s), 7.16–7.36 (2H, m), 7.39–7.65 (3H, m), 8.18 (1H, d, J=7 Hz)

EXAMPLE 79

(1) 2-Amino-6-[2-(5-methyl-1-tritylimidazol-4-yl)ethyl]-benzothiazole was obtained according to a similar manner to that of Example 12.

mp: 200°–203° C.

(2) A mixture of 2-amino-6-[2-(5-methyl-1-tritylimidazol-4-yl)ethyl]benzothiazole (1.4 g) in anisole (1.4 ml) and trifluoroacetic acid (6.0 ml) was stirred for 5 hours at ambient temperature. To the reaction mixture was added a diethyl ether, and precipitate was collected by filtration. To the precipitate was added a mixture of tetrahydrofuran, ethyl acetate and water and the mixture was adjusted to pH 9 with potassium carbonate. The separated organic layer was washed with brine and dried over magnesium sulfate. Evaporation of a solvent gave a residue, which was purified by a column chromatography on alumina eluting with a mixture of chloroform and methanol (9:1, V/V). The eluted fractions containing the desired product were collected and evaporated in vacuo to give 2-amino-6-[2-(5-methylimidazol-4-yl)ethyl]benzothiazole (0.24 g).

mp: 191°–193° C.

IR (Nujol): 1635, 1605, 1533 cm$^{-1}$

NMR (D$_2$O-DCl, δ): 1.95 (3H, s), 2.95 (4H, s), 7.16 (1H, d, J=8 Hz), 7.32 (1H, d, J=8 Hz), 7.42 (1H, s), 8.47 (1H, s)

EXAMPLE 80

(1) 2-Amino-5-[2-(5-methyl-1-tritylimidazol-4-yl)ethyl]-1H-benzimidazole was obtained according to a similar manner to that of Example 54.

mp: 161°–164° C.

(2) 2-Amino-5-[2-(5-methylimidazol-4-yl)ethyl]-1H-benzimidazole was obtained according to a similar manner to that of Example 79-(2).

mp: 210°–213° C.

IR (Nujol): 1677, 1643, 1565 cm$^{-1}$

NMR (D$_2$O-DCl, δ): 1.97 (3H, s), 2.91 (4H, m), 6.95 (1H, d, J=8 Hz), 7.01 (1H, s), 7.19 (1H, d, J=8 Hz), 8.49 (1H, s)

EXAMPLE 81

A mixture of potassium ethylxanthogenate (6.25 g) and 2-[2-(4-amino-3-hydroxyphenyl)ethyl]-3,7-dimethylimidazo[1,2-a]pyridine (10.0 g) in ethanol (80 ml) was refluxed for 3 hours with stirring. The resulting precipitate was collected by filtration to give potassium 6-[2-(3,7-dimethylimidazo[1,2-a]pyridin-2-yl)ethyl]-2-benzoxazolethiolate (8.28 g).

mp: >300° C.

IR (Nujol): 1645, 1065 cm$^{-1}$

NMR (DMSO-d$_6$, δ): 2.20 (3H, s), 2.33 (3H, s), 2.95 (4H, s), 6.70 (1H, dd, J=2 Hz, 7 Hz), 6.85 (1H, d, J=2 Hz), 6.88 (1H, d, J=7 Hz), 6.99 (1H, d, J=7 Hz), 7.27 (1H, d, J=2 Hz) and 8.01 (1H, d, J=7 Hz)

EXAMPLE 82

Methyl iodide (0.38 ml) was added dropwise to a solution of potassium 6-[2-(3,7-dimethylimidazo[1,2-a]pyridin-2-yl)ethyl]-2-benzoxazolethiolate (2.00 g) in methanol (30 ml) under ice-water cooling. After being stirred for 3 hours keeping the temperature below 5° C., the solvent was evaporated in vacuo. The residue was mixed with water and extracted with ethyl acetate. The extract was washed with water, dried over magnesium sulfate and evaporated in vacuo. The residue was recrystallized from a mixture of ethyl acetate and n-hexane to give 6-[2-(3,7-dimethylimidazo[1,2-a]pyridin-2-yl)ethyl]-2-methylthiobenzoxazole (1.31 g).

mp: 106°–107° C.

IR (Nujol): 1650, 1600 cm$^{-1}$

NMR (DMSO-d$_6$, δ): 2.22 (3H, s), 2.33 (3H, s), 2.75 (3H, s), 2.95–3.10 (4H, m), 6.67 (1H, dd, J=2 Hz, 7 Hz), 7.15 (1H, dd, J=2 Hz, 7 Hz), 7.23 (1H, d, J=2 Hz), 7.45 (1H, d, J=2 Hz), 7.50 (1H, d, J=8 Hz) and 7.98 (1H, d, J=7 Hz)

EXAMPLE 83

A solution of potassium permanganate (5.25 g) in water (123 ml) was added dropwise to a solution of potassium 6-[2-(3,7-dimethylimidazo[1,2-a]pyridin-2-yl)ethyl]-2-benzoxazolethiolate (6.00 g) in water (80 ml) at 5° C. to 10° C. with stirring. After being stirred for 1 hour at the same temperature, the mixture was concentrated to one half of its original volume. The residue was mixed with water (50 ml) and dichloromethane (50 ml) and the resulting precipitate was collected by filtration to give potassium 6-[2-(3,7-dimethylimidazo[1,2-a]pyridin-2-yl)ethyl]-2-benzoxazolesulfonate (4.45 g).

mp: >300° C.

IR (Nujol): 1635, 1270, 1260, 1250, 1145, 670 cm$^{-1}$

NMR (DMSO-d$_6$, δ): 2.20 (3H, s), 2.35 (3H, s), 3.07 (4H, s), 6.70 (1H, dd, J=2 Hz, 7 Hz), 7.23 (1H, dd, J=2 Hz, 7 Hz), 7.25 (1H, d, J=2 Hz), 7.55 (1H, d, J=2 Hz), 7.64 (1H, d, J=7 Hz) and 7.99 (1H, d, J=7 Hz)

EXAMPLE 84

Potassium 6-[2-(3,7-dimethylimidazo[1,2-a]pyridin-2-yl)ethyl]-2-benzoxazolesulfonate (1.10 g) was added to a mixture of guanidine hydrochloride (257 mg) and potassium hydroxide (150 mg) in N,N-dimethylformamide (12 ml). After being stirred for 4 hours at ambient temperature, the reaction mixture was mixed with water (110 ml) and ethyl acetate (20 ml). The resulting precipitate was collected, washed with water and recrystallized from ethanol to give 6-[2-(3,7-dimethylimidazo[1,2-a]-pyridin-2-yl)ethyl]-2-guanidinobenzoxazole (0.31 g).

mp: 195°–196° C.

IR (Nujol): 3475, 3225, 3125, 1660, 1650, 1605 cm$^{-1}$

NMR (DMSO-d$_6$, δ): 1.08 (3H, t, J=7 Hz), 2.22 (3H, s), 2.35 (4H, s), 3.50 (2H, q, J=7 Hz), 6.70 (1H, dd, J=2 Hz, 7 Hz), 6.93 (1H, dd, J=2 Hz, 8 Hz), 7.18 (6H, br s), 7.20 (1H, d, J=8 Hz) and 8.00 (1H, d, J=7 Hz)

EXAMPLE 85

10% Palladium on carbon (0.2 g) was added to a mixture of 2-amino-6-[2-(3,7-dimethylimidazo[1,2-a]-pyridin-2-yl)ethyl]benzoxazole dihydrochloride (1.0 g) in methanol (70 ml) and the mixture was subjected to catalytic reduction under atmospheric pressure at ambient temperature for 6.5 hours. The catalyst was removed by filtration and the filtrate was evaporated in vacuo. The residue was triturated with ethyl acetate and the precipitate was collected by filtration to give 2-amino-6-[2-(3,7-dimethyl-5,6,7,8-tetrahydroimidazo[1,2-a]pyridin-2-yl)ethyl]benzoxazole dihydrochloride (0.95 g).

mp: 230°–233° C.

IR (Nujol): 3360, 1710, 1640 cm$^{-1}$

NMR (D$_2$O, δ): 1.14 (3H, d, J=6 Hz), 1.53–2.31 (3H, m), 1.87 (3H, s), 2.32–2.70 (1H, m), 2.85–3.22 (1H, m), 2.98 (4H, s), 3.58–4.20 (2H, m), 7.11 (1H, d, J=8 Hz), 7.31 (1H, s), 7.32 (1H, d, J=8 Hz)

EXAMPLE 86

10% Palladium on carbon (0.2 g) was added to a mixture of 2-ethylamino-6-[2-(3-methylimidazo[1,2-a]pyridin-2-yl)ethyl]benzoxazole (0.5 g) in methanol (10 ml) and 1N-hydrochloric acid (10 ml) and the mixture was subjected to catalytic reduction at ambient temperature under atmospheric pressure. The catalyst was removed by filtration and the filtrate was evaporated in vacuo. To the residue was added a mixture of ethyl acetate and water and the mixture was adjusted to pH 8 with 20% aqueous potassium carbonate. The separated organic layer was washed with brine and dried over magnesium sulfate. The solvent was concentration and the residue was triturated with diethyl ether. The precipitate was collected by filtration and dried to give 2-ethylamino-6-[2-(3-methyl-5,6,7,8-tetrahydroimidazo[1,2-a]pyridin-2-yl)-ethyl]benzoxazole (0.41 g).

mp: 139°–141° C.

IR (Nujol): 3140, 1645, 1585 cm$^{-1}$

NMR (DCl-D$_2$O, δ): 1.40 (3H, t, J=8 Hz), 1.78–2.19 (4H, m), 1.91 (3H, s), 2.67–3.09 (2H, m), 2.97 (4H, s), 3.61 (2H, q, J=8 Hz), 3.89 (2H, m), 7.11 (1H, dd, J=2 Hz, 8 Hz), 7.30 (1H, d, J=8 Hz), 7.32 (1H, d, J=2 Hz)

EXAMPLE 87

6-[2-(7-Methyl-5,6,7,8-tetrahydroimidazo[1,2-a]-pyridin-2-yl)ethyl]-2-ethylaminobenzoxazole was obtained according to a similar manner to that of Example 86.

mp: 159°–161° C.

IR (Nujol): 3300, 1650, 1590 cm$^{-1}$

NMR (DMSO-d$_6$, δ): 1.04 (3H, d, J=6 Hz), 1.19 (3H, t, J=7 Hz), 1.37–2.40 (4H, m), 2.43–3.07 (5H, m), 3.13–3.43 (2H, m), 3.52–4.10 (2H, m), 6.62 (1H, s), 6.92 (1H, d, J=2 Hz, 8 Hz), 7.09 (1H, d, J=8 Hz), 7.14 (1H, s), 7.72 (1H, t, J=5 Hz)

EXAMPLE 88

The following compounds were obtained according to a similar manner to that of Example 59.

(1) 5-[2-(5,6,7,8-Tetrahydroimidazo[1,2-a]pyridin-2-yl)-ethyl]-2-ethylaminobenzoxazole mp: 165°–166° C.

IR (Nujol): 3100, 1650, 1590, 1490 cm$^{-1}$

NMR (CDCl$_3$, δ): 1.31 (3H, t, J=7 Hz), 1.7–2.1 (4H, m), 2.6–3.1 (6H, m), 3.50 (2H, q, J=7 Hz), 3.7–4.0 (2H, m), 6.06 (1H, br s), 6.43 (1H, s), 6.83 (1H, dd, J=2 Hz, 9 Hz), 7.08 (1H, d, J=9 Hz), 7.20 (1H, d, J=2 Hz)

(2) 6-[2-(5,6,7,8-Tetrahydroimidazo[1,2-a]pyridin-2-yl)-ethyl]-2-ethylaminobenzoxazole mp: 145°–147° C.

IR (Nujol): 3150, 1645, 1590 cm$^{-1}$

NMR (CDCl$_3$, δ): 1.27 (3H, t, J=7 Hz), 1.66–2.06 (4H, m), 2.63–3.12 (6H, m), 3.27–3.67 (2H, m), 3.67–3.96 (2H, m), 5.72 (1H, br s), 6.40 (1H, s), 6.96 (1H, dd, J=2 Hz, 8 Hz), 7.06 (1H, s), 7.21 (1H, d, J=8 Hz)

EXAMPLE 89

The following compounds were obtained according to a similar manner to that of Example 43.

(1) 5-[2-(3-Bromo-5,6,7,8-tetrahydroimidazo[1,2-a]-pyridin-2-yl)ethyl]-2-ethylaminobenzoxazole mp: 137°–138° C.

IR (Nujol): 3200, 1650, 1570 cm$^{-1}$

NMR (CDCl$_3$, δ): 1.33 (3H, t, J=8 Hz), 1.7–2.2 (4H, m), 2.6–3.2 (6H, m), 3.52 (2H, q, J=8 Hz), 3.6–3.9 (2H, m), 5.5 (1H, br s), 6.86 (1H, dd, J=2 Hz, 9 Hz), 7.13 (1H, d, J=9 Hz), 7.23 (1H, d, J=2 Hz)

(2) 6-[2-(3-Bromo-5,6,7,8-tetrahydroimidazo[1,2-a]-pyridin-2-yl)ethyl]-2-ethylaminobenzoxazole
mp: 162°–164° C.
IR (Nujol): 3150, 1650, 1590 cm$^{-1}$
NMR (DMSO-d$_6$, δ): 1.18 (3H, t, J=7Hz), 1.63–2.05 (4H, m), 2.55–3.04 (6H, m), 3.12–3.50 (2H, m), 3.50–3.84 (2H, m), 6.90 (1H, dd, J=2 Hz, 8 Hz), 7.09 (1H, d, J=8 Hz), 7.14 (1H, s), 7.69 (1H, t, J=5 Hz)

EXAMPLE 90

The following compounds were obtained according to a similar manner to that of Example 66.

(1) 2-Amino -6-[2-(3-chloro-7-methylimidazo[1,2-a]pyridin-2-yl)-ethyl]benzoxazole
mp: 242°–243° C.
IR (Nujol): 1670 cm$^{-1}$
NMR (DMSO-d$_6$, δ): 2.38 (3H, s), 3.01 (4H, s), 6.85 (1H, dd, J=2 Hz, 7 Hz), 6.93–7.13 (3H, m), 7.21 (2H, s), 7.33 (1H, d, J=2 Hz) and 8.09 (1H, d, J=7 Hz)

(2) 2-Acetamido-6-[2-(3-chloro-7-methylimidazo[1,2-a]-pyridin-2-yl)ethyl]benzoxazole
mp: 200°–201° C.
IR (Nujol): 3350 (broad), 1730, 1685, 1650 cm$^{-1}$
NMR (DMSO-d$_6$, δ): 2.25 (3H, s), 2.38 (3H, s), 3.08 (4H, s), 6.88 (1H, dd, J=1.5 Hz, 7 Hz), 7.15 (1H, dd, J=2 Hz, 8 Hz), 7.37–7.47 (2H, m), 7.46 (1H, d, J=8 Hz), 8.12 (1H, d, J=7 Hz) and 11.03 (1H, s)

EXAMPLE 91

6-[2-(3,7-Dimethylimidazo[1,2-a]pyridin-2-yl)ethyl]-2-hydroxybenzoxazole was obtained according to a similar manner to that of Example 67.
mp: 240°–243° C.
IR (Nujol): 3440, 1790, 1763, 1647 cm$^{-1}$
NMR (TFA, δ): 2.40 (3H, s), 2.68 (3H, s), 3.27 (4H, s), 7.08–7.52 (4H, m), 7.66 (1H, s), 8.22 (1H, d, J=7 Hz), 9.74 (1H, br s)

EXAMPLE 92

A mixture of [2-(N-ethylformamido)benzoxazol-6-yl]-methyltriphenylphosphonium bromide (0.5 g), 1-benzyl-2-imidazolecarbaldehyde (0.2 g) and potassium tert-butoxide (0.1 g) in tetrahydrofuran (5.0 ml) was refluxed for 50 minutes. Evaporation of a solvent gave a residue, which was purified by a column chromatography on silica gel eluting with a mixture of chloroform and methanol (19:1, V/V). The eluted fractions containing the desired product were collected and evaporated in vacuo to give 6-[2-(1-benzylimidazol-2-yl)vinyl]-2-ethylaminobenzoxazole (0.2 g).
IR (film): 3200, 1660–1640 (br), 1575 cm$^{-1}$
NMR (DMSO-d$_6$, δ): 1.19 (3H, t, J=7 Hz), 3.07–3.63 (2H, m), 5.24 (2H, s), 6.27 (1H, d, J=13 Hz), 6.66 (1H, d, J=13 Hz), 6.88–7.60 (10H, m), 8.55 (1H, s)

EXAMPLE 93

The following compounds were obtained according to a similar manner to that of Example 92.

(1) 2-Ethylamino-6-[2-(5-methyl-1-tritylimidazol-4-yl)-vinyl]benzoxazole
IR (Nujol): 1640, 1570 cm$^{-1}$ (2) 6-[2-(2-Aminothiazol-4-yl)vinyl]-2-ethylaminobenzoxazole
mp: 203°–205° C.
IR (Nujol): 1670, 1645, 1577 cm$^{-1}$
NMR (DMSO-d$_6$, δ): 1.20 (3H, t, J=7 Hz), 3.05–3.57 (2H, m), 6.50 (1H, s), 6.71–7.33 (6H, m), 7.53 (1H, s), 7.92 (1H, t, J=6 Hz)

(3) 2-Ethylamino-6-[2-[2-furyl)vinyl]benzoxazole
mp: 74°–78° C.
IR (Nujol): 3165, 1670 cm$^{-1}$
NMR (DMSO-d$_6$, δ): 1.20 (3H, t, J=7 Hz), 3.36 (2H, dq, J=5 Hz, 7 Hz), 6.17–6.65 (3H, m), 7.02–7.62 (5H, m), 7.93 (1H, t, J=5 Hz)

EXAMPLE 94

A mixture of 2-ethylamino-6-[2-[5-methyl-1-tritylmethylimidazo-4-yl)vinyl]benzoxazole (1.0 g) in a mixture of formic acid (10 ml) and water (0.3 ml) was stirred for 21 hours at ambient temperature. To the mixture was added a mixture of ethyl acetate, tetrahydrofuran and water and the mixture was adjusted to pH 8 with 20% aqueous potassium carbonate. The separated organic layer was washed with brine and dried over magnesium sulfate. Evaporation of a solvent gave a residue, which was purified by a column chromatography on alumina eluting with a mixture of chloroform and methanol (9:1, V/V). The eluted fractions containing the desired product were collected and evaporated in vacuo to give 2-ethylamino-6-[2-(5-methylimidazol-4-yl)vinyl]benzoxazole (0.44 g).
mp: 197°–199° C.
IR (Nujol): 1657, 1582 cm$^{-1}$
NMR (D$_2$O-DCl, δ): 1.37 (3H, t, J=7 Hz), 2.03 (3H, s), 3.59 (2H, d, J=7 Hz), 6.49 (1H, d, J=12 Hz), 7.01 (1H, d, J=12 Hz), 7.28 (1H, d, J=8 Hz), 7.36 (1H, s), 7.39 (1H, d, J=8 Hz), 8.56 (1H, s)

EXAMPLE 95

10% Palladium on carbon (0.5 g) was added to a mixture of 6-[2-[1-benzylimidazol-2-yl)vinyl]-2-ethylaminobenzoxazole (0.9 g) in a solution of methanol (50 ml) and conc. hydrochloric acid (6 ml), and the mixture was subjected to catalytic reduction under atmospheric pressure for 6 hours at ambient temperature. The catalyst was removed by filtration and the filtrate was evaporated in vacuo. The residue was purified by a column chromatography on alumina and eluted with a chloroform. The eluted fractions containing the desired product were collected and evaporated in vacuo. The residue was triturated with diethyl ether to give 2-ethylamino-6-[2-(2-imidazolyl)ethyl]benzoxazole (0.13 g).
mp: 204°–206° C.
IR (Nujol): 3220, 3160, 1667, 1645, 1590 cm$^{-1}$
NMR (DMSO-d$_6$, δ): 1.17 (3H, t, J=7 Hz), 2.76–3.10 (4H, m), 3.13–3.57 (2H, m), 6.72–6.92 (2H, m), 6.80–6.99 (1H, m), 7.02–7.22 (1H, m), 7.13 (1H, s), 7.33 (1H, t, J=6 Hz), 11.63 (1H, br s)

EXAMPLE 96

The following compounds were obtained according to a similar manner to that of Example 95.

(1) 2-Ethylamino-6-[2-(5-methylimidazol-4-yl)ethyl]-benzoxazole
mp: 198°–201° C.
IR (Nujol): 1680, 1588 cm$^{-1}$
NMR (D$_2$O -DCl, δ): 1.38 (3H, t, J=7 Hz), 1.96 (3H, s), 3.02 (4H, s), 3.60 (2H, q, J=7 Hz), 7.11 (1H, d, J=8 Hz), 7.29 (1H, s), 7.31 (1H, d, J=8 Hz), 8.48 (1H, s)

(2) 2-Ethylamino-6-[2-(2-furyl)ethyl]benzoxazole
mp: 70°–77° C.
IR (Nujol): 3160, 1665 cm$^{-1}$
NMR (DMSO-d$_6$, δ): 1.20 (3H, t, J=7 Hz), 2.93 (4H, s), 3.35 (2H, dq, J=5 Hz, 7 Hz), 6.03–6.53 (2H, m), 6.85–7.53 (4H, m), 7.75 (1H, t, J=5 Hz)

EXAMPLE 97

A solution of sodium hydroxide (464 mg) in water (4.18 ml) was added to a solution of S-(5-dimethylaminomethylfuran-2-yl)methylisothiourea dihydrochloride (1.00 g) in methanol (10 ml) and the mixture was stirred for 1 hour at ambient temperature. A solution of 6-bromomethyl-2-(N-ethylformamido)benzoxazole (1.10 g) in a mixture of methanol (20 ml) and tetrahydrofuran (5 ml) was dropwise added thereto at 0° C. and the mixture was stirred for 2 hours at the same temperature. The solvent was evaporated in vacuo. The residue was mixed with water (20 ml) and extracted with ethyl acetate. The extract was washed with water, dried over magnesium sulfate and evaporated in vacuo. The residue was chromatographed on silica gel by eluting with chloroform-methanol (20:1, V/V). The pure base was converted to the hydrochloride in a usual manner and recrystallized from a mixture of ethanol and diisopropyl ether to give 6-[(5-dimethylaminomethylfuran 2-yl)methylthiomethyl]-2-ethylaminobenzoxazole dihydrochloride (0.33 g).

mp: 181°–183° C.

IR (Nujol): 3080, 1695, 1625 cm$^{-1}$

NMR (DMSO-d$_6$, δ): 1.27 (3H, t, J=7 Hz), 2.72 (6H, s), 3.54 (2H, q, J=7 Hz), 3.72 (2H, s), 3.90 (2H, s), 4.37 (2H, s), 6.38 (1H, d, J=3 Hz), 6.71 (1H, d, J=3 Hz), 7.33 (2H, s), 7.55 (1H, s), 10.27 (2H, br s), 11.33 (1H, br s)

EXAMPLE 98

After a solution of 2-(diaminomethyleneamino)-4-chloromethylthiazole hydrochloride (1.00 g) and thiourea (0.34 g) in ethanol (10 ml) and water (2 ml) was refluxed for 1 hour, 1N-sodium hydroxide solution (13.2 ml) was dropwise added thereto and the mixture was refluxed for further 1 hour. A solution of 6-bromoethyl-2-(N-ethylformamido)benzoxazole (1.25 g) in a mixture of ethanol (10 ml) and tetrahydrofuran (10 ml) was added dropwise at 0° C. and the mixture was stirred for 4 hours at the same temperature. After the solvent was evaporated in vacuo, the residue was mixed with water and extracted with ethyl acetate. The extract was dried over magnesium sulfate and evaporated in vacuo. The residue was treated with chloroform followed by recrystallization from methanol to give 6-[[2-(diaminoethyleneamino)thiazol-4-yl]methylthiomethyl]-2-ethylaminobenzoxazole (0.30 g).

mp: 212°–214° C.

IR (Nujol): 3475, 3380, 3260, 1665 cm$^{-1}$

NMR (DMSO-d$_6$, δ): 1.20 (3H, t, J=7 Hz), 3.35 (2H, dq, J=6 Hz 7 Hz), 3.55 (2H, s), 3.82 (2H, s), 6.48 (1H, s), 6.87 (4H, s), 7.15 (2H, s), 7.30 (1H, s), 7.85 (1H, t, J=6 Hz)

EXAMPLE 99

The following compounds were obtained according to a similar manner to that of Example 97 or 98.

(1) 5-[(5-Dimethylaminomethylfuran-2-yl)methylthiomethyl]-2-ethylaminobenzoxazole monofumarate.

mp: 100°–101° C.

IR (Nujol): 3255, 1710, 1665 cm$^{-1}$

NMR (DMSO-d$_6$, δ): 1.20 (3H, t, J=7 Hz), 2.37 (6H, s), 3.36 (2H, q, J=7 Hz), 3.67 (2H, s), 3.77 (4H, s), 6.26 (1H, d, J=3 Hz), 6.38 (1H, d, J=3 Hz), 6.62 (2H, s), 6.92 (1H, dd, J=2 Hz, 8 Hz), 7.18 (1H, d, J=2 Hz), 7.28 (1H, d, J=8 Hz), 7.83 (1H, br s), 11.58 (2H, br s)

(2) 5-[[2-(Diaminomethyleneamino)thiazole-4-yl]methylthiomethyl]-2-ethylaminobenzoxazole mp: 168° to 169° C.

IR (Nujol): 3490, 3390, 3270, 1670 cm$^{-1}$

NMR (DMSO-d$_6$, δ): 1.19 (3H, t, J=7 Hz), 3.18–3.39 (2H, m), 3.50 (2H, s), 3.75 (2H, s), 6.43 (1H, s), 6.82 (4H, s), 6.88 (1H, dd, J=2 Hz, 8 Hz), 7.13 (1H, d, J=2 Hz), 7.20 (1H, d, J=8 Hz), 7.79 (1H, t, J=5 Hz)

EXAMPLE 100

Methanolic sodium methoxide (28 wt. %, 1.25 g) was added to a solution of 2-acetamido-6-hydroxybenzoxazole (1.25 g) and 2-chloromethyl-7-methylimidazo[1,2-a]pyridine (1.41 g) in N,N-dimethylformamide (25 ml). After the mixture was stirred at 50° C. for 17 hours, the solvent was evaporated in vacuo. Water was added to the residue and the mixture was extracted with ethyl acetate. The extract was washed with water, dried over magnesium sulfate and evaporated in vacuo. The residue was chromatographed on silica gel (62.5 g) by eluting with chloroform-methanol (50:1, V/V), and the product obtained was recrystallized from a mixture of methanol, dioxane and diisopropyl ether to give 2-acetamido-6-[(7-methylimidazo[1,2-a]pyridin-2-yl)methoxy]benzoxazole (0.22 g).

mp: 214°–215° C.

IR (Nujol): 3140, 3075, 1675, 1620 cm$^{-1}$

NMR (DMSO-d$_6$, δ): 2.29 (3H, s), 2.46 (3H, s), 3.33 (4H, s), 5.17 (2H, s), 6.66 (1H, dd, J=1.5 Hz, 7 Hz), 6.78 (1H, dd, J=2 Hz, 8 Hz), 6.99 (1H, d, J=2 Hz), 7.20 (1H, d, J=1.5 Hz), 7.43 (1H, d, J=8 Hz), 7.70 (1H, s), 8.32 (1H, d, J=7 Hz), 9.68 (1H, br s)

EXAMPLE 101

A mixture of 7-methylimidazo[1,2-a]pyridin-2-ylmethanethiol (1.5 g) and 5-bromomethyl-2-(N-ethylformamido)benzoxazole (2.9 g) in a solution of acetone (40 ml) and water (30 ml) was adjusted to pH 9–10 with saturated aqueous potassium carbonate solution under ice-cooling. The mixture was stirred for 2 hours at the same temperature and the isolated precipitate was collected by filtration to give 2-(N-ethylformamido)-5-(7-methylimidazo[1,2-a]pyridin-2-yl)methylthiomethyl]benzoxazole (1.53 g).

mp: 110°–112° C.

IR (Nujol): 1690, 1650, 1620, 1570 cm$^{-1}$

DMSO-d$_6$, δ): 1.23 (3H, t, J=7 Hz), 2.33 (3H, s), 3.69 (2H, s), 3.89 (2H, s), 3.91 (2H, q, J=7 Hz), 6.67 (1H, d, J=7 Hz), 7.23 (1H, s), 7.27 (1H, d, J=8 Hz), 7.56 (1H, d, J=8 Hz), 7.57 (1H, s), 7.72 (1H, s), 8.32 (1H, d, J=7 Hz), 9.21 (1H, s)

EXAMPLE 102

The following compounds were obtained according to a similar manner to that of Example 101.

(1) 2-N-Ethylformamido)-6-[(7-methylimidazo[1,2-a]pyridin-2-yl)methylthiomthyl]benzoxazole mp: 98°–104° C.

NMR (DMSO-d$_6$, δ): 1.23 (3H, t, J=7 Hz), 2.31 (3H, s), 3.70 (2H, s), 3.90 (2H, s), 3.92 (2H, q, J=7 Hz), 6.66 (1H, dd, J=2 Hz, 7 Hz), 7.23 (1H, s), 7.31 (1H, dd, J=2 Hz, 8 Hz), 7.52 (1H, d, J=8 Hz), 7.59 (1H, s), 7.69 (1H, s), 8.30 (1H, d, J=7 Hz), 9.18 (1H, s)

(2) 2-(N-Ethylformamido)-4-[(7-methylimidazo[1,2-a]-pyridin-2-yl)methylthiomethyl]benzoxazole mp: 127°–131° C.

IR (Nujol): 1695, 1625, 1610, 1570 cm$^{-1}$

NMR (DMSO-d$_6$, δ): 1.23 (3H, t, J=7 Hz), 2.34 (3H, s), 3.80 (2H, s), 3.94 (2H, q, J=7 Hz), 4.06 (2H, s), 6.69

(1H, dd, J=2 Hz, 7 Hz), 7.20-7.49 (3H, m), 7.30-7.63 (1H, m), 7.76 (1H, s), 8.34 (1H, d, J=7 Hz), 9.21 (1H, s)

EXAMPLE 103

A mixture of 2-acetamido-3-hydroxypyridine (1.3 g), 2-amino-6-chloromethylbenzoxazolehydrochloride (1.5 g) and potassium carbonate (2.8 g) in N,N-dimethylformamide (20 ml) was stirred for 4.3 hours at 40° C. The reaction mixture was added to water and the mixture was extracted with a mixture of ethyl acetate and tetrahydrofuran. The extract was washed with brine and dried over magnesium sulfate. The solvent was evaporated and the residue was crystallized from ethyl acetate to give 6-(2-acetamido-pyridin-3-yloxymethyl}-2-aminobenzoxazole (0.83 g).

mp: 194°-196° C.

IR (Nujol): 3390, 3230, 1680, 1660, 1620, 1570 cm$^{-1}$

NMR (DMSO-d$_6$, δ): 2.08 (3H, s), 5.20 (2H, s), 7.05-7.33 (1H, m), 7.22-7.65 (4H, m), 7.24 (2H, m), 7.96 (1H, dd, J=2 Hz, 5 Hz), 9.58 (1H, s)

EXAMPLE 104

The following compounds were obtained according to a similar manner to that of Example 103.

(1) 2-(N-Ethylformamido)-6-(3-formylphenoxymethyl)benzoxazole mp: 87°-89° C.

IR (Nujol): 1695, 1680, 1625 cm$^{-1}$

NMR (DMSO-d$_6$, δ): 1.23 (3H, t, J=7 Hz), 3.95 (2H, q, J=7 Hz), 5.30 (2H, s), 7.27-7.77 (7H, m), 9.23 (1H, s), 10.00 (1H, s)

(2) 2-(N-ethylformamido)-5-(3-formylphenoxymethyl)benzoxazole mp: 112°-114° C.

IR (Nujol): 1710, 1690, 1635 cm$^{-1}$

NMR (DMSO-d$_6$, δ): 1.23 (3H, t, J=7 Hz), 3.94 (2H, q, J=7 Hz), 5.30 (2H, s), 7.29-7.73 (7H, m), 9.28 (1H, s), 10.04 (1H, s)

EXAMPLE 105

A mixture of 2-(N-ethylformamido)-6-[(7-methylimidazo[1,2-a]pyridin-2-yl)methylthiomethyl]-benzoxazole (0.6 g) in methanol (12 ml) and conc. hydrochloric acid (0.7 ml) was stirred at ambient temperature and the mixture was concentrated. To the residue was added a mixture of ethyl acetate, tetrahydrofuran and water, and the mixture was adjusted to pH 8 with potassium carbonate. The separated organic layer was washed with brine and dried over magnesium sulfate. Evaporation of a solvent gave a residue, which was purified by a column chromatography on silica gel eluting with chloroform. The eluted fractions containing the desired product were collected and evaporated in vacuo. The residue was triturated with diethyl ether to give 2-ethylamino-6-[(7-methylimiazo[1,2-a]pyridin-2-yl)methylthiomethyl]benzoxazole (0.42 g).

mp: 142°-144° C.

IR (Nujol): 1665, 1640, 1590 cm$^{-1}$

NMR (DMSO-d$_6$, δ): 1.20 (3H, t, J=7 Hz), 2.33 (3H; s), 3.13-3.51 (2H, m), 3.69 (2H, s), 3.82 (2H, s), 6.66 (1H, dd, J=2 Hz, 7 Hz), 6.98-7.14 (2H, m), 7.14-7.38 (2H, m), 7.69 (1H, s), 7.80 (1H, t, J=5 Hz), 8.29 (1H, d, J=7 Hz)

EXAMPLE 106

The following compounds were obtained according to a similar manner to that of Example 105.

(1) 2-Ethylamino-4-[(7-methylimidazo[1,2-a]pyridin-2-yl]methylthiomethyl]benzoxazole mp: 170°-172° C.

IR (Nujol): 1655 1620 1590 cm$^{-1}$

NMR (DMSO-d$_6$, δ): 1.22 (3H, t, J=7 Hz), 2.33 (3H, s), 3.19-3.62 (2H, m), 3.84 (2H, s), 3.99 (2H, s), 6.66 (1H, d, J=7 Hz), 6.96 (1H, d, J=8 Hz), 7.06-7.33 (3H, m), 7.83 (1H, s), 7.94 (1H, t, J=5 Hz), 8.32 (1H, d, J=7 Hz)

(2) 2-Ethylamino-5-[(7-methylimidazo[1,2-a]pyridin-2-yl)methylthiomethyl]benzoxazole mp: 134°-136° C.

IR (Nujol): 1667, 1580 cm$^{-1}$

NMR (DMSO-d$_6$, δ): 1.20 (3H, t, J=7 Hz), 2.33 (3H, s), 3.12-3.53 (2H, m), 3.69 (2H, s), 3.81 (2H, s), 6.66 (1H, d, J=7 Hz), 6.92 (1H, d, J=8 Hz), 7.51 (3H, s), 7.70 (1H, s), 7.82 (1H, t, J=5 Hz), 8.30 (1H, d, J=7 Hz)

EXAMPLE 107

(1) 2-Ethylamino-5-(3-formylphenoxymethyl)benzoxazole was obtained according to a similar manner to that of Example 105.

mp: 85°-90° C.

IR (Nujol): 1770, 1690, 1650 cm$^{-1}$

NMR (DMSO-d$_6$, δ): 1.20 (3H, t, J=7 Hz), 3.38 (2H, dt, J=5 Hz, 7 Hz), 5.22 (2H, s), 7.03-7.57 (7H, m), 8.03 (1H, t, J=5 Hz), 10.00 (1H, s)

(2) Sodium cyanoborohydride (0.17 g) was added portionwise to a solution of 2-ethylamino-5-(3-formylphenoxymethyl)benzoxazole (0.80 g), piperidine (0.23 g) and acetic acid (0.76 ml) in methanol (10 ml) at 0° C. with stirring. The mixture was stirred at the same temperature for 2 hours and for further 6 hours at ambient temperature. The solvent was evaporated in vacuo. The residue was mixed with a saturated sodium bicarbonate solution and extracted with ethyl acetate. The extract was washed with water, dried over magnesium sulfate and evaporated in vacuo. The residue was chromatographed on silica gel by eluting with a mixture of chloroform-methanol (20:1, V/V). The pure base was converted to the hydrochloride in a usual manner. The salt was dissolved in ethanol and reprecipitated with diethyl ether to give 2-ethylamino-5-3-piperidinomethylphenoxymethyl)benzoxazole (0.35 g) dihydrochloride.

mp: 132° to 133° C.

IR (Nujol): 3375, 1725, 1620 cm$^{-1}$

NMR (DMSO-d$_6$, δ): 1.24 (3H, t, J=8 Hz), 1.50-2.10 (6H, m), 2.63-3.30 (4H, m), 3.47 (2H, q, J=8 Hz), 4.20 (2H, d, J=4.5 Hz), 5.22 (2H, s), 7.03-7.56 (7H, m), 9.80 (1H, br s), 11.10 (1H, br s)

EXAMPLE 108

2-Ethylamino-6-(3-piperidinomethylphenoxymethyl)benzoxazole was obtained according to a similar manner to that of Example 107.

mp: 105°-106° C.

IR (Nujol): 1690 cm$^{-1}$

NMR (DMSO-d$_6$, δ): 1.18 (3H, t, J=6.5 Hz), 1.35-1.58 (6H, m), 2.17-2.42 (4H, m), 3.33 (2H, dq, J=5 Hz, 6.5 Hz), 3.37 (2H, s), 5.07 (2H, s), 6.73-7.13 (4H, m), 7.20 (2H, s), 7.40 (1H, s), 7.88 (1H, t, J=5 Hz)

EXAMPLE 109

A mixture of acetic anhydride (1.13 ml) and formic acid (0.45 ml) was stirred at 50° C. for 40 minutes. Tetrahydrofuran (10 ml) and 2-ethylamino-6-[2-(2-furyl)ethyl]benzoxazole (1.02 g) was added thereto and the mixture was stirred at the same temperature for further 6 hours. After cooling, the mixture was neutralized with aqueous sodium bicarbonate and extracted with ethyl acetate. The extract was washed with water dried over magnesium sulfate and evaporated in vacuo to give 2-(N-ethylformamido)-6-[2-(2-furyl)ethyl]benzoxazole (1.18 g).

mp: 54°–58° C.

IR (Nujol): 1700, 1640 cm$^{-1}$

NMR (DMSO-d$_6$, δ): 1.20 (3H, t, J=7 Hz), 2.93 (4H, s), 3.37 (2H, q, J=7 Hz), 6.08 (1H, d, J=3 Hz), 6.35 (1H, dd, J=2 Hz, 3 Hz), 7.00–7.60 (4H, m), 8.15 (1H, s)

EXAMPLE 110

A mixture of 2-(N-ethylformamido)-6-[2-(2-furyl)ethyl]benzoxazole (1.25 g), 36% formalin (1.83 ml) and dimethylamine hydrochloride (1.79 g) in acetic acid (8.3 ml) was stirred at 80° C. for 6 hours. The solvent was evaporated in vacuo, the residue was mixed with saturated aqueous sodium bicarbonate and extracted with ethyl acetate. The extract was washed with water, dried over magnesium sulfate and evaporated in vacuo. The residue was chromatographed on silica gel by eluting with chloroform-methanol (20:1, V/V). The pure base was converted to the maleate in a usual way and the salt was recrystallized from ethyl acetate to give 6-[2-(5-dimethylaminomethylfuran-2-yl)ethyl]-2-ethylaminobenzoxazole 3/2 maleate (0.38 g).

mp: 72° to 73° C.

IR (Nujol): 1710, 1670 cm$^{-1}$

NMR (DMSO-d$_6$, δ): 1.19 (3H, t, J=7 Hz), 2.71 (6H, s), 2.95 (4H, s), 3.20–3.43 (2H, m), 4.29 (2H, s), 6.07 (3H, s), 6.13 (1H, d, J=3 Hz), 6.53 (1H, d, J=3 Hz), 6.90 (1H, dd, J=2 Hz, 8 Hz), 7.09 (1H, d, J=8 Hz), 7.17 (1H, d, J=2 Hz), 7.70 (1H, br s)

EXAMPLE 111

The following compounds were obtained according to a similar manner to that of Example 110.

(1) 5-[2-(5-Dimethylaminomethylfuran-2-yl)ethyl]-2-methoxycarbonylamino-1H-benzimidazole mp: 194°–195° C.

IR (Nujol): 3300, 1705, 1620 cm$^{-1}$

NMR (DMSO-d$_6$, δ): 2.13 (6H, s), 2.91 (4H, s), 3.34 (2H, s), 3.74 (3H, s), 5.96 (1H, d, J=3 Hz), 6.09 (1H, d, J=3 Hz), 6.92 (1H, dd, J=2 Hz, 8 Hz), 7.22 (1H, d, J=2 Hz), 7.28 (1H, d, J=8 Hz), 11.55 (2H, br s)

(2) 2-Acetamido-6-[2-(3-dimethylaminomethyl-7-methylimidazo[1,2-a]pyridin-2-yl)ethyl]benzoxazole mp: 184°–185° C.

IR (Nujol): 1715, 1620 cm$^{-1}$

NMR (DMSO-d$_6$, δ): 2.01 (6H, s), 2.20 (3H, s), 2.34 (3H, s), 2.85–3.11 (4H, m), 3.53 (2H, s), 6.71 (1H, dd, J=2 Hz, 7 Hz), 7.08–7.44 (4H, m), 8.14 (1H, d, J=7 Hz)

EXAMPLE 112

A mixture of 2-ethylamino-6-[2-(2-furyl)ethyl]benzoxazole (0.93 g), 37% formalin (0.30 ml), concentrated hydrochloric acid (0.35 ml) and piperidine (0.34 g) in acetic acid (10 ml) was stirred at 70° C. for 2 hours. After the solvent was evaporated in vacuo, saturated aqueous sodium bicarbonate was added to the residue and the mixture was extracted with ethyl acetate. The extract was washed with water, dried over magnesium sulfate and evaporated in vacuo. The residue was chromatographed on silica gel by eluting with ethyl acetate-toluene (2:8, V/V). The free base was converted to the maleate in a usual way and recrystallized from a mixture of ethanol and diethyl ether to give 2-ethylamino-6-[2-(5-piperidinomethylfuran-2-yl)ethyl]benzoxazole 5/4 maleate (0.45 g).

mp: 98°–100° C.

IR (Nujol): 1710, 1670, 1620 cm$^{-1}$

NMR (DMSO-d$_6$, δ): 1.17 (3H, t, J=7 Hz), 1.36–1.83 (6H, m), 2.96 (4H, s), 2.96–3.15 (4H, m), 3.15–3.45 (2H, m), 4.26 (2H, s), 6.07 (2H, s), 6.15 (1H, d, J=3 Hz), 6.53 (1H, d, J=3 Hz), 6.93 (1H, dd, J=2 Hz, 8 Hz), 7.12 (1H, d, J=8 Hz), 7.15 (1H, d, J=2 Hz), 7.73 (1H, t, J=5 Hz)

EXAMPLE 113

Sodium borohydride (156 mg) was added in portions to a solution of 2-amino-6-[2-(3-formyl-7-methylimidazo[1,2-a]pyridin-2-yl)ethylbenzoxazole (0.65 g) in methanol (20 ml) under ice cooling. After stirring for 23 hours at ambient temperature, the solvent was evaporated in vacuo. The residue was mixed with water and the mixture was neutralized with 1N-hydrochloric acid. The resulting precipitate was collected, washed with water and recrystallized from a mixture of methanol, dioxane and diisopropyl ether to give 2-amino-6-[2-(3-hydroxymethyl-7-methylimidazo[1,2-a]pyridin-2-yl)ethyl]benzoxazole (0.17 g).

mp: >200° C. (dec.)

IR (Nujol): 3340, 3280, 3125, 1680, 1650 cm$^{-1}$

NMR (DMSO-d$_6$, δ): 2.35 (3H, s), 2.96 (4H, s), 4.61 (2H, d, J=4 Hz), 4.96 (1H, t, J=4 Hz), 6.72 (1H, dd, J=2 Hz, 7 Hz), 6.91 (1H, dd, J=1.5 Hz, 8 Hz), 7.07 (1H, d, J=8 Hz), 7.16 (1H, d, J=1.5 Hz), 7.21 (2H, s), 7.24 (1H, d, J=2 Hz), 8.18 (1H, d, J=7 Hz)

EXAMPLE 114

The following compounds were obtained according to a similar manner to that of Example 57.

(1) 2-Acetamido-6-[2-(7-acetoxy-3-methylimidazo[1,2-a]pyridin-2-yl)ethyl]benzoxazole mp: 161°–164° C.

IR (Nujol): 1770, 1695, 1625, 1575 cm$^{-1}$

NMR (DMSO-d$_6$, δ): 2.22 (3H, s), 2.25 (3H, s), 2.30 (3H, s), 3.02 (4H, s), 6.75 (1H, dd, J=2 Hz, 7 Hz), 7.10 (1H, d, J=8 Hz), 7.23 (1H, d, J=2 Hz), 7.41 (1H, d, J=8 Hz), 7.42 (1H, s), 8.13 (1H, d, J=7 Hz)

(2) 2-Acetamido-6-[2-(7-methylimidazo[1,2-a]pyridin-2-yl)ethyl]benzothiazole mp: 259°–260° C.

IR (Nujol): 1690, 1650 cm$^{-1}$

NMR (DMSO-d$_6$,δ): 2.20 (3H, s), 2.32 (3H, s), 3.05 (4H, s), 6.62 (1H, dd, J=1.5 Hz, 7 Hz), 7.21 (1H, d, J=2 Hz), 7.26 (1H, dd, J=2 Hz, 8 Hz), 7.52 (1H, d, J=1.5 Hz), 7.60 (1H, d, J=8 Hz), 7.77 (1H, s), 8.26 (1H, d, J=7 Hz), 12.30 (1H, br s)

(3) 2-Acetamido-5-[2-(7-methoxy-3-methylimidazo[1,2-a]pyridin-2-yl)ethyl]-1H-benzimidazole mp: 235°–237° C.

IR (Nujol): 3350, 1680, 1640, 1600 cm$^{-1}$

NMR (DMSO-d$_6$, δ): 2.18 (6H, s), 2.97 (4H, s), 3.85 (3H, s), 6.61 (1H, d, J=7 Hz), 6.83–7.12 (1H, m), 6.92 (1H, s), 7.21–7.50 (1H, m), 7.32 (1H, s), 8.04 (1H, d, J=7 Hz)

EXAMPLE 115

Acetyl chloride (1.2 ml) was added to a mixture of 2-amino-6-[2-(7-hydroxy-3-methylimidazo[1,2-a]pyridin-2-yl)ethyl]benzoxazole (1.8 g) and triethylamine (2.4 ml) in dichloromethane (36 ml) under ice-cooling and a mixture was stirred for 15 hours at ambient temperature. To the reaction mixture was added a mixture of ethyl acetate and tetrahydrofuran, and the resulting mixture was washed with water. The mixture was dried over magnesium sulfate and evaporated to give 2- amino-6-[2-(7-acetoxy-3-methylimidazo[1,2-a]pyridin-2-yl)ethyl]benzoxazole (0.27 g).

mp: 194°–195° C.

IR (Nujol): 3240, 1755, 1680, 1575 cm$^{-1}$

NMR (DMSO-d$_6$, δ): 2.26 (3H, s), 2.32 (3H, s), 2.98 (4H, s), 6.80 (1H, dd, J=2 Hz, 7 Hz), 6.95–7.43 (4H, m), 7.27 (2H, s), 8.19 (1H, d, J=7 Hz)

EXAMPLE 116

2-Acetamido-6-[2-(7-acetoxy-3-methylimidazo[1,2-a]pyridin-2-yl)ethyl]benzoxazole (0.5 g) was subjected to a column chromatography on silica gel for 15 hours at ambient temperature and then the column was eluted with the mixture of methanol and chloroform (1:9 to 1:3, V/V). The eluted fractions containing the desired product were collected and evaporated in vacuo. To the resulting residue was added a mixture of ethyl acetate, tetrahydrofuran and water, and the mixture was adjusted to pH 7.5 with saturated aqueous sodium bicarbonate. The separated organic layer was washed with a brine, dried over magnesium sulfate and evaporated to give 2-acetamido-6-[2-(7-hydroxy-3-methylimidazo[1,2-a]pyridin-2-yl)ethyl]benzoxazole (0.18 g).

mp: 210°–212° C.

IR (Nujol): 3350 (br), 1725, 1660, 1640, 1580 cm$^{-1}$

NMR (DMSO-d$_6$, δ): 2.23 (6H, s), 3.06 (4H, s), 6.81 (1H, d, J=7 Hz), 6.88 (1H, s), 7.16 (1H, d, J=8 Hz), 7.48 (1H, d, J=8 Hz), 7.51 (1H, s), 8.18 (1H, d, J=7 Hz)

EXAMPLE 117

The following compounds were obtained according to a similar manner to that of Example 70.

(1) 6-[2-(6-Aminopyridin-2-yl)ethyl]-2-aminobenzothiazole mp: 202°–204° C.

IR (Nujol): 3480, 3370, 3250, 1700, 1610, 1590, 1570, 1530, 1510 cm$^{-1}$

NMR (D$_2$O+DCl, δ): 3.00 (4H, br s), 6.77 (1H, d, J=7 Hz), 6.97 (1H, d, J=7 Hz), 7.40 (2H, s), 7.58 (1H, s), 7.73 (1H, dd, J=7.7 Hz)

(2) 2-Amino-6-[2-(6-aminopyridin-2-yl)ethyl]benzoxazole mp: 164°–165° C.

IR (Nujol): 3420, 3290, 1685 cm$^{-1}$

NMR (DMSO-d$_6$, δ): 2.70–3.10 (4H, m), 5.80 (2H, br s), 6.30 (1H, d, J=8 Hz), 6.37 (1H, d, J=8 Hz), 6.95 (1H, dd, J=1 Hz, 7 Hz), 7.07 (1H, s), 7.17–7.42 (4H, m)

(3) 2-Amino-6-(2-aminopyridin-3-yloxymethyl)benzoxazole dihydrochloride mp: 201°–203° C.

IR (Nujol): 3300, 3150, 1710, 1650, 1630, 1560 cm$^{-1}$

NMR (D$_2$O, δ): 5.32 (2H, s), 6.87 (1H, dd, J=each 7 Hz), 7.30–7.62 (4H, m), 7.66 (1H, s)

EXAMPLE 118

2-Acetamido-6-[2-(7-methylimidazo[1,2-a]pyridin-2-yl)ethyl]benzoxazole (2.20 g) was added in small portions to a solution of phosphorous oxychloride (1.79 ml) in N,N-dimethylformamide (20 ml) at ambient temperature with stirring. After being stirred for 1 hour, the mixture was diluted with water (200 ml) and stirred for an additional 30 minutes. The mixture was made alkaline with aqueous potassium carbonate and extracted with dichloromethane. The extract was washed with water, dried over magnesium sulfate, and evaporated in vacuo to give dark brown amorphous powder. The crude material was chromatographed on silica gel by eluting with chloroform-methanol (50:1, V/V), followed by recrystallization from a mixture of methanol and diisopropyl]ether to give 2-dimethylaminomethyleneamino-6-[2-(7-methylimidazo[1,2-a]pyridin-2-yl)ethyl]benzoxazole (0.31 g).

mp: 150°–151° C.

IR (Nujol): 1630 cm$^{-1}$

NMR (DMSO-d$_6$, δ): 2.33 (3H, s), 3.05 (6H, s), 3.18 (3H, s), 3.38 (1H, s), 6.65 (1H, dd, J=2 Hz, 7 Hz), 7.07 (1H, dd, J=1.5 Hz, 9 Hz), 7.23–7.37 (3H, m), 7.57 (1H, s), 8.32 (1H, d, J=7 Hz), 8.62 (1H, s)

Preparation 69

(1) A mixture of 1,3-dichloroacetone (30.0 g) and 2-amino-4-picoline (63.9 g) in acetonitrile (210 ml) was refluxed for 1 hour. Evaporation of a solvent gave a residue, which was purified by a column chromatography on silica gel eluting with a mixture of dichloromethane and ethyl acetate (1:1, V/V). The eluted fractions containing the desired product were collected and evaporated in vacuo to give 2-chloromethyl-7-methylimidazo[1,2-a]pyridine (10.21 g).

mp: 88°–90° C.

NMR (DMSO-d$_6$, δ): 2.34 (3H, s), 4.82 (2H, s), 6.74 (1H, dd, J=2 Hz, 7 Hz), 7.30 (1H, s), 7.90 (1H, s), 8.39 (1H, d, J=7 Hz)

(2) A mixture of 2-chloromethyl-7-methylimidazo[1,2-a]pyridine (5.0 g) and thiourea (2.2 g) in ethanol (10 ml) was refluxed for 20 minutes and the mixture was added to a ethyl acetate (100 ml) under stirring. The isolated precipitate was collected by filtration and washed with ethyl acetate to give S-(7-methylimidazo[1,2-a]pyridin-2-ylmethyl)isothiourea hydrochloride (7.11 g).

mp: 170°–172° C.

IR (Nujol): 1665, 1650 cm$^{-1}$

NMR (D$_2$O, δ): 2.34 (3H, s), 4.54 (2H, s), 6.66 (1H, dd, J=2 Hz, 7 Hz), 7.10 (1H, s), 7.67 (1H, s), 8.02 (1H, d, J=7 Hz)

(3) A mixture of S-(7-methylimidazo[1,2-a]pyridin-2-ylmethyl)isothiourea hydrochloride (7.7 g) and sodium hydroxide (1.2 g) in water (54 ml) was refluxed for 2 hours and the reaction mixture was extracted with ethyl acetate. The extract was washed with water, and dried over magnesium sulfate. The solvent was evaporated in vacuo to give 7-methylimidazo[1,2-a]pyridin-2-ylmethanethiol (4.2 g).

mp: 164°–168° C.

IR (Nujol): 1640 cm$^{-1}$

NMR (DMSO-d$_6$, δ): 2.33 (3H, s), 4.00 (2H, s), 6.72 (1H, dd, J=2 Hz, 7 Hz), 7.28 (1H, s), 7.77 (1H, s), 8.38 (1H, d, J=7 Hz)

Preparation 70

(1) 2-Amino-6-ethoxycarbonylbenzoxazole was obtained according to a similar manner to that of Example 54 or 55.

mp: 211°–212° C.

IR (Nujol): 3380, 1690, 1660, 1630, 1550 cm$^{-1}$

NMR (DMSO-d$_6$, δ): 3.33 (3H, t, J=7 Hz), 4.34 (2H, q, J=7 Hz), 7.30 (1H, d, J=8 Hz), 7.70–8.07 (4H, m)

(2) A solution of 2-amino-6-ethoxycarbonylbenzoxazole (14.3 g) in tetrahydrofuran (570 ml) was dropwise added to a mixture of lithium aluminum hydride (7.9 g) in tetrahydrofuran (300 ml) at −30° C. to −20° C. for 35 minutes, and the mixture was stirred for 75 minutes at the same temperature. To the reaction mixture was dropwise added a mixture of water (3 ml) and tetrahydrofuran (3 ml), and the mixture of ethyl acetate and water was added to a resulting mixture. The mixture was adjusted to pH 7 with 6N-hydrochloric acid and the isolated precipitate was removed by filtration. The separated organic layer from filtrate was washed with brine and dried over magnesium sulfate. Evaporation of a solvent gave a residue, which was purified by a column chromatography on silica gel eluting with a mixture of chloroform and methanol (9:1, V/V). The eluted fractions containing the desired product were collected and evaporated in vacuo to give 2-amino-6-hydroxymethylbenzoxazole (5.77 g).

mp: 148°–150° C.
IR (Nujol): 3410, 3350, 1660, 1570 cm$^{-1}$
NMR (DMSO-$d_6$, δ): 4.54 (2H, d, J=5 Hz), 5.14 (1H, t, J=5 Hz), 6.97–7.23 (2H, m), 7.23–7.54 (3H, m)

(3) The mixture of 2-amino-6-hydroxymethylbenzoxazole (0.5 g) and thionyl chloride (0.66 ml) in dichloromethane (5 ml) was stirred for 4.5 hours under ice-cooling. The isolated precipitate was collected by filtration, washed with diethyl ether and dried to give 2-amino-6-chloromethylbenzoxazole hydrochloride (0.57 g).

mp: 168°–169° C.
IR (Nujol): 1710 cm$^{-1}$
NMR ($D_2O$, δ): 4.74 (2H, s), 7.43 (2H, s), 7.56 (1H, s)

Preparation 71

The mixture of 6-bromomethyl-2-(N-ethylformamido)benzoxazole (0.35 g) and triphenylphosphine (0.32 g) in tetrahydrofuran (5 ml) was refluxed for 1.8 hours and the mixture was cooled to 0°–5° C. The isolated precipitate was collected by filtration to give [2-(N-ethylformamido)benzoxazol-6-yl]methyltriphenylphosphonium bromide (0.51 g).

mp: 244°–248° C.
NMR (DMSO-$d_6$, δ): 1.20 (3H, t, J=7 Hz), 3.91 (2H, q, J=7 Hz), 5.26 (1H, s), 5.51 (1H, s), 6.80–8.13 (18H, m), 9.18 (1H, s)

Preparation 72

The mixture of 2-(N-ethylformamido)-6-methylbenzoxazole (7.6 g), N-bromosuccinimide (6.6 g) and benzoyl peroxide (0.2 g) in benzene (150 ml) was refluxed for 70 minutes and the mixture was cooled to ambient temperature. To the reaction mixture was added ethyl acetate, and the mixture was washed with water and dried over magnesium sulfate. The solvent was evaporated and the residue was triturated in a mixture of diisopropyl ether and n-hexane to give 6-bromomethyl-2-(N-ethylformamido)benzoxazole (6.18 g).

mp: 98°–100° C.
NMR (DMSO-$d_6$, δ): 1.23 (3H, t, J=7 Hz), 3.95 (2H, q, J=7 Hz), 4.86 (2H, s), 7.34–7.63 (2H, m), 7.77 (1H, d, J=2 Hz), 9.24 (1H, s)

Preparation 73

The following compounds were obtained according to a similar manner to that of Preparation 72.

(1) 5-Bromomethyl-2-(N-ethylformamido)benzoxazole
mp: 95°–96° C.
IR (Nujol): 1700, 1630, 1570 cm$^{-1}$
NMR (DMSO-$d_6$, δ): 1.24 (3H, t, J=7 Hz), 3.96 (2H, q, J=7 Hz), 4.84 (2H, s), 7.39 (1H, dd, J=2 Hz, 8 Hz), 7.66 (1H, d, J=8 Hz), 7.72 (1H, d, J=2 Hz), 9.24 (1H, s)

(2) 4-Bromomethyl-2-(N-ethylformamido)benzoxazole
mp: 90°–92° C.
IR (Nujol): 1695, 1630, 1610, 1560 cm$^{-1}$ NMR (DMSO-$d_6$, δ): 1.59 (3H, t, J=7 Hz), 3.98 (2H, q, J=7 Hz), 4.93 (2H, s), 7.33 (1H, d, J=7 Hz), 7.42–7.82 (1H, m), 7.51 (1H, d, J=8 Hz), 9.28 (1H, s)

Preparation 74

The following compounds were obtained according to a similar manner to that of Preparation 62.

(1) 2-[2-(4-Nitrophenyl)vinyl]-7-methoxy-3-methylimidazo[1,2-a]pyridine
mp: 209°–211° C.
IR (Nujol): 1650, 1630, 1585, 1330 cm$^{-1}$
NMR (DMSO-$d_6$, δ): 2.59 (3H, s), 3.67 (3H, s), 6.65 (b 1H, dd, J=2 Hz, 8 Hz), 7.47–8.37 (8H, m)

(2) 2-[2-(4-Acetamido-3-nitrophenyl)vinyl]-7-methoxy-3-methylimidazo[1,2-a]pyridine
mp: 227°–230° C.
IR (Nujol): 3300, 1700, 1640, 1585 cm$^{-1}$
NMR (TFA, δ): 2.56 (3H, s), 2.76 (3H, s), 4.14 (3H, s), 7.10–7.46 (4H, m), 7.90–8.39 (2H, m), 8.43–8.73 (2H, m), 10.48 (1H, s)

(3) 2-[2-(3-Benzyloxy-4-nitrophenyl)vinyl]-3,6-dimethylimidazo[1,2-a]pyridine
mp: 154°–155° C.
IR (Nujol): 1600, 1585 cm$^{-1}$
NMR (DMSO-$d_6$, δ): 2.32 (3H, s), 2.61 (3H, s), 5.42 (2H, s), 7.01–7.79 (11H, m), 7.93 (1H, d, J=8 Hz), 8.05 (1H, s)

(4) 2-[2-(3-Benzyloxy-4-nitro-phenyl)vinyl]-3,8-dimethylimidazo[1,2-a]pyridine
mp: 140°–142° C.
IR (Nujol): 1630, 1600, 1585 cm$^{-1}$
NMR (TFA, δ): 2.78 (3H, s), 2.81 (3H, s), 5.47 (2H, s), 7.08–8.09 (11H, m), 8.23 (1H, d, J=8 Hz), 8.33 (1H, d, J=7 Hz)

(5) 2-[2-(3-Benzyloxy-4-nitrophenyl)vinyl]-7-ethyl-3-methylimidazo[1,2-a]pyridine
mp: 142°–146° C.
NMR (DMSO-$d_6$, δ): 1.23 (3H, t, J=7 Hz), 2.61 (3H, s), 2.69 (2H, q, J=7 Hz), 5.42 (2H, s), 6.78 (1H, dd, J=2 Hz, 7 Hz), 7.23–7.83 (10H, m), 7.92 (1H, d, J=8 Hz), 8.19 (1H, d, J=7 Hz)

(6) 2-[2-(3-Benzyloxy-4-nitrophenyl)vinyl]-8-methoxy-3-methylimidazo[1,2-a]pyridine
NMR (DMSO-$d_6$, δ): 2.62 (3H, s), 3.97 (3H, s), 5.44 (2H, s), 6.60–7.01 (2H, m), 7.30–8.07 (11H, m)

(7) 2-[2-(3-Benzyloxy-4-nitrophenyl)vinyl]-7-benzyloxy-3-methylimidazo[1,2-a]pyridine
mp: 168°–169° C.
IR (Nujol): 1640, 1630, 1600, 1580 cm$^{-1}$
NMR (DMSO-$d_6$, δ): 2.59 (3H, s), 5.12 (2H, s), 5.42 (2H, s), 6.71 (1H, dd, J=2 Hz, 7 Hz), 7.29–7.82 (15H, m), 7.93 (1H, d, J=8 Hz), 8.10 (1H, d, J=7 Hz)

(8) 2-[2-(3-Benzyloxy-4-nitrophenyl)vinyl]-8-benzyloxy-3-methylimidazo[1,2-a]pyridine
mp: 130°–136° C.
IR (Nujol): 1600, 1590, 1550 cm$^{-1}$
NMR (DMSO-$d_6$, δ): 2.63 (3H, s), 5.33 (2H, s), 5.41 (2H, s), 6.77–6.93 (2H, m), 7.30–8.08 (16H, m)

(9) 2-[2-(4-Acetamido-3-nitrophenyl)vinyl]-3,7-dimethylimidazo[1,2-a]pyridine
mp: 245°–246° C.
IR (Nujol): 1700, 1680, 1640, 1600, 1580 cm$^{-1}$
NMR (DMSO-$d_6$, δ): 2.08 (3H, s), 2.37 (3H, s), 2.57 (3H, s), 6.74 (1H, dd, J=2 Hz, 7 Hz), 7.23–7.67 (2H, m), 7.27 (1H, s), 7.64 (1H, d, J=8 Hz), 7.98 (1H, d, J=8 Hz), 8.11 (1H, d, J=7 Hz), 8.25 (1H, s), 10.26 (1H, s)

(10) 2-[2-(3-Benzyloxy-4-nitrophenyl)vinyl]-3,7-dimethylimidazo[1,2-a]pyrimidine
mp: 239°–242° C.
IR (Nujol): 3370 (br), 1620, 1590, 1580 cm$^{-1}$ NMR (TFA, δ): 2.80 (3H, s), 2.94 (3H, s), 5.45 (2H, s), 7.05–7.78 (10H, m), 8.00–8.38 (1H, m), 8.68–8.91 (1H, m)

Preparation 75

A mixture of (3-chloro-2-oxobutylidene)triphenylphosphorane (52.0 g) and 4-(N-methylacetamido)-3-nitrobenzaldehyde (31.5 g) in tetrahydrofuran (360 ml) was refluxed for 2 hours. The solvent was distilled off in vacuo and the residue was dissolved in ethanol (360 ml). To the resulting mixture was added a 2-amino-4-picoline (38.3 g) and the mixture was refluxed for 2 hours. The solvent was distilled off in vacuo. To the residue was added a mixture of ethyl acetate (400 ml) and water (400 ml) and the mixture was adjusted to pH 1 with conc. hydrochloric acid. The isolated precipitate was collected by filtration. To the resulting precipitate was added a mixture of 6N-hydrochloric acid (250 ml) and ethanol (200 ml), and the mixture was refluxed for 16 hours. Evaporation of the solvent gave a residue, which was added to a water, and the mixture was adjusted to pH 8 with saturated aqueous potassium carbonate. The isolated precipitate was collected by filtration and dried to give 2-[2-(4-methylamino-3-nitrophenyl)vinyl]-3,7-dimethylimidazo[1,2-a]pyridine (21.6 g).

NMR (DMSO-$d_6$, δ): 2.37 (3H, s), 2.52 (3H, s), 2.99 (3H, d, J=5 Hz), 6.51–6.87 (1H, m), 6.90–7.37 (3H, s), 7.44–7.93 (3H, m), 7.97–8.30 (2H, m)

Preparation 76

The following compounds were obtained according to a similar manner to that of Example 92.

(1) 2-Acetamido-5-[2-(4-nitrophenyl)vinyl]pyridine
mp: 211°–213° C.
IR (Nujol): 1680, 1590, 1560, 1500 cm$^{-1}$
NMR (DMSO-$d_6$, δ): 2.13 (3H, s), 7.20–8.43 (9H, m), 10.45 (1H, s)

(2) 5-Methyl-4-[2-(4-nitrophenyl)vinyl]-1-tritylimidazole
IR (Nujol): 1595, 1510, 1335 cm$^{-1}$ (3) 4-[2-(4-Acetamido-3-nitrophenyl)vinyl]-5-methyl-1-tritylimidazole
mp: 203°–206° C.

(4) 2-[2-(4-Acetamido-3-nitrophenyl)vinyl]furan
mp: 74° to 78° C.
IR (Nujol): 3325, 1510, 1325 cm$^{-1}$
NMR (DMSO-$d_6$, δ): 2.13 (3H, s), 6.48–6.60 (4H, m), 7.65 (1H, d, J=2 Hz), 7.77 (4H, m), 8.08 (1H, d, J=2 Hz), 10.30 (1H, s)

(5) 2-[2-(4-Nitrophenyl)vinyl]furan
mp: 122°–125° C.
IR (Nujol): 1635, 1515, 1340 cm$^{-1}$
NMR (DMSO-$d_6$, δ): 6.60 (1H, dd, J=2 Hz, 4 Hz), 6.73 (1H, d, J=4 Hz), 7.05 (1H, , J=16 Hz), 7.43 (1H, d, J=16 Hz), 7.78 (1H, d, J=2 Hz), 7.80 (2H, d, J=8 Hz), 8.20 (2H, d, J=8 Hz)

Preparation 77

A mixture of acetic anhydride (6 ml), 2-acetamido-6-methylpyridine (8.00 g) and 3-benzyloxy-4-nitrobenzaldehyde (13.7 g), was heated at 180° C. for 22 hours with stirring. After cooling, the reaction mixture was dissolved in chloroform (150 ml). The solution was washed with aqueous potassium carbonate, dried over magnesium sulfate and evaporated in vacuo. The residue was chromatographed on silica gel (640 g) by eluting with chloroform and washed with a mixture of ethyl acetate and diisopropyl ether to give 2-acetamido-6-[2-(3-benzyloxy-4-nitrophenyl)vinyl]pyridine (4.80 g).
mp: 144°–145° C.
IR (Nujol): 3225, 3175, 1655, 1580, 1375 cm$^{-1}$
NMR (DMSO-$d_6$, δ): 2.17 (3H, s), 5.45 (2H, s), 7.22–8.13 (14H, m), 10.45 (1H, s)

Preparation 78

A mixture of 2-[2-(4-acetamido-3-nitrophenyl)vinyl]-7-methoxy-3-methylimidazo[1,2-a]pyridine (8.2 g) in ethanol (80 ml) and 6N-hydrochloric acid (80 ml) was refluxed for 4 hours and the mixture was cooled to ambient temperature. The isolated precipitate was collected by filtration. To a precipitate was added water, and a mixture was adjusted to pH 8 with saturated aqueous potassium carbonate. The precipitate was collected by filtration and dried to give 2-[2-(4-amino-3-nitrophenyl)vinyl]-7-methoxy-3-methylimidazo[1,2-a]pyridine (7.62 g).
mp: 260°–261° C.
IR (Nujol): 1630, 1550 cm$^{-1}$
NMR (TFA, δ): 2.77 (3H, s), 4.15 (3H, s), 7.11–7.61 (4H, m), 7.83–8.44 (3H, m), 8.71 (1H, s)

Preparation 79

2-[2-(4-Amino-3-nitrophenyl)vinyl]furan was obtained according to a similar manner to that of Preparation 78.
mp: 111°–114° C.
IR (Nujol): 3440, 3320, 1505, 1335 cm$^{-1}$
NMR (DMSO-$d_6$, δ): 6.48–6.62 (2H, m), 6.90–7.15 (3H, m), 6.98 (2H, s), 7.11 (1H, d, J=9 Hz), 7.73 (1H, dd, J=2 Hz, 9 Hz), 8.10 (1H, d, J=2 Hz)

Preparation 80

A mixture of 4-[2-(4-acetamido-3-nitrophenyl)vinyl]-5-methyl-1-tritylimidazole (6.3 g) in ethanol (60 ml) and 1N-sodium hydroxide (23.8 ml) was refluxed for 1 hour and the mixture was cooled. The isolated precipitate was collected by filtration and the precipitate was washed with aqueous ethanol to give 4-[2-(4-amino-3-nitrophenyl)vinyl]-5-methyl-1-tritylimidazole (2.82 g).
mp: 188°–194° C.
NMR (TFA, δ): 2.25 (3H, s), 6.90 (1H, d, J=13 Hz),

Preparation 81

A solution of 2-[2-(3-benzyloxy-4-nitrophenyl)vinyl]-7-methylimidazo[1,2-a]pyridine (9.00 g) in N,N-dimethylformamide (50 ml), was added dropwise to a solution of phosphorus oxychloride (6.36 ml) in N,N-dimethylformamide (90 ml) at ambient temperature with stirring. After the mixture was stirred for 6 hours, the solvent was evaporated in vacuo. The residue was mixed with water (200 ml) and dichloromethane (300 ml) and made basic with aqueous potassium carbonate. The resulting precipitate was collected, washed with water and recrystallized from a mixture of methanol, chloroform and dioxane to give 2-[2-(3-benzyloxy-4-nitrophenyl)vinyl]-3-formyl-7-methylimidazo[1,2-a]pyridine (5.15 g).
mp: 200°–201° C.
IR (Nujol): 1630, 1510, 1360 cm$^{-1}$
NMR (DMSO-$d_6$, δ): 2.48 (3H, s), 5.42 (2H, s), 7.13 (1H, dd, J=1.5 Hz, 7 Hz), 7.30–8.03 (10H, m), 7.40 (1H, d, J=1.5 Hz), 9.30 (1H, d, J=7 Hz), 10.35 (1H, s)

Preparation 82

The following compounds were obtained according to a similar manner to that of Preparation 64.

(1) 2-[2-(4-Aminophenyl)ethyl]-7-methoxy-3-methylimidazo[1,2-a]pyridine
mp: 112°–115° C.
IR (Nujol): 3360, 3300, 3140, 1640, 1605 cm$^{-1}$
NMR (DMSO-d$_6$, δ): 2.21 (3H, s), 2.80 (4H, s), 3.83 (3H, s), 6.51 (2H, d, J=8 Hz), 6.58 (1H, dd, J=3 Hz, 7 Hz), 6.89 (1H, d, J=3 Hz), 6.90 (2H, d, J=8 Hz), 8.00 (1H, d, J=7 Hz)

(2) 2-[2-(3,4-Diaminophenyl)ethyl]-7-methoxy-3-methylimidazo[1,2-a]pyridine
mp: 205°–208° C.
IR (Nujol): 3390, 3330, 3220, 1670, 1620, 1590 cm$^{-1}$
NMR (DCl-D$_2$O, δ): 2.61 (3H, s), 3.18 (4H, s), 4.03 (3H, s), 7.10 (1H, dd, J=2 Hz, 8 Hz), 7.22 (1H, s), 7.47–7.82 (3H, m), 8.26 (1H, d, J=7 Hz)

(3) 2-[2-(4-Amino-3-hydroxyphenyl)ethyl]-3,6-dimethylimidazo[1,2-a]pyridine
mp: 225°–229° C.
IR (Nujol): 1660, 1610, 1570 cm$^{-1}$ (4) 2-[2-(4-Amino-3-hydroxyphenyl)ethyl]-3,8-dimethylimidazo[1,2-a]pyridine
mp: 185°–188° C.
IR (Nujol): 3400, 3340, 1620, 1590 cm$^{-1}$
NMR (DCl-D$_2$O, δ): 2.24 (3H, s), 2.64 (3H, s), 3.04–3.31 (4H, m), 6.69–7.00 (1H, m), 6.86 (1H, s), 7.24–7.54 (2H, m), 7.73 (1H, d, J=7 Hz), 8.25 (1H, d, J=7 Hz)

(5) 2-[2-(4-Amino-3-hydroxyphenyl)ethyl]-7-ethyl-3-methylimidazo[1,2-a]pyridine
mp: 134°–136° C.
IR (Nujol): 3440, 3340, 1640, 1620, 1580 cm$^{-1}$
NMR (DCl-D$_2$O, δ): 1.36 (3H, t, J=7 Hz), 2.24 (3H, s), 2.75–3.32 (6H, m), 6.67 (1H, dd, J=2 Hz, 8 Hz), 6.76 (1H, d, J=2 Hz), 7.12 (1H, d, J=8 Hz), 7.32 (1H, dd, J=2 Hz, 7 Hz), 7.59 (1H, s), 8.22 (1H, d, J=7 Hz)

(6) 2-[2-(4-Amino-3-hydroxyphenyl)ethyl]-8-methoxy-3-methylimidazo[1,2-a]pyridine
mp: 85°–91° C.
IR (Nujol): 1620, 1570, 1550 cm$^{-1}$
NMR (DCl-D$_2$O, δ): 2.23 (3H, s), 2.84–3.37 (4H, m), 4.15 (3H, s), 6.68–6.89 (2H, m), 7.15–7.61 (3H, m), 7.93 (1H, dd, J=2 Hz, 7 Hz)

(7) 2-[2-(4-Amino-3-hydroxyphenyl)ethyl]-7-hydroxy-3-methylimidazo[1,2-a]pyridine
mp: 172°–176° C.
IR (Nujol): 1660, 1640, 1590 cm$^{-1}$
NMR (DCl-D$_2$O, δ): 2.20 (3H, s), 2.80–3.33 (4H, m), 6.83 (1H, dd, J=2 Hz, 8 Hz), 7.89 (1H, s), 6.98–7.13 (2H, m), 7.34 (1H, d, J=8 Hz), 8.22 (1H, d, J=8 Hz)

(8) 2-[2-(4-Amino-3-hydroxyphenyl)ethyl]-8-hydroxy-3-methylimidazo[1,2-a]pyridine
mp: 102°–107° C.
IR (Nujol): 3330, 1650, 1620, 1590 cm$^{-1}$
NMR (DCl-D$_2$O, δ): 2.23 (3H, s), 2.96–3.26 (4H, m), 6.79 (1H, dd, J=2 Hz, 8 Hz), 6.87 (1H, s), 7.18–7.37 (1H, m), 7.23 (1H, d, J=5Hz), 7.34 (1H, d, J=8 Hz), 7.82–8.00 (1H, m)

(9) 2-[2-(3-Amino-4-methylaminophenyl)ethyl]-3,7-dimethylimidazo[1,2-a]pyridine
mp: 101°–104° C.
IR (Nujol): 3430, 3370, 3220, 1655, 1640, 1610, 1580 cm$^{-1}$
NMR (DCl-D$_2$O, δ): 2.25 (3H, s), 2.59 (3H, s), 2.70–3.33 (7H, m), 6.47–6.87 (2H, m), 6.86 (1H, d, J=8 Hz), 7.24 (1H, dd, J=2 Hz, 7 Hz), 7.55 (1H, s), 8.16 (1H, d, J=7 Hz)

(10) 2-[2-(4-Acetamido-3-aminophenyl)ethyl]-3,7-dimethylimidazo[1,2-a]pyridine
mp: 168°–173° C.
IR (Nujol): 1673, 1638 (br) cm$^{-1}$
NMR (DMSO-d$_6$, δ): 2.04 (3H, s), 2.29 (3H, s), 2.36 (3H, s), 2.85 (4H, s), 6.43 (1H, dd, J=2 Hz, 8 Hz), 6.63 (1H, d, J=2 Hz), 6.73 (1H, dd, J=2 Hz, 7 Hz), 7.10 (1H, d, J=8 Hz), 7.27 (1H, s), 8.06 (1H, d, J=7 Hz), 9.16 (1H, s)

(11) 2-[2-(4-Amino-3-hydroxyphenyl)ethyl]-3,7-dimethylimidazo[1,2-a]pyrimidine
mp: 187°–192° C.
IR (Nujol): 3460, 3350, 1630, 1590 cm$^{-1}$
NMR (DCl-D$_2$O, δ): 2.21 (3H, s), 2.75 (3H, s), 2.86–3.30 (4H, m), 6.71 (1H, dd, J=2 Hz, 8 Hz), 6.75 (1H, s), 7.17 (1H, d, J=8 Hz), 7.45 (1H, d, J=7 Hz), 8.64 (1H, d, J=7 Hz)

(12) 2-Acetamido-6-[2-(4-aminophenyl)ethyl]pyridine
mp: 167°–169° C.
NMR (DMSO-d$_6$, δ): 2.12 (3H, s), 2.87 (4H, s), 4.80 (2H, s), 6.53 (2H, d, J=8 Hz), 6.95 (1H, dd, J=2,7 Hz), 6.99 (2H, d, J=8 Hz), 7.67 (1H, dd, J=7 Hz, 7 Hz), 7.97 (1H, dd, J=2 Hz, 7 Hz), 10.40 (1H, s)

(13) 2-Acetamido-6-[2-(4-amino-3-hydroxyphenyl)ethyl]pyridine
mp: 169°–172° C.
IR (Nujol): 3365, 3300, 1670 cm$^{-1}$
NMR (DMSO-d$_6$, δ): 2.28 (3H, s), 2.75–2.90 (4H, m), 4.50 (2H, br s), 6.35–6.63 (3H, m), 6.92 (1H, dd, J=1 Hz, 7 Hz), 7.63 (1H, t, J=7 Hz), 7.95 (1H, dd, J=1 Hz, 7 Hz), 10.38 (1H, s)

(14) 4-[2-(4-Aminophenyl)ethyl]-5-methyl-1-tritylimidazole
mp: 70°–80° C.
IR (Nujol): 3220, 3100, 1610 (br) cm$^{-1}$

(15) 4-[2-(3,4-Diaminophenyl)ethyl]-5-methyl-1-tritylimidazole
NMR (DCl-D$_2$O, δ): 1.38 (3H, s), 3.10–3.42 (4H, m), 7.00–7.92 (18H, m), 8.58 (1H, s)

(16) 2-[2-(4-Aminophenyl)ethyl]furan
mp: 38°–40° C.
IR (Nujol): 3440, 3360, 1625 cm$^{-1}$
NMR (DMSO-d$_6$, δ): 2.77 (4H, s), 4.78 (2H, s), 6.06 (1H, d, J=3 Hz), 6.32 (1H, dd, J=2 Hz, 3 Hz), 6.52 (2H, d, J=8 Hz), 6.88 (2H, d, J=8 Hz), 7.48 (1H, d, J=2 Hz)

(17) 2-[2-(3,4-Diaminophenyl)ethyl]furan
mp: 79°–81° C.
IR (Nujol): 3360, 3270 cm$^{-1}$
NMR (DMSO-d$_6$, δ): 2.57–2.87 (4H, m), 4.26 (4H, s), 6.04 (1H, dd, J=1.5 Hz, 4 Hz), 6.23 (1H, dd, J=2 Hz, 8 Hz), 6.30–6.34 (1H, m), 6.42 (1H, d, J=2 Hz), 6.43 (1H, d, J=8 Hz), 7.43–7.46 (1H, m)

(18) 2-[2-(4-Amino-3-hydroxyphenyl)ethyl]-3-formyl-7-methylimidazo[1,2-a]pyridine
mp: >250° C.
IR (Nujol): 3600, 3460, 3360, 3125, 1615 cm$^{-1}$
NMR (DMSO-d$_6$, δ): 2.43 (3H, s), 2.85–3.18 (4H, m), 6.43–6.53 (3H, m), 7.10 (1H, dd, J=1.5 Hz, 7 Hz), 7.58 (1H, d, J=1.5 Hz), 9.27 (1H, d, J=7 Hz), 9.75 (1H, s)
Mass (m/e): 295 (M+), 266, 122

Preparation 83

Acetyl chloride (1.5 ml) was dropwise added to a mixture of 2-[2-(4-amino-3-hydroxyphenyl)ethyl]-3,7-dimethylimidazo[1,2-a]pyridine (5.0 g) and sodium bicarbonate (3.0 g) in acetone (30 ml) and water for 10 minutes under ice-cooling and the mixture was stirred for 30 minutes at the same temperature. To the mixture was added a solution of ethyl acetate, tetrahydrofuran and water, and separated organic layer was washed with brine. The mixture was dried over magnesium sulfate and concentrated to give 2-[2-(4-acetamido-3-hydroxyphenyl)ethyl]-3,7-dimethylimidazo[1,2-a]pyridine (3.51 g).

mp: 195°–198° C.

IR (Nujol): 3420, 1675, 1650, 1600 cm$^{-1}$

NMR (DMSO-d$_6$, δ): 2.08 (3H, s), 2.24 (3H, s), 2.34 (3H, s), 2.86 (4H, s), 6.51–6.84 (2H, m), 6.69 (1H, s), 7.24 (1H, s), 7.51 (1H, d, J=8 Hz), 8.02 (1H, d, J=7 Hz), 9.30 (1H, s)

Preparation 84

3,7-Dimethyl-2-[2-(3-hydroxy-4-propionamidophenyl)ethyl]imidazo[1,2-a]pyridine was obtained according to a similar manner to that of Preparation 83.

mp: 194°–199° C.

IR (Nujol): 3420, 1677, 1650, 1603 cm$^{-1}$

NMR (DMSO-d$_6$, δ): 1.09 (3H, t, J=7 Hz), 2.07–2.67 (2H, m), 2.25 (3H, s), 2.36 (3H, s), 2.88 (4H, s), 6.62 (1H, dd, J=2 Hz, 7 Hz), 6.73 (1H, s), 6.73 (1H, dd, J=2 Hz, 8 Hz), 7.26 (1H, s), 7.54 (1H, d, J=8 Hz), 8.03 (1H, d, J=7 Hz), 9.23 (1H, s)

Preparation 85

Acetic anhydride (0.28 ml) was added dropwise to a solution of 2-[2-(4-aminophenyl)ethyl]furan (0.50 g) in pyridine (5 ml) at ambient temperature with stirring. After being stirred for 1 hour, the mixture was poured into water (50 ml) and the resulting precipitate was collected by filtration to give 2-[2-(4-acetamidophenyl)ethyl]furan (0.58 g).

mp: 123°–125° C.

IR (Nujol): 3320, 1665 cm$^{-1}$

NMR (DMSO-d$_6$, δ): 2.02 (3H, s), 2.86 (4H, s), 6.06 (1H, d, J=3 Hz), 6.32 (1H, dd, J=1.5 Hz, 3 Hz), 7.12 (2H, d, J=9 Hz), 7.50 (1H, d, J=1.5 Hz), 7.51 (2H, d, J=9 Hz), 9.87 (1H, s)

Preparation 86

A mixture of 2-[2-(4-acetamidophenyl)ethyl]furan (0.50 g), 37% formalin (0.26 ml) and dimethylamine hydrochloride (0.27 g) in acetic acid (5 ml) was stirred at ambient temperature for 1 hour and at 50° C. for further 1 hour. The solvent was evaporated in vacuo. The residue was mixed with saturated aqueous sodium bicarbonate and extracted with ethyl acetate. The extract was washed with water, dried over magnesium sulfate and evaporated in vacuo to give 2-[2-(4-acetamidophenyl)ethyl]-5-dimethylaminomethylfuran (0.57 g) as an oil.

IR (film): 3260, 3170, 3110, 1660 cm$^{-1}$

NMR (DMSO-d$_6$, δ): 2.01 (3H, s), 2.12 (6H, s), 2.82 (4H, s), 3.35 (2H, s), 5.96 (1H, d, J=3 Hz), 6.12 (1H, d, J=3 Hz), 7.12 (2H, d, J=8 Hz), 7.49 (2H, d, J=8 Hz), 9.86 (1H, s)

Preparation 87

2-[2-(4-Aminophenyl)ethyl]-5-dimethylaminomethylfuran was obtained according to a similar manner to that of Preparation 78.

IR (Nujol): 3350 cm$^{-1}$

NMR (DMSO-$_6$, δ): 2.13 (6H, s), 2.75 (4H, s), 4.63 (2H, br s), 5.95 (1H, d, J=3 Hz), 6.13 (1H, d, J=3 Hz), 6.50 (2H, d, J=8 Hz), 6.92 (2H, d, J=8 Hz)

Preparation 88

Pyridinium bromide perbromide (82.8 g) was added to a mixture of 1-(3-benzyloxy-4-nitrophenyl)but-1-en-3-one (70.0 g) and boron trifluoride etherate (290 ml) in tetrahydrofuran (1.4 l) under ice-cooling. The mixture was stirred for 2.5 hours at ambient temperature. The reaction mixture was added to a mixture of ethyl acetate and water under stirring. The separated organic layer was washed with saturated aqueous sodium bicarbonate and brine successively. The solution was dried over magnesium sulfate. The solvent was evaporated in vacuo and the residue was recrystallized from diisopropyl ether to give 4-bromo-1-(3-benzyloxy-4-nitrophenyl)but-1-en-3-one (54.42 g).

mp: 118°–119° C.

IR (Nujol): 1690, 1600 cm$^{-1}$

NMR (DMSO-d$_6$, δ): 4.56 (2H, s), 5.40 (2H, s), 7.19 (1H, d, J=17 Hz), 7.30–7.72 (7H, m), 7.77–8.08 (2H, m)

Preparation 89

A mixture of 4-bromo-1-(3-benzyloxy-4-nitrophenyl)-but-1-en-3-one (55.0 g) and 2-aminopyridine (42.3 g) in acetonitrile (380 ml) was stirred for 4 hours at ambient temperature. Ethyl acetate was added to the reaction mixture and the precipitate was collected by filtration. A mixture of water and ethyl acetate was added to the precipitate and the mixture was adjusted to pH 7.0 with 20% potassium carbonate. The precipitate was collected by filtration and washed with water to give 2-[2-(3-benzyloxy-4-nitrophenyl)vinyl]imidazo[1,2-a]pyridine (40.1 g).

mp: 126°–131° C.

IR (Nujol): 1640, 1610, 1590 cm$^{-1}$

NMR (DMSO-d$_6$, δ): 5.38 (2H, s), 6.87 (1H, t, J=7 Hz), 7.13–7.66 (10H, m), 7.70 (1H, s), 7.92 (1H, d, J=9 Hz), 8.09 (1H, s), 8.53 (1H, d, J=7 Hz)

Preparation 90

2-[2-(4-Benzyloxy-3-nitrophenyl)vinyl]imidazo[1,2-a]pyridine was obtained according to a similar manner to that of Preparation 62.

mp: 115°–120° C.

IR (Nujol): 3400, 3250, 1610, 1530, 1370 cm$^{-1}$

NMR (CD$_3$OD-CDCl$_3$, δ): 5.22 (2H, s), 6.5–7.0 (2H, m), 7.0–7.1 (8H, m), 7.2–8.3 (2H, m)

Preparation 91

10% Palladium on carbon (3.0 g) was added to a mixture of 2-[2-(3-benzyloxy-4-nitrophenyl)ethyl]-3-methylimidazo[1,2-a]pyridine (6.5 g) in a mixture of methanol and tetrahydrofuran, and the mixture was subjected to catalytic reduction under atmospheric pressure for 3 hours at ambient temperature. The catalyst was removed by filtration and the filtrate was evaporated in vacuo. The residue was purified by a column chromatography on silica gel, and eluted with a mixture of chloroform and methanol (9:1, V/V). The eluted fast fractions containing the desired product were collected and evaporated in vacuo to give 2-[2-(4-amino-3-hydroxyphenyl)ethyl]-3-methylimidazo[1,2-a]pyridine (1.37 g).

mp: 132°–139° C.

IR (Nujol): 3420, 3330, 1620, 1590 cm$^{-1}$

NMR (DCl-D$_2$O, δ): 2.30 (3H, s), 2.94–3.42 (4H, m), 6.81 (1H, dd, J=2 Hz, 8 Hz), 6.89 (1H, s), 7.34 (1H, d, J=8 Hz), 7.45–7.67 (1H, s), 7.83–8.00 (2H, m), 8.42 (1H, d, J=7 Hz)

The eluted another fractions containing the desired product were collected and evaporated in vacuo to give 2-[2-(4-amino-3-hydroxyphenyl)ethyl]-3-methyl-5,6,7,8-tetrahydroimidazo[1,2-a]pyridine (0.98 g).

IR (Nujol): 3425, 3350, 1590 (br) cm$^{-1}$

NMR (DCl-D$_2$O, δ): 1.88–2.20 (4H, m), 1.90 (3H, s), 2.77–3.15 (2H, m), 2.93 (4H, s), 3.80–4.11 (2H, m), 6.80 (1H, dd, J=2 Hz, 8 Hz), 6.85 (1H, s), 7.32 (1H, d, J=8 Hz)

Preparation 92

10% Palladium on carbon (1.0 g) was added to a mixture of 2-[2-(4-aminophenyl)ethyl]-7-methylimidazo[1,2-a]pyridine (4.0 g) in methanol (100 ml) and 1N-hydrochloric acid (60 ml) and the mixture was subjected to catalytic reduction at ambient temperature under atmospheric pressure. The catalyst was removed by filtration and the filtrate was evaporated in vacuo. To the residue was added a mixture of ethyl acetate and water and the mixture was adjusted to pH 8 with potassium carbonate. The separated organic layer was washed with brine and dried over magnesium sulfate. The solvent was evaporated and the residue was triturated with a solution of diethyl ether and ethyl acetate. The precipitate was collected by filtration and dried to give 2-[2-(4-aminophenyl)ethyl]-7-methyl-5,6,7,8-tetrahydroimidazo[1,2-a]pyridine (3.39 g).

mp: 135°–138° C.

IR (Nujol): 3350, 3250, 1640, 1615 cm$^{-1}$

NMR (D$_2$-DCl, δ): 1.15 (3H, d, J=6 Hz), 1.43–2.32 (3H, m), 2.32–2.73 (1H, m), 1.88–3.30 (1H, m), 2.97 (4H, m), 3.89–4.34 (2H, m), 6.96 (1H, s), 7.14 (2H, d, J=9 Hz), 7.27 (2H, d, J=9 Hz)

Preparation 93

A solution of 2-[2-(3-benzyloxy-4-nitrophenyl)vinyl]imidazo[1,2-a]pyridine (40 g) in ethanol (600 ml) was hydrogenated over 10% palladium on carbon (10 g) at 4 to 6 atmospheric pressure of hydrogen gas for 4 hours at 40° to 70° C. The catalyst was removed by filtration an the filtrate was evaporated in vacuo to give a crystalline residue, which was washed with diethyl ether and dried to give 2-[2-(4-amino-3-hydroxyphenyl)ethyl]-5,6,7,8-tetrahydroimidazo[1,2-a]pyridine (19.0 g).

mp: 178°–181° C.

IR (Nujol): 1620, 1595, 1540, 1500 cm$^{-1}$

NMR (DMSO-d$_6$, δ): 1.67–1.97 (4H, m), 2.41–2.88 (6H, m), 3.67–4.01 (2H, m), 6.39–6.58 (3H, m), 6.61 (1H, s)

Preparation 94

2-[2-(3-Amino-4-hydroxyphenyl)ethyl]-5,6,7,8-tetrahydroimidazo[1,2-a]pyridine was obtained according to a similar manner to that of Preparation 93.

mp: 166°–169° C.

IR (Nujol): 3450, 3350, 1620, 1520 cm$^{-1}$

NMR (CDCl$_3$+CD$_3$OD, δ): 1.7–2.1 (4H, m), 2.7–2.9 (6H, s), 3.7–4.0 (2H, m), 4.73 (3H, s), 6.43 (1H, dd, J=2 Hz, 9 Hz), 6.43 (1H, s), 6.58 (1H, d, J=2 Hz), 6.65 (1H, d, J=9 Hz)

Preparation 95

The following compounds were obtained according to a similar manner to that of Preparation 52.

(1) 2-[2-{4-Hydroxy-3-(3-ethylureido)phenyl}ethyl]-5,6,7,8-tetrahydroimidazo[1,2-a]pyridine mp: 199°–200° C.

IR (Nujol): 3350, 1640, 1570, 1490, 1440 cm$^{-1}$

NMR (CDCl$_3$, —CD$_3$OD, δ): 1.16 (3H, t, J=7 Hz), 1.6–2.2 (4H, m), 2.79 (6H, s), 3.26 (2H, q, J=7 Hz), 3.5–4.1 (2H, m), 6.47 (1H, s), 6.80 (2H, br), 7.08 (1H, br)

(2) 2-[2-{3-Hydroxy-4-(3-ethylureido)phenyl}ethyl]-5,6,7,8-tetrahydro[1,2-a]pyridine mp: 200°–202° C.

IR (Nujol): 3380, 3320, 1640, 1610 cm$^{-1}$

NMR (DMSO-d$_6$, δ): 1.05 (3H, t, J=7 Hz), 1.61–1.99 (4H, m), 2.39–2.80 (6H, m), 2.84–3.26 (2H, m), 3.68–3.94 (2H, m), 6.25–6.92 (4H, m), 7.62 (1H, d, J=8 Hz), 7.75 (1H, s)

What we claim is:

1. A compound of the formula:

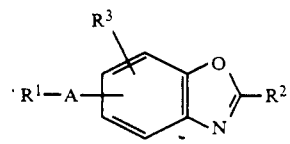

wherein

R$^1$ is pyridyl, imidazopyridyl or tetrahydroimidazopyridyl, each of which may be substituted with substituent(s) selected from the group consisting of amino; amino substituted with alkanoyl or diaminomethylene; hydroxy; hydroxy substituted with alkanoyl or lower alkyl; carboxy; alkanoyl; halogen; lower alkyl; and lower alkyl substituted with phenol, hydroxy, halogen, lower alkoxy, amino, lower alkylamino piperidino or azido, R$^2$ is amino or amino substituted with a substituent selected from the group consisting of lower alkyl, lower alkenyl, amidino, lower alkylamino(lower)alkylidene and alkanoyl, R$^3$ is hydrogen and A is lower alkylene, or a pharmaceutically acceptable salt thereof.

2. The compound of claim 1 which is 6-[2-(7-methoxy-3-methylimidazo[1,2-a]pyridin-2-yl)ethyl]-2-aminobenzoxazole dihydrochloride.

3. A antiulcer pharmaceutical composition comprising, as an active ingredient, an effective amount of a compound of claim 1 or pharmaceutically acceptable salt thereof in association with a pharmaceutical carrier.

4. A method for the treatment of ulcer in a human being or animal comprising administering an effective amount of a compound of claim 1 or a pharmaceutically acceptable salt thereof.

* * * * *